(12) United States Patent
Gilmore et al.

(10) Patent No.: US 10,052,095 B2
(45) Date of Patent: Aug. 21, 2018

(54) MULTIPLE ANCHORING-POINT TENSION SYSTEM

(71) Applicant: 4TECH INC., Waltham, MA (US)

(72) Inventors: Michael Gilmore, County Galway (IE); Idan Tobis, Beth Hashmonai (IL); Charlotte Murphy, County Galway (IE); Kevin Lynn, County Galway (IE)

(73) Assignee: 4TECH INC., Waltham, MA (US)

(*) Notice: Subject to any disclaimer, the term of this patent is extended or adjusted under 35 U.S.C. 154(b) by 349 days.

(21) Appl. No.: 15/147,599

(22) Filed: May 5, 2016

(65) Prior Publication Data
US 2016/0242762 A1 Aug. 25, 2016

Related U.S. Application Data

(63) Continuation-in-part of application No. 15/031,069, filed as application No. PCT/IB2014/002351 on Oct. 28, 2014.
(Continued)

(51) Int. Cl.
*A61B 17/04* (2006.01)
*A61F 2/24* (2006.01)
(Continued)

(52) U.S. Cl.
CPC ........ *A61B 17/0401* (2013.01); *A61F 2/2442* (2013.01); *A61F 2/89* (2013.01);
(Continued)

(58) Field of Classification Search
CPC ........ A61B 17/0401; A61B 2017/0414; A61B 2017/0496; A61F 2/2442; A61F 2/2454; A61F 2/246; A61F 2/2478; A61F 2/2487
See application file for complete search history.

(56) References Cited

U.S. PATENT DOCUMENTS

| | | |
|---|---|---|
| 4,214,349 A | 7/1980 | Munch |
| 4,405,313 A | 9/1983 | Sisley et al. |
| 4,423,525 A | 1/1984 | Vallana |

(Continued)

FOREIGN PATENT DOCUMENTS

| | | |
|---|---|---|
| DE | 102007043830 | 4/2009 |
| EP | 1568326 | 8/2005 |

(Continued)

OTHER PUBLICATIONS

USPTO, Non-Final Office Action, U.S. Appl. No. 15/353,230 (dated Oct. 23, 2017).
(Continued)

*Primary Examiner* — Diane Yabut
*Assistant Examiner* — Martin T Ton
(74) *Attorney, Agent, or Firm* — UltimatEdge IP Law Group, P.C.; Dean G. Stathakis; Vito A. Canuso, III

(57) ABSTRACT

A method is provided that includes implanting (a) a venous first tissue anchor in a vein selected from the group of veins consisting of: a superior vena cava and an inferior vena cava, (b) an atrial second tissue anchor at an atrial site selected from the group of sites consisting of: an annulus of a tricuspid valve, and a wall of a right atrium of a heart above the annulus of the tricuspid valve, (c) a venous third tissue anchor in a coronary sinus, and (d) one or more tethers, which connect the venous first tissue anchor, the atrial second tissue anchor, and the venous third tissue anchor. A size of a tricuspid orifice is reduced by tensioning the one or more tethers. Other embodiments are also described.

28 Claims, 44 Drawing Sheets

Related U.S. Application Data

(60) Provisional application No. 61/897,509, filed on Oct. 30, 2013.

(51) Int. Cl.
   *A61F 2/89* (2013.01)
   *A61B 17/00* (2006.01)

(52) U.S. Cl.
   CPC . *A61B 17/0466* (2013.01); *A61B 2017/00243* (2013.01); *A61B 2017/0409* (2013.01); *A61B 2017/0414* (2013.01); *A61B 2017/0441* (2013.01); *A61B 2017/0464* (2013.01); *A61B 2017/0496* (2013.01); *A61F 2/2487* (2013.01)

(56) References Cited

U.S. PATENT DOCUMENTS

| | | |
|---|---|---|
| 4,444,207 A | 4/1984 | Robicsek |
| 4,493,329 A | 1/1985 | Crawford et al. |
| 4,532,926 A | 8/1985 | O'Holla |
| 4,548,202 A | 10/1985 | Duncan |
| 4,602,911 A | 7/1986 | Ahmadi et al. |
| 4,625,727 A | 12/1986 | Leiboff |
| 4,712,549 A | 12/1987 | Peters et al. |
| 4,741,336 A | 5/1988 | Failla et al. |
| 4,778,468 A | 10/1988 | Hunt et al. |
| 4,808,157 A | 2/1989 | Coombs |
| 4,853,986 A | 8/1989 | Allen |
| 5,108,420 A | 4/1992 | Marks |
| 5,330,521 A | 7/1994 | Cohen |
| 5,336,233 A | 8/1994 | Chen |
| 5,350,399 A | 9/1994 | Erlebacher et al. |
| 5,450,860 A | 9/1995 | O'Connor |
| 5,473,812 A | 12/1995 | Morris et al. |
| 5,474,518 A | 12/1995 | Farrer-Velazquez |
| 5,776,178 A | 7/1998 | Pohndorf et al. |
| 5,792,400 A | 8/1998 | Talja et al. |
| 5,843,120 A | 12/1998 | Israel |
| 5,843,164 A | 12/1998 | Frantzen et al. |
| 5,904,697 A | 5/1999 | Gifford et al. |
| 5,948,000 A | 9/1999 | Larsen et al. |
| 5,957,953 A | 9/1999 | DiPoto et al. |
| 5,961,440 A | 10/1999 | Schweich, Jr. et al. |
| 6,010,113 A | 1/2000 | Rotering |
| 6,027,523 A | 2/2000 | Schmieding |
| 6,045,497 A | 4/2000 | Schweich, Jr. et al. |
| 6,050,936 A | 4/2000 | Schweich, Jr. et al. |
| 6,077,214 A | 6/2000 | Mortier et al. |
| 6,183,512 B1 | 2/2001 | Howanec et al. |
| 6,193,734 B1 | 2/2001 | Bolduc et al. |
| 6,206,913 B1 | 3/2001 | Yencho et al. |
| 6,210,432 B1 | 4/2001 | Solem et al. |
| 6,231,516 B1 | 5/2001 | Keilman et al. |
| 6,298,272 B1 | 10/2001 | Peterfeso et al. |
| 6,299,635 B1 | 10/2001 | Frantzen |
| 6,332,893 B1 | 12/2001 | Mortier et al. |
| 6,338,738 B1 | 1/2002 | Bellotti et al. |
| 6,402,780 B2 | 6/2002 | Williamson, IV et al. |
| 6,402,781 B1 | 6/2002 | Langberg et al. |
| 6,406,420 B1 | 6/2002 | McCarthy et al. |
| 6,461,336 B1 | 10/2002 | Larre |
| 6,533,810 B2 | 3/2003 | Hankh et al. |
| 6,537,198 B1 | 3/2003 | Vidlund et al. |
| 6,537,314 B2 | 3/2003 | Langberg et al. |
| 6,575,976 B2 | 6/2003 | Grafton |
| 6,585,766 B1 | 7/2003 | Huynh et al. |
| 6,602,288 B1 | 8/2003 | Cosgrove et al. |
| 6,613,078 B1 | 9/2003 | Barone |
| 6,613,079 B1 | 9/2003 | Wolinsky |
| 6,616,684 B1 | 9/2003 | Vidlund et al. |
| 6,619,291 B2 | 9/2003 | Hlavka et al. |
| 6,622,730 B2 | 9/2003 | Ekvall et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,641,597 B2 | 11/2003 | Burkhart et al. |
| 6,645,193 B2 | 11/2003 | Mangosong |
| 6,702,846 B2 | 3/2004 | Mikus |
| 6,709,456 B2 | 3/2004 | Langberg et al. |
| 6,718,985 B2 | 4/2004 | Hlavka et al. |
| 6,719,767 B1 | 4/2004 | Kimblad |
| 6,723,038 B1 | 4/2004 | Schroeder et al. |
| 6,730,118 B2 | 5/2004 | Spenser et al. |
| 6,743,198 B1 | 6/2004 | Tihon |
| 6,746,472 B2 | 6/2004 | Frazier et al. |
| 6,764,510 B2 | 7/2004 | Vidlund et al. |
| 6,776,754 B1 | 8/2004 | Wilk |
| 6,797,001 B2 | 9/2004 | Mathis |
| 6,810,882 B2 | 11/2004 | Langberg et al. |
| 6,884,250 B2 | 4/2005 | Monassevitch |
| 6,893,459 B1 | 5/2005 | Macoviak |
| 6,908,478 B2 | 6/2005 | Alfemess et al. |
| 6,929,660 B1 | 8/2005 | Ainsworth et al. |
| 6,989,028 B2 | 1/2006 | Lashinski et al. |
| 6,997,951 B2 | 2/2006 | Solem et al. |
| 7,011,682 B2 | 3/2006 | Lashinski et al. |
| 7,018,406 B2 | 3/2006 | Seguin et al. |
| 7,018,408 B2 | 3/2006 | Bailey et al. |
| 7,037,290 B2 | 5/2006 | Gardeski et al. |
| 7,041,097 B1 | 5/2006 | Webler |
| 7,044,967 B1 | 5/2006 | Solem et al. |
| 7,063,711 B1 | 6/2006 | Loshakove et al. |
| 7,077,861 B2 | 7/2006 | Spence |
| 7,083,628 B2 | 8/2006 | Bachman |
| 7,087,064 B1 | 8/2006 | Hyde |
| 7,094,244 B2 | 8/2006 | Schreck |
| 7,101,395 B2 | 9/2006 | Tremulis et al. |
| 7,101,396 B2 | 9/2006 | Artof et al. |
| 7,112,219 B2 | 9/2006 | Vidlund et al. |
| 7,125,421 B2 | 10/2006 | Tremulis et al. |
| 7,144,363 B2 | 12/2006 | Pai et al. |
| 7,159,593 B2 | 1/2007 | McCarthy et al. |
| 7,166,127 B2 | 1/2007 | Spence et al. |
| 7,169,187 B2 | 1/2007 | Datta |
| 7,175,625 B2 | 2/2007 | Culbert |
| 7,179,282 B2 | 2/2007 | Alferness et al. |
| 7,186,262 B2 | 3/2007 | Saadat |
| 7,189,199 B2 | 3/2007 | McCarthy et al. |
| 7,192,442 B2 | 3/2007 | Solem et al. |
| 7,192,443 B2 | 3/2007 | Solem et al. |
| 7,198,646 B2 | 4/2007 | Figulla et al. |
| 7,201,772 B2 | 4/2007 | Schwammenthal |
| 7,211,107 B2 | 5/2007 | Bruckheimer et al. |
| 7,211,110 B2 | 5/2007 | Rowe et al. |
| 7,241,257 B1 | 7/2007 | Ainsworth et al. |
| 7,247,134 B2 | 7/2007 | Vidlund et al. |
| 7,258,697 B1 | 8/2007 | Cox et al. |
| 7,291,168 B2 | 11/2007 | Macoviak et al. |
| 7,311,697 B2 | 12/2007 | Osborne |
| 7,311,728 B2 | 12/2007 | Solem et al. |
| 7,316,706 B2 | 1/2008 | Bloom et al. |
| 7,316,710 B1 | 1/2008 | Cheng et al. |
| 7,329,279 B2 | 2/2008 | Haug et al. |
| 7,331,972 B1 | 2/2008 | Cox |
| 7,335,213 B1 | 2/2008 | Hyde et al. |
| 7,338,506 B2 | 3/2008 | Caro |
| 7,351,256 B2 | 4/2008 | Hojeibane |
| 7,371,244 B2 | 5/2008 | Chatlynne et al. |
| 7,374,573 B2 | 5/2008 | Gabbay |
| 7,381,210 B2 | 6/2008 | Zarbatany et al. |
| 7,381,220 B2 | 6/2008 | Macoviak et al. |
| 7,390,329 B2 | 6/2008 | Westra et al. |
| 7,431,692 B2 | 10/2008 | Zollinger et al. |
| 7,431,726 B2 | 10/2008 | Spence et al. |
| 7,485,143 B2 | 2/2009 | Webler et al. |
| 7,500,989 B2 | 3/2009 | Solem et al. |
| 7,503,931 B2 | 3/2009 | Kowalsky et al. |
| 7,510,575 B2 | 3/2009 | Spenser et al. |
| 7,527,646 B2 | 5/2009 | Randert et al. |
| 7,530,995 B2 | 5/2009 | Quijano et al. |
| 7,547,321 B2 | 6/2009 | Silvestri et al. |
| 7,549,983 B2 | 6/2009 | Roue et al. |

(56) References Cited

U.S. PATENT DOCUMENTS

| | | |
|---|---|---|
| 7,597,703 B2 | 10/2009 | Sater |
| 7,608,102 B2 | 10/2009 | Adams et al. |
| 7,618,449 B2 | 11/2009 | Tremulis et al. |
| 7,628,797 B2 | 12/2009 | Tieu et al. |
| 7,632,303 B1 | 12/2009 | Stalker et al. |
| 7,637,946 B2 | 12/2009 | Solem et al. |
| 7,666,204 B2 | 2/2010 | Thornton et al. |
| 7,695,512 B2 | 4/2010 | Lashinski et al. |
| 7,704,277 B2 | 4/2010 | Zakay et al. |
| 7,722,523 B2 | 5/2010 | Mortier et al. |
| 7,758,632 B2 | 7/2010 | Hojeibane et al. |
| 7,771,467 B2 | 8/2010 | Svensson |
| 7,780,726 B2 | 8/2010 | Seguin |
| 7,785,366 B2 | 8/2010 | Maurer et al. |
| 7,803,187 B2 | 9/2010 | Hauser |
| 7,806,910 B2 | 10/2010 | Anderson |
| 7,837,727 B2 | 11/2010 | Goetz et al. |
| 7,841,502 B2 | 11/2010 | Walberg et al. |
| 7,857,846 B2 | 12/2010 | Alferness et al. |
| 7,871,433 B2 | 1/2011 | Lattouf |
| 7,883,539 B2 | 2/2011 | Schweich, Jr. et al. |
| 7,942,927 B2 | 5/2011 | Kaye et al. |
| 7,947,207 B2 | 5/2011 | Mcniven et al. |
| 7,972,378 B2 | 7/2011 | Tabor et al. |
| 7,991,484 B1 | 8/2011 | Sengupta et al. |
| 7,992,567 B2 | 8/2011 | Hirotsuka |
| 7,993,368 B2 | 8/2011 | Gambale et al. |
| 7,993,397 B2 | 8/2011 | Lashinski et al. |
| 8,010,207 B2 | 8/2011 | Smits et al. |
| 8,025,495 B2 | 9/2011 | Hardert et al. |
| 8,029,518 B2 | 10/2011 | Goldfarb et al. |
| 8,052,592 B2 | 11/2011 | Goldfarb et al. |
| 8,075,616 B2 | 12/2011 | Solem et al. |
| 8,092,520 B2 | 1/2012 | Quadri |
| 8,092,525 B2 | 1/2012 | Eliasen et al. |
| 8,100,820 B2 | 1/2012 | Hauser et al. |
| 8,108,054 B2 | 1/2012 | Helland |
| 8,109,996 B2 | 2/2012 | Stacchino et al. |
| 8,137,381 B2 | 3/2012 | Foerster et al. |
| 8,142,493 B2 | 3/2012 | Spence et al. |
| 8,142,495 B2 | 3/2012 | Hasenkam et al. |
| 8,147,542 B2 | 4/2012 | Maisano et al. |
| 8,157,810 B2 | 4/2012 | Case et al. |
| 8,172,898 B2 | 5/2012 | Alferness et al. |
| 8,197,441 B2 | 6/2012 | Webler et al. |
| 8,202,281 B2 | 6/2012 | Voss |
| 8,202,315 B2 | 6/2012 | Hlavka et al. |
| 8,216,302 B2 | 7/2012 | Wilson et al. |
| 8,226,707 B2 | 7/2012 | White |
| 8,236,013 B2 | 8/2012 | Chu |
| 8,236,049 B2 | 8/2012 | Rowe et al. |
| 8,252,005 B2 | 8/2012 | Findlay et al. |
| 8,262,567 B2 | 9/2012 | Sharp et al. |
| 8,262,724 B2 | 9/2012 | Seguin et al. |
| 8,262,725 B2 | 9/2012 | Subramanian |
| 8,267,981 B2 | 9/2012 | Boock et al. |
| 8,313,497 B2 | 11/2012 | Walberg et al. |
| 8,313,498 B2 | 11/2012 | Pantages et al. |
| 8,323,312 B2 | 12/2012 | Clark |
| 8,323,335 B2 | 12/2012 | Rowe et al. |
| 8,332,051 B2 | 12/2012 | Sommer et al. |
| 8,361,088 B2 | 1/2013 | McIntosh |
| 8,382,829 B1 | 2/2013 | Call et al. |
| 8,398,672 B2 | 3/2013 | Kleshinski et al. |
| 8,409,273 B2 | 4/2013 | Thornton et al. |
| 8,419,753 B2 | 4/2013 | Stafford |
| 8,430,893 B2 | 4/2013 | Ma |
| 8,449,606 B2 | 5/2013 | Eliasen et al. |
| 8,460,368 B2 | 6/2013 | Taylor et al. |
| 8,460,371 B2 | 6/2013 | Hlavka et al. |
| 8,475,525 B2 | 7/2013 | Maisano et al. |
| 8,480,691 B2 | 7/2013 | Dana et al. |
| 8,480,730 B2 | 7/2013 | Maurer et al. |
| 8,523,881 B2 | 9/2013 | Cabiri et al. |
| 8,524,132 B2 | 9/2013 | Von Oepen et al. |
| 8,529,621 B2 | 9/2013 | Alfieri et al. |
| 8,545,553 B2 | 10/2013 | Zipory et al. |
| 8,568,475 B2 | 10/2013 | Nguyen et al. |
| 8,568,476 B2 | 10/2013 | Rao et al. |
| 8,591,460 B2 | 11/2013 | Wilson et al. |
| 8,597,347 B2 | 12/2013 | Maurer et al. |
| 8,628,569 B2 | 1/2014 | Benichou et al. |
| 8,628,571 B1 | 1/2014 | Hacohen |
| 8,663,248 B2 | 3/2014 | Zung et al. |
| 8,685,080 B2 | 4/2014 | White |
| 8,685,083 B2 | 4/2014 | Perier et al. |
| 8,721,588 B2 | 5/2014 | Echarri et al. |
| 8,728,097 B1 | 5/2014 | Sugimoto et al. |
| 8,747,463 B2 | 6/2014 | Fogarty et al. |
| 8,753,357 B2 | 6/2014 | Roorda et al. |
| 8,753,373 B2 | 6/2014 | Chau et al. |
| 8,778,017 B2 | 7/2014 | Eliasen et al. |
| 8,784,481 B2 | 7/2014 | Alkhatib et al. |
| 8,790,394 B2 | 7/2014 | Miller et al. |
| 8,795,356 B2 | 8/2014 | Quadri et al. |
| 8,808,366 B2 | 8/2014 | Braido et al. |
| 8,808,368 B2 | 8/2014 | Maisano et al. |
| 8,845,723 B2 | 9/2014 | Spence et al. |
| 8,852,270 B2 | 10/2014 | Maurer et al. |
| 8,852,272 B2 | 10/2014 | Gross et al. |
| 8,858,594 B2 | 10/2014 | Clark |
| 8,858,623 B2 | 10/2014 | Miller et al. |
| 8,864,822 B2 | 10/2014 | Spence et al. |
| 8,870,949 B2 | 10/2014 | Rowe |
| 8,870,950 B2 | 10/2014 | Hacohen |
| 8,893,947 B2 | 11/2014 | Reynolds et al. |
| 8,911,461 B2 | 12/2014 | Traynor et al. |
| 8,926,691 B2 | 1/2015 | Chau et al. |
| 8,945,177 B2 | 2/2015 | Dell et al. |
| 8,945,211 B2 | 2/2015 | Sugimoto |
| 8,951,285 B2 | 2/2015 | Sugimoto et al. |
| 8,961,594 B2 | 2/2015 | Maisano et al. |
| 8,961,595 B2 | 2/2015 | Alkhatib |
| 8,961,596 B2 | 2/2015 | Maisano et al. |
| 8,968,335 B2 | 3/2015 | Robinson et al. |
| 8,968,336 B2 | 3/2015 | Conklin et al. |
| 8,968,395 B2 | 3/2015 | Hauser et al. |
| 8,979,922 B2 | 3/2015 | Jayasinghe et al. |
| 8,979,923 B2 | 3/2015 | Spence et al. |
| 9,005,273 B2 | 4/2015 | Salahieh et al. |
| 9,011,468 B2 | 4/2015 | Ketai et al. |
| 9,017,347 B2 | 4/2015 | Oba et al. |
| 9,034,032 B2 | 5/2015 | McLean et al. |
| 9,034,033 B2 | 5/2015 | McLean et al. |
| 9,078,652 B2 | 7/2015 | Conklin et al. |
| 9,084,676 B2 | 7/2015 | Chau et al. |
| 9,107,749 B2 | 8/2015 | Bobo et al. |
| 9,131,939 B1 | 9/2015 | Call et al. |
| 9,138,335 B2 | 9/2015 | Cartledge et al. |
| 9,180,005 B1 | 11/2015 | Lashinski et al. |
| 9,192,471 B2 | 11/2015 | Bolling |
| 9,211,203 B2 | 12/2015 | Pike et al. |
| 9,241,702 B2 | 1/2016 | Maisano et al. |
| 9,241,706 B2 | 1/2016 | Paraschac et al. |
| 9,259,218 B2 | 2/2016 | Robinson |
| 9,259,317 B2 | 2/2016 | Wilson et al. |
| 9,282,965 B2 | 3/2016 | Kokish |
| 9,289,282 B2 | 3/2016 | Olson et al. |
| 9,289,297 B2 | 3/2016 | Wilson et al. |
| 9,301,749 B2 | 4/2016 | Rowe et al. |
| 9,314,242 B2 | 4/2016 | Bachman |
| 9,326,870 B2 | 5/2016 | Berglund et al. |
| 9,358,111 B2 | 6/2016 | Spence et al. |
| 9,408,607 B2 | 8/2016 | Cartledge et al. |
| 9,474,605 B2 | 10/2016 | Rowe et al. |
| 2002/0013571 A1 | 1/2002 | Goldfarb et al. |
| 2002/0032481 A1 | 5/2002 | Gabbay |
| 2002/0082625 A1 | 6/2002 | Huxel et al. |
| 2002/0107564 A1 | 8/2002 | Cox et al. |
| 2002/0151961 A1 | 10/2002 | Lashinski et al. |
| 2002/0156517 A1 | 10/2002 | Perouse |
| 2002/0177904 A1 | 11/2002 | Huxel et al. |
| 2003/0033003 A1 | 2/2003 | Harrison et al. |
| 2003/0057156 A1 | 3/2003 | Peterson et al. |

(56) References Cited

U.S. PATENT DOCUMENTS

| | | |
|---|---|---|
| 2003/0083742 A1 | 5/2003 | Spence et al. |
| 2003/0093096 A1 | 5/2003 | McGuckin, Jr. et al. |
| 2003/0167071 A1 | 9/2003 | Martin et al. |
| 2003/0229350 A1 | 12/2003 | Kay |
| 2003/0236568 A1 | 12/2003 | Hojeibane et al. |
| 2004/0117009 A1 | 6/2004 | Cali et al. |
| 2004/0133274 A1 | 7/2004 | Webler et al. |
| 2004/0172046 A1 | 9/2004 | Hlavka et al. |
| 2004/0181287 A1 | 9/2004 | Gellman |
| 2004/0186566 A1* | 9/2004 | Hindrichs ........ A61B 17/00234 623/2.37 |
| 2004/0193092 A1 | 9/2004 | Deal |
| 2004/0236419 A1 | 11/2004 | Milo |
| 2004/0260389 A1 | 12/2004 | Case et al. |
| 2005/0004668 A1 | 1/2005 | Aklog et al. |
| 2005/0016560 A1 | 1/2005 | Voughlohn |
| 2005/0021085 A1 | 1/2005 | Abrams et al. |
| 2005/0055089 A1 | 3/2005 | Macoviak et al. |
| 2005/0059997 A1 | 3/2005 | Bauman et al. |
| 2005/0075723 A1 | 4/2005 | Schroeder et al. |
| 2005/0080483 A1 | 4/2005 | Solem et al. |
| 2005/0090827 A1 | 4/2005 | Gedebou |
| 2005/0096666 A1 | 5/2005 | Gordon et al. |
| 2005/0107812 A1 | 5/2005 | Starksen et al. |
| 2005/0107871 A1 | 5/2005 | Realyvasquez et al. |
| 2005/0113900 A1 | 5/2005 | Shiroff et al. |
| 2005/0125077 A1 | 6/2005 | Harmon et al. |
| 2005/0137688 A1 | 6/2005 | Salahieh et al. |
| 2005/0137695 A1 | 6/2005 | Salahieh et al. |
| 2005/0154448 A1 | 7/2005 | Cully et al. |
| 2005/0177180 A1 | 8/2005 | Kaganov et al. |
| 2005/0177228 A1 | 8/2005 | Solem |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Arayani |
| 2005/0251208 A1 | 11/2005 | Elmer et al. |
| 2005/0256532 A1 | 11/2005 | Nayak et al. |
| 2005/0273138 A1 | 12/2005 | To et al. |
| 2005/0283246 A1 | 12/2005 | Cauthen et al. |
| 2006/0004442 A1 | 1/2006 | Spenser et al. |
| 2006/0020326 A9 | 1/2006 | Bolduc et al. |
| 2006/0020327 A1 | 1/2006 | Lashinski et al. |
| 2006/0052821 A1 | 3/2006 | Abbot et al. |
| 2006/0106420 A1 | 5/2006 | Dolan et al. |
| 2006/0106423 A1 | 5/2006 | Weisel et al. |
| 2006/0129166 A1 | 6/2006 | Lavelle |
| 2006/0161265 A1 | 7/2006 | Levine et al. |
| 2006/0173524 A1 | 8/2006 | Salahieh et al. |
| 2006/0178700 A1 | 8/2006 | Quinn |
| 2006/0200199 A1 | 9/2006 | Bonutti et al. |
| 2006/0206201 A1 | 9/2006 | Garcia et al. |
| 2006/0229708 A1 | 10/2006 | Powell et al. |
| 2006/0241745 A1 | 10/2006 | Solem |
| 2006/0241748 A1 | 10/2006 | Lee et al. |
| 2006/0259135 A1 | 11/2006 | Navia et al. |
| 2006/0259137 A1 | 11/2006 | Artof et al. |
| 2006/0276871 A1 | 12/2006 | Lamson et al. |
| 2006/0282161 A1 | 12/2006 | Huynh et al. |
| 2007/0016287 A1 | 1/2007 | Cartledge |
| 2007/0016288 A1 | 1/2007 | Gurskis |
| 2007/0021781 A1 | 1/2007 | Jervis et al. |
| 2007/0032787 A1 | 2/2007 | Hassett et al. |
| 2007/0038221 A1 | 2/2007 | Fine et al. |
| 2007/0038296 A1 | 2/2007 | Navia |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055340 A1 | 3/2007 | Pryor |
| 2007/0060895 A1 | 3/2007 | Sibbitt et al. |
| 2007/0060989 A1 | 3/2007 | Deem et al. |
| 2007/0061010 A1 | 3/2007 | Hauser et al. |
| 2007/0066863 A1 | 3/2007 | Rafiee et al. |
| 2007/0083168 A1 | 4/2007 | Whiting et al. |
| 2007/0093869 A1 | 4/2007 | Bloom et al. |
| 2007/0100427 A1 | 5/2007 | Perouse |
| 2007/0112425 A1 | 5/2007 | Schaller et al. |
| 2007/0118151 A1 | 5/2007 | Davidson |
| 2007/0123936 A1 | 5/2007 | Goldin et al. |
| 2007/0162107 A1 | 7/2007 | Haug et al. |
| 2007/0168013 A1 | 7/2007 | Douglas |
| 2007/0185532 A1 | 8/2007 | Stone et al. |
| 2007/0198082 A1 | 8/2007 | Kapadia et al. |
| 2007/0203391 A1 | 8/2007 | Bloom et al. |
| 2007/0208389 A1 | 9/2007 | Amundson et al. |
| 2007/0219558 A1 | 9/2007 | Deutsch |
| 2007/0250160 A1 | 10/2007 | Rafiee |
| 2007/0265700 A1 | 11/2007 | Eliasen et al. |
| 2007/0270943 A1 | 11/2007 | Solem et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0288086 A1 | 12/2007 | Kalmann et al. |
| 2007/0288089 A1 | 12/2007 | Gurskis et al. |
| 2008/0003539 A1 | 1/2008 | Lundgren |
| 2008/0015617 A1 | 1/2008 | Harari et al. |
| 2008/0027268 A1 | 1/2008 | Buckner et al. |
| 2008/0027446 A1 | 1/2008 | Stone et al. |
| 2008/0027483 A1 | 1/2008 | Cartledge |
| 2008/0035160 A1 | 2/2008 | Woodson et al. |
| 2008/0058866 A1 | 3/2008 | Young et al. |
| 2008/0077231 A1 | 3/2008 | Heringes et al. |
| 2008/0097595 A1 | 4/2008 | Gabbay |
| 2008/0125861 A1 | 5/2008 | Webler et al. |
| 2008/0140116 A1 | 6/2008 | Bonutti |
| 2008/0140188 A1 | 6/2008 | Randert et al. |
| 2008/0167714 A1 | 7/2008 | St. Goar |
| 2008/0190989 A1 | 8/2008 | Crews et al. |
| 2008/0262598 A1 | 10/2008 | Elmaleh |
| 2008/0262609 A1 | 10/2008 | Gross et al. |
| 2008/0275469 A1 | 11/2008 | Fanton et al. |
| 2008/0281411 A1 | 11/2008 | Berreklouw et al. |
| 2008/0288044 A1 | 11/2008 | Osborne |
| 2008/0288062 A1 | 11/2008 | Andrieu et al. |
| 2008/0300629 A1 | 12/2008 | Surti |
| 2009/0005863 A1 | 1/2009 | Goetz et al. |
| 2009/0043382 A1 | 2/2009 | Maurer et al. |
| 2009/0048668 A1 | 2/2009 | Wilson et al. |
| 2009/0082828 A1 | 3/2009 | Ostroff |
| 2009/0082847 A1 | 3/2009 | Zacharias et al. |
| 2009/0084386 A1 | 4/2009 | McClellan et al. |
| 2009/0099647 A1 | 4/2009 | Glimsdale et al. |
| 2009/0099649 A1 | 4/2009 | Chobotov et al. |
| 2009/0112052 A1 | 4/2009 | Lund et al. |
| 2009/0118776 A1 | 5/2009 | Kelsch et al. |
| 2009/0131849 A1 | 5/2009 | Maurer et al. |
| 2009/0132033 A1 | 5/2009 | Maurer et al. |
| 2009/0143808 A1 | 6/2009 | Houser |
| 2009/0149872 A1 | 6/2009 | Gross et al. |
| 2009/0171439 A1 | 7/2009 | Nissl |
| 2009/0216265 A1 | 8/2009 | DeVries |
| 2009/0240326 A1 | 9/2009 | Wilson et al. |
| 2009/0254103 A1 | 10/2009 | Deutsch et al. |
| 2009/0259307 A1 | 10/2009 | Gross et al. |
| 2009/0264991 A1 | 10/2009 | Paul et al. |
| 2009/0264995 A1 | 10/2009 | Subramanian |
| 2009/0276040 A1 | 11/2009 | Rowe et al. |
| 2009/0287304 A1 | 11/2009 | Dahlgren et al. |
| 2009/0306622 A1 | 12/2009 | Machold et al. |
| 2009/0326648 A1 | 12/2009 | Machold et al. |
| 2010/0022948 A1 | 1/2010 | Wilson et al. |
| 2010/0023117 A1 | 1/2010 | Yoganathan et al. |
| 2010/0023118 A1 | 1/2010 | Medlock et al. |
| 2010/0029071 A1 | 2/2010 | Russell et al. |
| 2010/0030329 A1 | 2/2010 | Frater |
| 2010/0049293 A1 | 2/2010 | Zukowski et al. |
| 2010/0063520 A1 | 3/2010 | Bilotti |
| 2010/0063542 A1 | 3/2010 | Van der Burg et al. |
| 2010/0063586 A1 | 3/2010 | Hasenkam et al. |
| 2010/0121349 A1 | 5/2010 | Meier et al. |
| 2010/0121434 A1 | 5/2010 | Paul et al. |
| 2010/0121435 A1 | 5/2010 | Subramanian et al. |
| 2010/0130992 A1 | 5/2010 | Machold et al. |
| 2010/0161041 A1 | 6/2010 | Maisano et al. |

(56) References Cited

U.S. PATENT DOCUMENTS

| | | |
|---|---|---|
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0168791 A1 | 7/2010 | Kassab |
| 2010/0174358 A1 | 7/2010 | Rabkin |
| 2010/0185278 A1 | 7/2010 | Schankereli |
| 2010/0204662 A1 | 8/2010 | Orlov et al. |
| 2010/0211166 A1 | 8/2010 | Miller et al. |
| 2010/0217382 A1 | 8/2010 | Chau et al. |
| 2010/0228269 A1 | 9/2010 | Garrison et al. |
| 2010/0234935 A1 | 9/2010 | Bashiri |
| 2010/0249908 A1 | 9/2010 | Chau et al. |
| 2010/0249920 A1 | 9/2010 | Bolling et al. |
| 2010/0264192 A1 | 10/2010 | Marczyk |
| 2010/0268204 A1 | 10/2010 | Tieu et al. |
| 2010/0280603 A1 | 11/2010 | Maisano et al. |
| 2010/0280604 A1 | 11/2010 | Zipory et al. |
| 2010/0280605 A1 | 11/2010 | Hammer et al. |
| 2010/0286628 A1 | 11/2010 | Gross |
| 2010/0286767 A1 | 11/2010 | Zipory et al. |
| 2010/0298930 A1 | 11/2010 | Orlov |
| 2010/0324598 A1 | 12/2010 | Anderson |
| 2010/0324668 A1 | 12/2010 | Maurer et al. |
| 2011/0004296 A1 | 1/2011 | Lutter et al. |
| 2011/0009818 A1 | 1/2011 | Goff |
| 2011/0011917 A1 | 1/2011 | Loulmet |
| 2011/0022164 A1 | 1/2011 | Quinn et al. |
| 2011/0029066 A1 | 2/2011 | Gilad |
| 2011/0029071 A1 | 2/2011 | Zlotnick et al. |
| 2011/0035000 A1 | 2/2011 | Nieminen et al. |
| 2011/0040366 A1 | 2/2011 | Goetz et al. |
| 2011/0071626 A1 | 3/2011 | Wright et al. |
| 2011/0077733 A1 | 3/2011 | Solem |
| 2011/0082538 A1 | 4/2011 | Dahlgren et al. |
| 2011/0087146 A1 | 4/2011 | Ryan et al. |
| 2011/0092993 A1 | 4/2011 | Jacobs |
| 2011/0093002 A1 | 4/2011 | Rucker et al. |
| 2011/0098732 A1 | 4/2011 | Jacobs |
| 2011/0106245 A1 | 5/2011 | Miller et al. |
| 2011/0106247 A1 | 5/2011 | Miller et al. |
| 2011/0112619 A1 | 5/2011 | Foster et al. |
| 2011/0112632 A1 | 5/2011 | Chau et al. |
| 2011/0137397 A1 | 6/2011 | Chau et al. |
| 2011/0152998 A1 | 6/2011 | Berez et al. |
| 2011/0166636 A1 | 7/2011 | Rowe |
| 2011/0184510 A1* | 7/2011 | Maisano ............ A61B 17/0401 623/1.24 |
| 2011/0190879 A1 | 8/2011 | Bobo et al. |
| 2011/0208283 A1 | 8/2011 | Rust et al. |
| 2011/0224785 A1 | 9/2011 | Hacohen |
| 2011/0238088 A1 | 9/2011 | Bolduc et al. |
| 2011/0238112 A1 | 9/2011 | Kim et al. |
| 2011/0251678 A1 | 10/2011 | Eidenschink |
| 2011/0264208 A1 | 10/2011 | Duffy et al. |
| 2011/0301698 A1 | 12/2011 | Miller et al. |
| 2012/0016343 A1 | 1/2012 | Gill |
| 2012/0022633 A1 | 1/2012 | Olson et al. |
| 2012/0022639 A1 | 1/2012 | Hacohen et al. |
| 2012/0022640 A1 | 1/2012 | Gross et al. |
| 2012/0143320 A1 | 1/2012 | Eliasen et al. |
| 2012/0035712 A1 | 2/2012 | Maisano |
| 2012/0083806 A1 | 4/2012 | Goertzen |
| 2012/0123531 A1 | 5/2012 | Tsukashima et al. |
| 2012/0130374 A1 | 5/2012 | Bouduban et al. |
| 2012/0130421 A1 | 5/2012 | Hafez et al. |
| 2012/0158053 A1 | 6/2012 | Paulos |
| 2012/0179244 A1 | 7/2012 | Schankereli et al. |
| 2012/0215236 A1 | 8/2012 | Matsunaga et al. |
| 2012/0222969 A1 | 9/2012 | Osborne et al. |
| 2012/0226349 A1 | 9/2012 | Tuval et al. |
| 2012/0232373 A1 | 9/2012 | Hallander et al. |
| 2012/0245604 A1 | 9/2012 | Tegzes |
| 2012/0283757 A1 | 11/2012 | Miller et al. |
| 2012/0296349 A1 | 11/2012 | Smith et al. |
| 2012/0310328 A1 | 12/2012 | Olson et al. |
| 2013/0030522 A1 | 1/2013 | Rowe et al. |
| 2013/0041459 A1 | 2/2013 | Wilson et al. |
| 2013/0053951 A1 | 2/2013 | Baliarda |
| 2013/0085529 A1 | 4/2013 | Housman |
| 2013/0096664 A1 | 4/2013 | Goetz et al. |
| 2013/0096672 A1 | 4/2013 | Reich et al. |
| 2013/0110230 A1 | 5/2013 | Solem |
| 2013/0166017 A1 | 6/2013 | Cartledge et al. |
| 2013/0166022 A1 | 6/2013 | Conklin |
| 2013/0172978 A1 | 7/2013 | Vidlund et al. |
| 2013/0233324 A1 | 9/2013 | Witt et al. |
| 2013/0281760 A1 | 10/2013 | Farnan et al. |
| 2013/0296925 A1 | 11/2013 | Chanduszko et al. |
| 2013/0325110 A1 | 12/2013 | Khalil et al. |
| 2013/0331930 A1 | 12/2013 | Rowe et al. |
| 2014/0005778 A1 | 1/2014 | Buchbinder et al. |
| 2014/0018911 A1 | 1/2014 | Zhou et al. |
| 2014/0031864 A1 | 1/2014 | Jafari et al. |
| 2014/0031928 A1 | 1/2014 | Murphy et al. |
| 2014/0058405 A1 | 2/2014 | Foster |
| 2014/0066693 A1 | 3/2014 | Goldfarb et al. |
| 2014/0067054 A1 | 3/2014 | Chau et al. |
| 2014/0114390 A1 | 4/2014 | Tobis et al. |
| 2014/0121763 A1 | 5/2014 | Duffy et al. |
| 2014/0142689 A1 | 5/2014 | De Canniere et al. |
| 2014/0163690 A1 | 6/2014 | White |
| 2014/0200657 A1 | 7/2014 | Maurer et al. |
| 2014/0207231 A1 | 7/2014 | Hacohen et al. |
| 2014/0214159 A1 | 7/2014 | Vidlund et al. |
| 2014/0243894 A1 | 8/2014 | Groothuis et al. |
| 2014/0257475 A1 | 9/2014 | Gross et al. |
| 2014/0275757 A1 | 9/2014 | Goodwin et al. |
| 2014/0277390 A1 | 9/2014 | Ratz et al. |
| 2014/0277427 A1 | 9/2014 | Ratz et al. |
| 2014/0288639 A1 | 9/2014 | Gainor |
| 2014/0296962 A1 | 10/2014 | Cartledge et al. |
| 2014/0309730 A1 | 10/2014 | Alon et al. |
| 2014/0324164 A1 | 10/2014 | Gross et al. |
| 2014/0358224 A1 | 12/2014 | Tegels et al. |
| 2014/0371843 A1 | 12/2014 | Wilson et al. |
| 2014/0379006 A1 | 12/2014 | Sutherland et al. |
| 2014/0379074 A1 | 12/2014 | Spence et al. |
| 2014/0379076 A1 | 12/2014 | Vidlund et al. |
| 2015/0018940 A1 | 1/2015 | Quill et al. |
| 2015/0045879 A1 | 2/2015 | Longoria et al. |
| 2015/0051698 A1 | 2/2015 | Baliarda et al. |
| 2015/0066138 A1 | 3/2015 | Alexander et al. |
| 2015/0073545 A1 | 3/2015 | Braido |
| 2015/0094800 A1 | 4/2015 | Chawla |
| 2015/0094802 A1 | 4/2015 | Buchbinder et al. |
| 2015/0100116 A1 | 4/2015 | Mohl et al. |
| 2015/0119936 A1 | 4/2015 | Gilmore et al. |
| 2015/0127097 A1 | 5/2015 | Neumann et al. |
| 2015/0142049 A1 | 5/2015 | Delgado et al. |
| 2015/0142103 A1 | 5/2015 | Vidlund |
| 2015/0142105 A1 | 5/2015 | Bolling et al. |
| 2015/0182336 A1 | 7/2015 | Zipory et al. |
| 2015/0196693 A1 | 7/2015 | Lin |
| 2015/0223934 A1 | 8/2015 | Vidlund et al. |
| 2015/0250590 A1 | 9/2015 | Gries et al. |
| 2015/0272730 A1 | 10/2015 | Melnick et al. |
| 2015/0320414 A1 | 11/2015 | Conklin et al. |
| 2015/0351909 A1 | 12/2015 | Bobo et al. |
| 2015/0351910 A1 | 12/2015 | Gilmore et al. |
| 2016/0022417 A1 | 1/2016 | Karapetian et al. |
| 2016/0038285 A1 | 2/2016 | Glenn et al. |
| 2016/0081829 A1 | 3/2016 | Rowe |
| 2016/0120672 A1 | 5/2016 | Martin et al. |
| 2016/0128689 A1 | 5/2016 | Sutherland et al. |
| 2016/0157862 A1 | 6/2016 | Hernandez et al. |
| 2016/0174979 A1 | 6/2016 | Wei |
| 2016/0228246 A1 | 8/2016 | Zimmerman |
| 2016/0228252 A1 | 8/2016 | Keidar |
| 2016/0235526 A1 | 8/2016 | Lashinski et al. |
| 2016/0235533 A1 | 8/2016 | Gilmore et al. |
| 2016/0242762 A1 | 8/2016 | Gilmore et al. |
| 2016/0256269 A1 | 9/2016 | Cahalane et al. |
| 2016/0262741 A1 | 9/2016 | Gilmore et al. |
| 2016/0270776 A1 | 9/2016 | Miraki et al. |

(56) References Cited

U.S. PATENT DOCUMENTS

| | | |
|---|---|---|
| 2016/0270916 A1 | 9/2016 | Cahalane et al. |
| 2016/0287383 A1 | 10/2016 | Rowe |
| 2016/0287387 A1 | 10/2016 | Wei |

FOREIGN PATENT DOCUMENTS

| | | |
|---|---|---|
| EP | 1397176 | 3/2007 |
| EP | 1759663 | 3/2007 |
| EP | 1 836 971 | 9/2007 |
| EP | 1562522 | 12/2008 |
| EP | 1357843 | 5/2009 |
| EP | 1 968 491 | 7/2010 |
| EP | 1928357 | 11/2010 |
| EP | 1718249 | 4/2011 |
| EP | 2399549 | 3/2014 |
| EP | 1646332 | 6/2015 |
| EP | 2410948 | 7/2016 |
| EP | 2465568 | 8/2016 |
| EP | 2023858 | 10/2016 |
| WO | 1992/005093 | 4/1992 |
| WO | 1997/041778 | 11/1997 |
| WO | 2000/28923 | 5/2000 |
| WO | 2001/010306 | 2/2001 |
| WO | 2004/069055 | 8/2004 |
| WO | 2004/082538 | 9/2004 |
| WO | 2005/021063 | 3/2005 |
| WO | 2005/058206 | 6/2005 |
| WO | 2005/102194 | 11/2005 |
| WO | 2006/019498 | 2/2006 |
| WO | 2006/097931 | 9/2006 |
| WO | 2006/105008 | 10/2006 |
| WO | 2006/105009 | 10/2006 |
| WO | 2007/080595 | 7/2007 |
| WO | 2007/140309 | 12/2007 |
| WO | 2008/065044 | 6/2008 |
| WO | 2008/068756 | 6/2008 |
| WO | 2009/039400 | 3/2009 |
| WO | 2009/101617 | 8/2009 |
| WO | 2010/004546 | 1/2010 |
| WO | 2010/008549 | 1/2010 |
| WO | 2010/071494 | 6/2010 |
| WO | 2010/073246 | 7/2010 |
| WO | 2010/099032 | 9/2010 |
| WO | 2010/108079 | 9/2010 |
| WO | 2010/128502 | 11/2010 |
| WO | 2010/128503 | 11/2010 |
| WO | 2011/014496 | 2/2011 |
| WO | 2011/037891 | 3/2011 |
| WO | 2011/051942 | 5/2011 |
| WO | 2011/089601 | 7/2011 |
| WO | 2011/097355 | 8/2011 |
| WO | 2011/143263 | 11/2011 |
| WO | 2011/153408 | 12/2011 |
| WO | 2012/127309 | 9/2012 |
| WO | 2013/003228 | 1/2013 |
| WO | 2013/011502 | 1/2013 |
| WO | 2013/028145 | 2/2013 |
| WO | 2013/078497 | 6/2013 |
| WO | 2014/043527 | 3/2014 |
| WO | 2014/064694 | 5/2014 |
| WO | 2014/087402 | 6/2014 |
| WO | 2014/108903 | 7/2014 |
| WO | 2014/141239 | 9/2014 |
| WO | 2015/015497 | 2/2015 |
| WO | 2015/063580 | 5/2015 |
| WO | 2015/193728 | 12/2015 |
| WO | 2016/011275 | 1/2016 |
| WO | 2016/087934 | 6/2016 |

OTHER PUBLICATIONS

An International Search Report 2013, which issued during and a Written Opinion both dated Dec. 6, 2013, which issued during the prosecution of Applicant's PCT/IL2013/050470.

U.S. Appl. No. 62/131,636, filed Mar. 11, 2015.
Alfieri et al., "An effective technique to correct anterior mitral leaflet prolapse," J Card Surg 14(6):468-470 (1999).
U.S. Appl. No. 62/014,397, filed Jun. 19, 2014.
Alfieri et al., "Novel suture device for beating heart mitral leaflet approximation," Annals of Thoracic Surgery 74:1488 1493 (2002).
Alfieri et al., "The double orifice technique in mitral valve repair: a simple solution for complex problems," Journal of Thoracic Cardiovascular Surgery 122:674-681 (2001).
Amplatzer Cardiac Plug Brochure (English Pages), AGA Medical Corporation, Plymouth, MN Copyright 2008-2011, downloaded Jan. 11, 2011.
Beale BS, "Surgical Repair of Collateral Ligament Injuries," presented at 63rd CVMA Convention, Halifax, Nova Scotia, Canada, Jul. 6-9, 2011.
Dentistry Today, "Implant Direct" product information page, Jun. 1, 2011, downloaded Dec. 10, 2012 from http://dentistrytoday.com/top25implant-i/5558-implant-direct.
Maisano et al., "The double-orifice technique as a standardized approach to treat mitral regurgitation due to severe myxomatous disease: surgical technique," European Journal of Cardio-thoracic Surgery 17 (2000) 201-205.
Shikhar Agarwal et al., "Interventional Cardiology Perspective of Functional Tricuspid Regurgitation," Circulatoin: Cardiovascular Interventions, pp. 565-573; Dec. 2009; vol. 2, Issue 6.
Smith & Nephew MINITAC™ TI 2.0 Suture Anchor Product Description, downloaded on Dec. 9, 2012 from http://global.smith-nephew.com/us/MINITAC_TI_2_SUTURE_ANCHR_3127.htm.
Second Notice of Allowance dated May 10, 2013, which issued during the prosecution of U.S. Appl. No. 12/692,061.
An Interview Summary dated Nov. 5, 2012, which issued during the prosecution of U.S. Appl. No. 12/692,061.
An Office Action dated Jul. 6, 2012, which issued during the prosecution of U.S. Appl. No. 12/692,061.
A Notice of Allowance dated Mar. 6, 2013, which issued during the prosecution of U.S. Appl. No. 12/692,061.
An International Search Report and a Written Opinion both dated May 19, 2011, which issued during the prosecution of Applicant's PCT/IL11/00064.
An International Search Report and a Written Opinion both dated Jan. 22, 2013, which issued during the prosecution of Applicant's PCT/IL2012/000282.
An Office Action dated Dec. 5, 2013, which issued during the prosecution of U.S. Appl. No. 13/485,145.
An International Search Report and a Written Opinion both dated Mar. 17, 2014, which issued during the prosecution of Applicant's PCT/IL2013/050937.
Invitation to pay additional fees in PCT/IL2014/050027 dated Apr. 4, 2014.
An International Search Report and a Written Opinion both dated May 28, 2014, which issued during the prosecution of Applicant's PCT/IL2014/050027.
U.S. Appl. No. 60/902,146, filed Feb. 16, 2007.
European Search Report dated Apr. 10, 2015, which issued during the prosecution of Applicant's European App No. 11734451.5.
European Search Report dated May 15, 2015, which issued during the prosecution of Applicant's European App No. 12814417.7.
An Office Action dated Sep. 14, 2015, which issued during the prosecution of U.S. Appl. No. 13/553,081.
An English Translation of an Office Action dated Jun. 30, 2015 which issued during the prosecution of Chinese Patent Application No. 201180015301.6.
An English Translation of an Office Action dated Jul. 7, 2015 which issued during the prosecution of Japanese Patent Application No. 2012-549463.
An Office Action dated Oct. 7, 2015, which issued during the prosecution of U.S. Appl. No. 13/574,088.
Invitation to Pay Additional Fees dated Apr. 20, 2015, which issued during the prosecution of Applicant's PCT/IB2014/002351.
An International Search Report and a Written Opinion both dated Jun. 10, 2015, which issued during the prosecution of Applicant's PCT/IB2014/002351.

(56) References Cited

OTHER PUBLICATIONS

An Office Action dated Feb. 2, 2015, which issued during the prosecution of U.S. Appl. No. 14/143,355.
An English Translation of an Office Action dated Feb. 10, 2015 which issued during the prosecution of Chinese Patent Application No. 201180015301.6.
An Office Action dated Feb. 25, 2015, which issued during the prosecution of U.S. Appl. No. 13/574,088.
Notice of Allowance dated Sep. 24, 2015, which issued during the prosecution of U.S. Appl. No. 14/143,355.
Notice of Allowance dated Dec. 4, 2015, which issued during the prosecution of U.S. Appl. No. 14/143,355.
An Office Action dated Jul. 7, 2014, which issued during the prosecution of U.S. Appl. No. 13/485,145.
An English Translation of an Office Action dated Jun. 30, 2014 which issued during the prosecution of Chinese Patent Application No. 201180015301.6.
An Office Action dated Sep. 25, 2014, which issued during the prosecution of U.S. Appl. No. 13/485,145.
An English Translation of an Office Action dated Oct. 28, 2014,which issued during the prosecution of Japanese Patent Application No. 2012-549463.
Notice of Allowance dated Dec. 9, 2014, which issued during the prosecution of U.S. Appl. No. 13/485,145.
An International Search Report and a Written Opinion both dated Jun. 30, 2014, which issued during the prosecution of Applicant's PCT/IL2014/050233.
An International Search Report and a Written Opinion both dated Jan. 8, 2016, 2014, which issued during the prosecution of Applicant's PCT/IB2015/001196.
Invitation to pay additional fees in PCT/IB2015/001196 dated Oct. 26, 2015.
Notice of Allowance dated Dec. 4, 2014, which issued during the prosecution of U.S. Appl. No. 13/188,175.
An Office Action dated Nov. 25, 2014, which issued during the prosecution of U.S. Appl. No. 13/553,081.
An Office Action dated Apr. 18, 2016, which issued during the prosecution of U.S. Appl. No. 14/584,286.
Spinal & Epidural Needles—downloaded on Feb. 18, 2016 from http://www.cothon.net/Anestesia_Obstetrica/Neuroaxial_needles.html.
An Office Action dated May 11, 2016, which issued during the prosecution of U.S. Appl. No. 13/574,088.
An International Search Report and a Written Opinion both dated Apr. 15, 2016, 2014, which issued during the prosecution of Applicant's PCT/IB2015/002354.
U.S. Appl. No. 62/167,660, filed May 28, 2015.
An English Translation of an Office Action dated Jun. 23, 2016 which issued during the prosecution of Chinese Patent Application No. 201480028044.3. (the relevant part only).
U.S. Appl. No. 62/086,269, filed Dec. 2, 2014.
Notice of Allowance dated Sep. 5, 2016, which issued during the prosecution of Chinese Patent Application No. 2014800280443.
An Office Action dated Sep. 14, 2016, which issued during the prosecution of U.S. Appl. No. 13/574,088.
Invitation to pay additional fees in PCT/IB2016/000840 dated Oct. 13, 2016.
U.S. Appl. No. 61/750,427, filed Jan. 9, 2013.
U.S. Appl. No. 61/897,509, filed Oct. 30, 2013.

\* cited by examiner

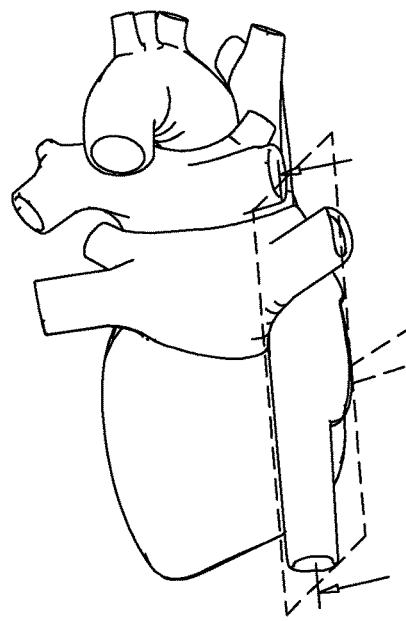
FIG. 3A
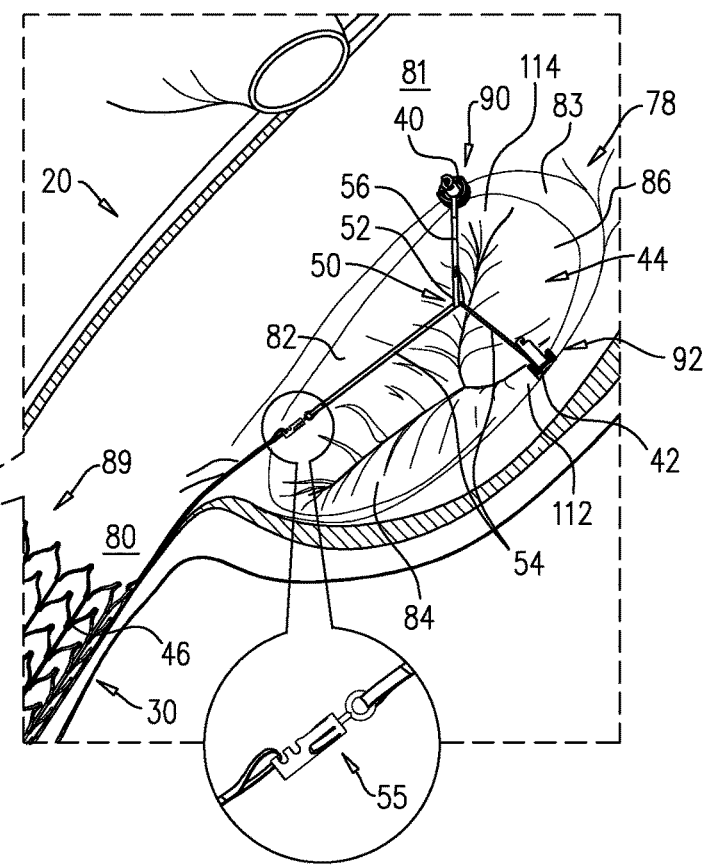
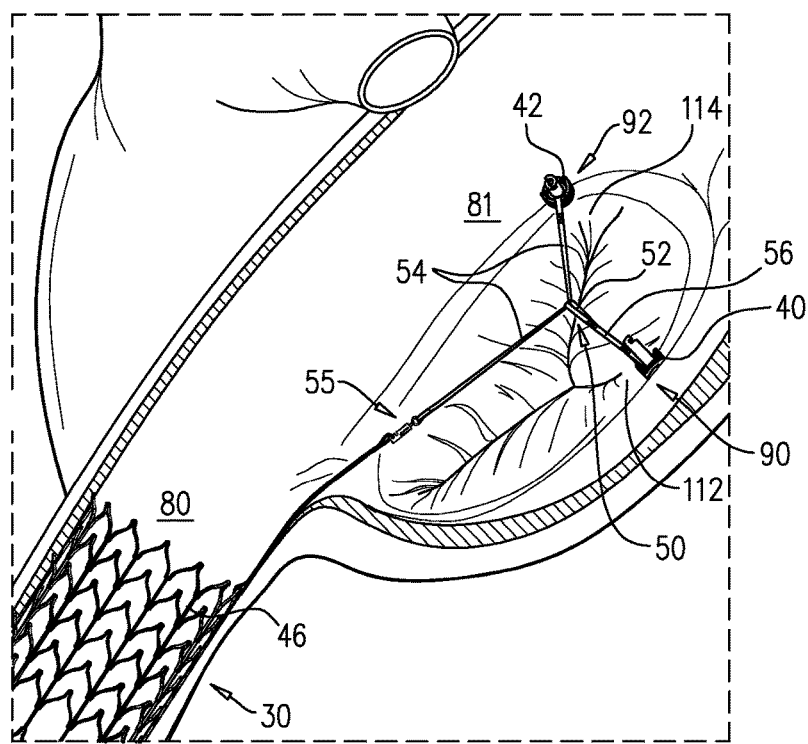
FIG. 3B

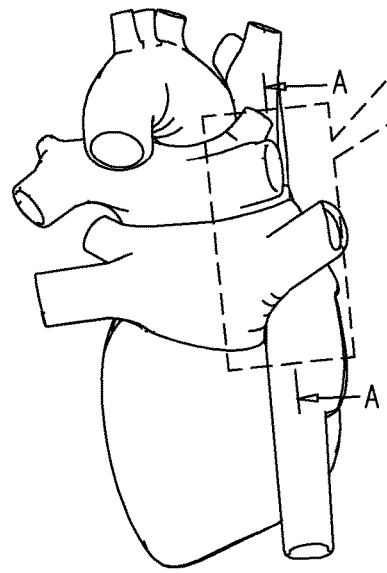
FIG. 3G
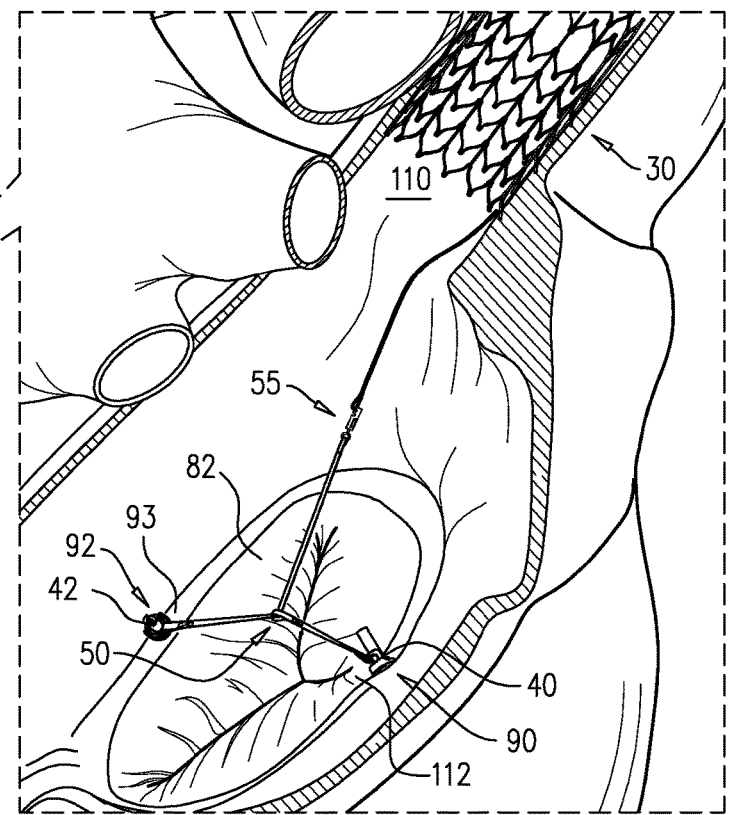
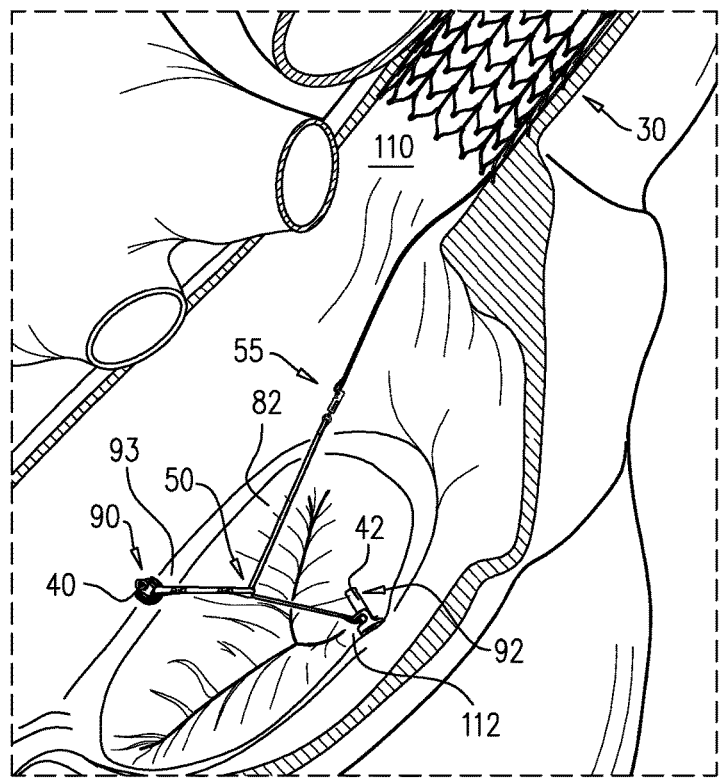
FIG. 3H

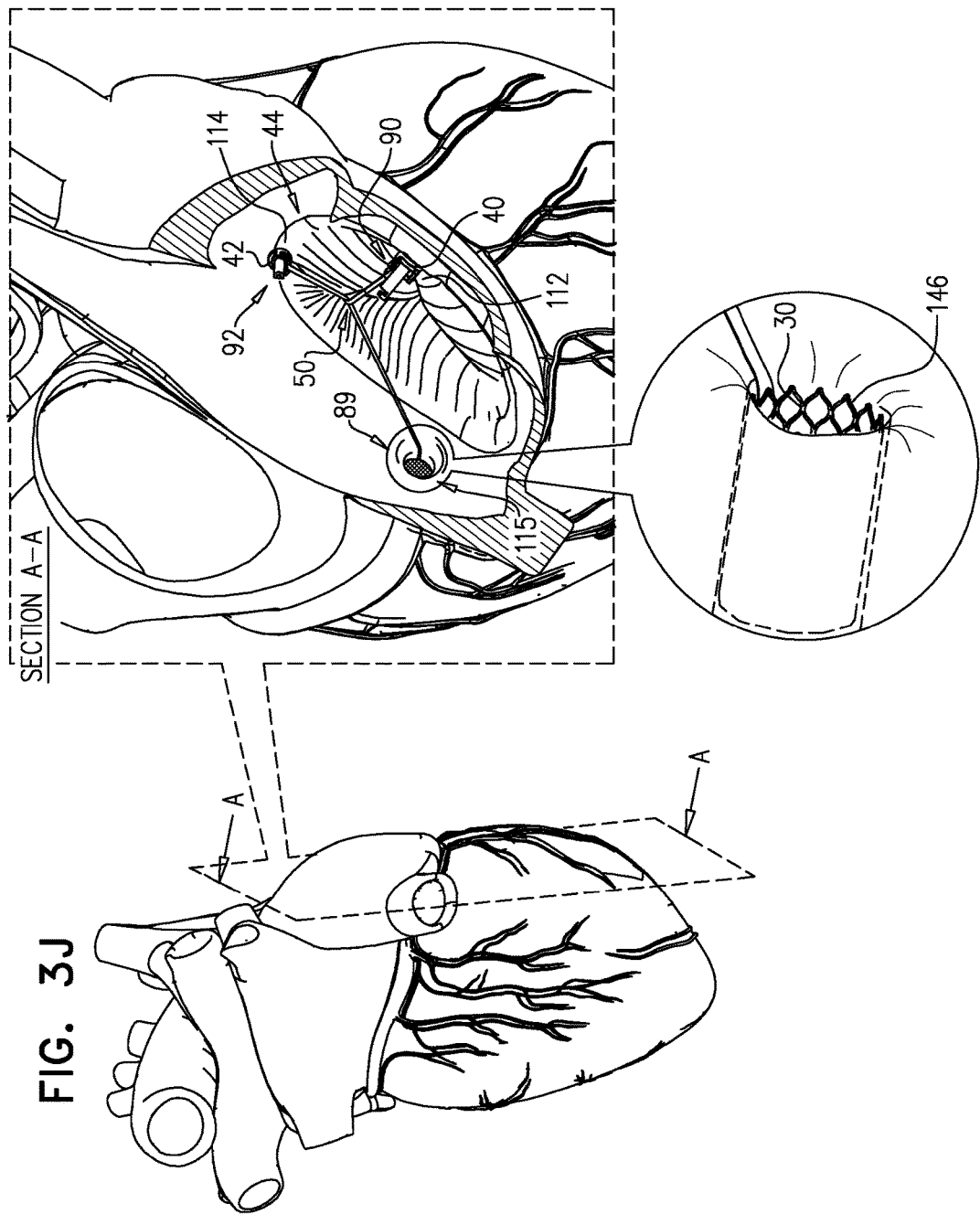

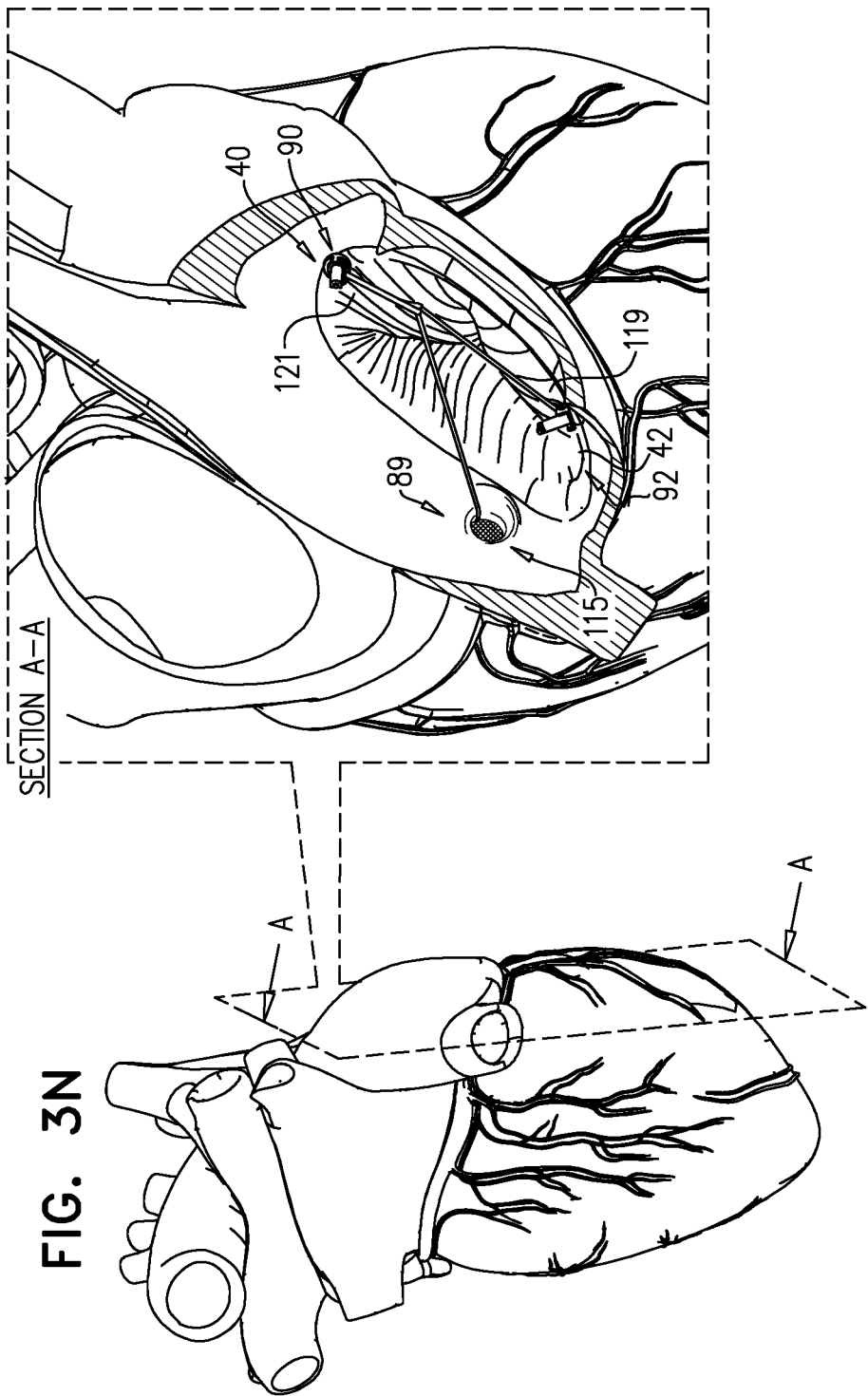

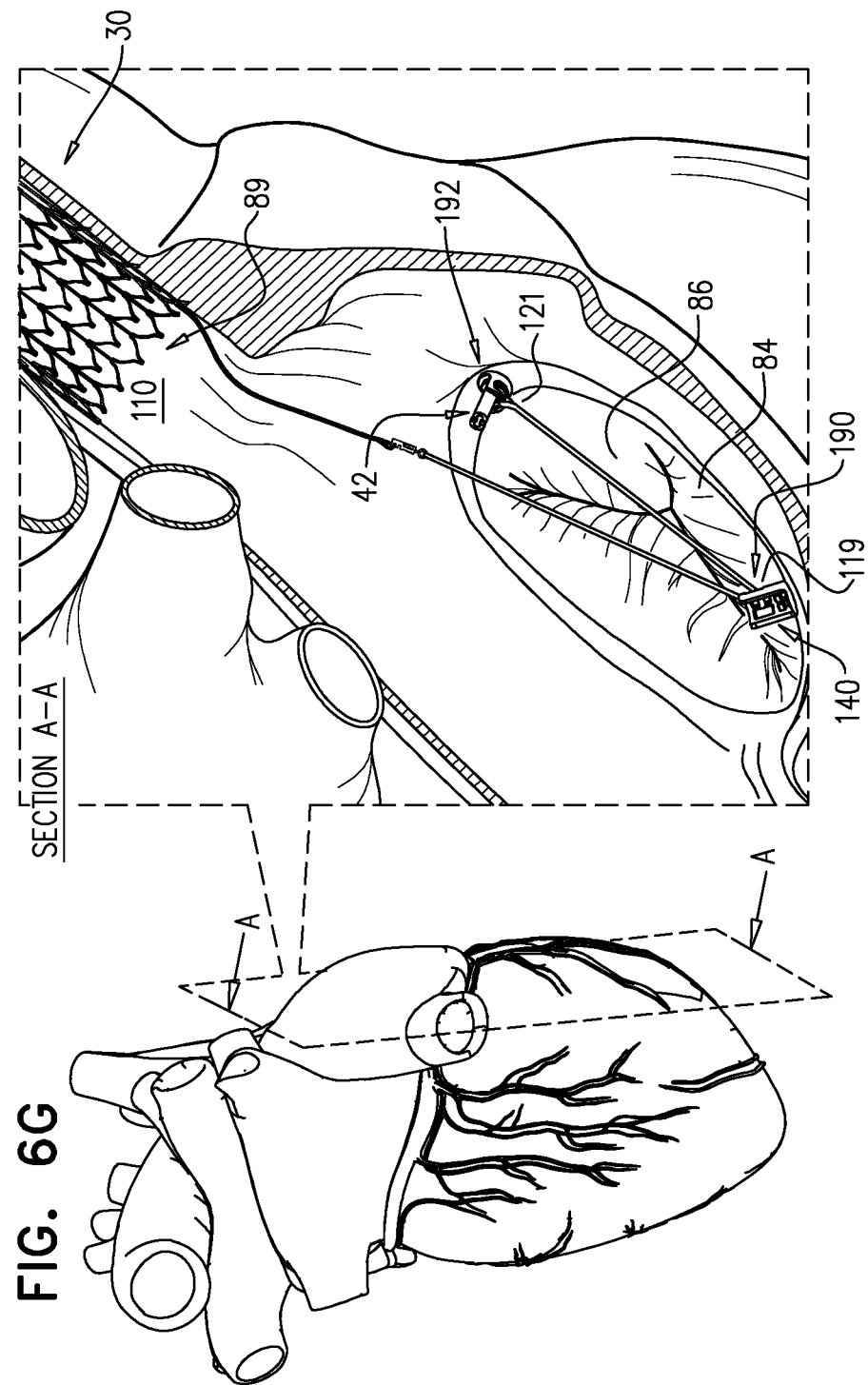

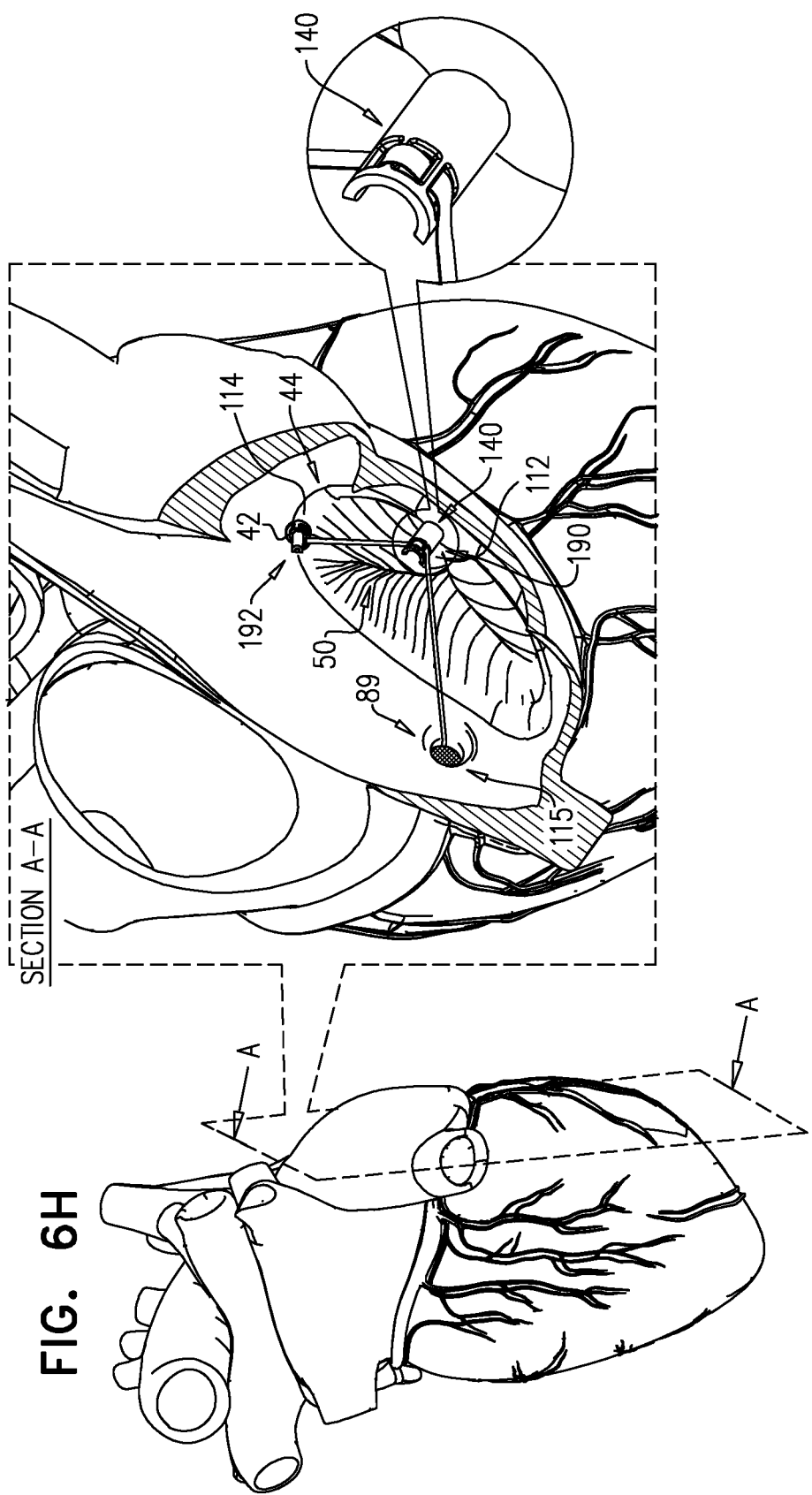

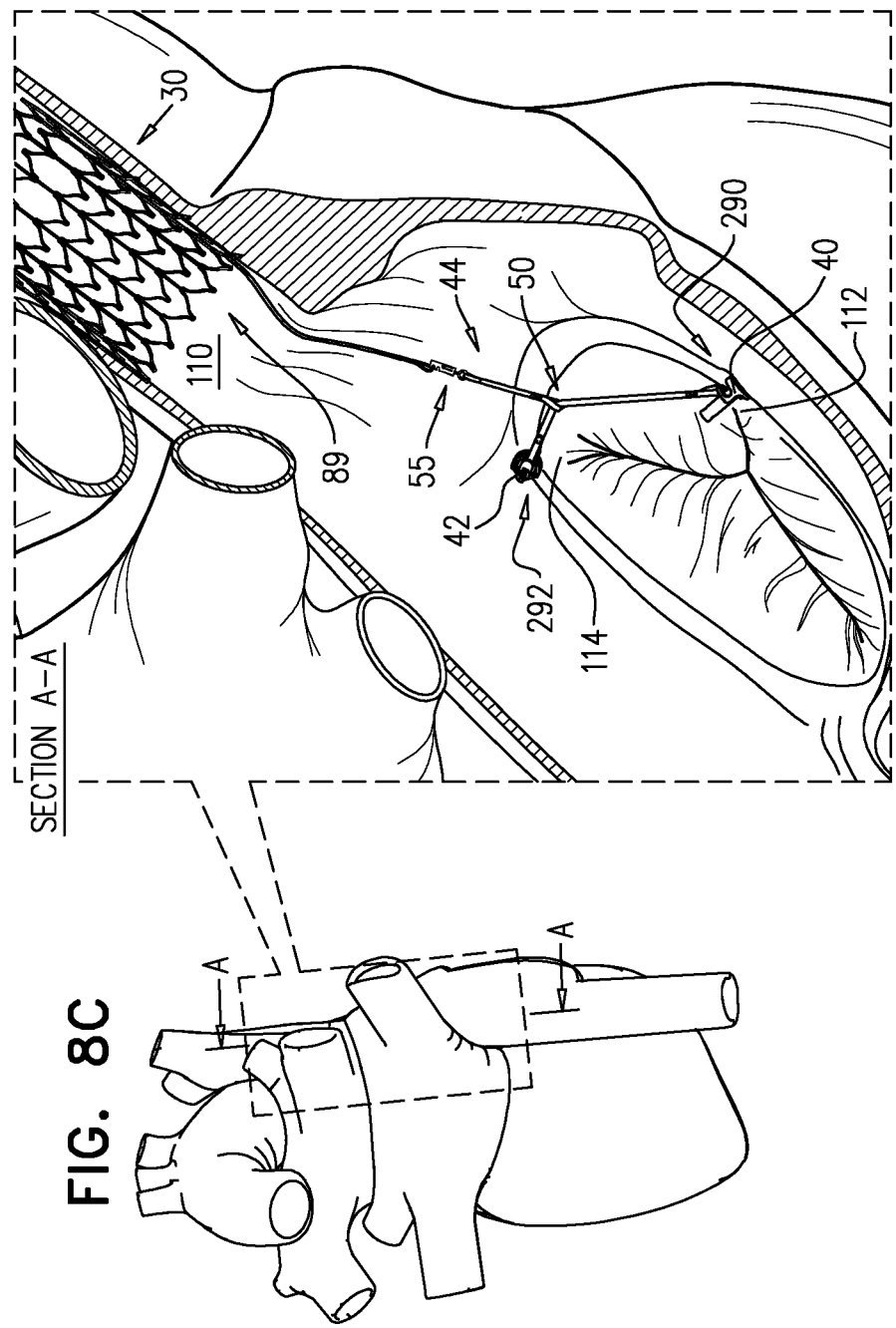

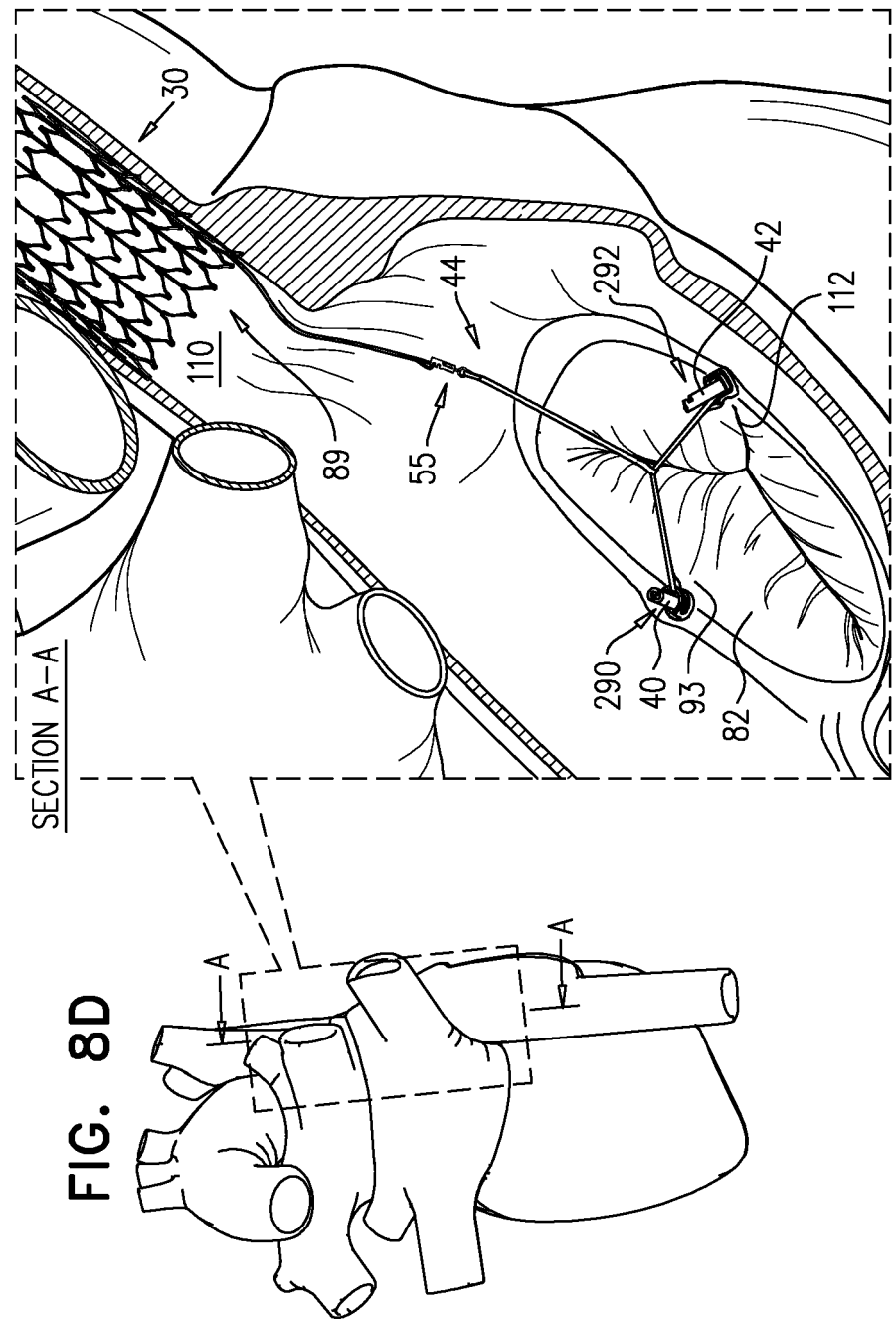

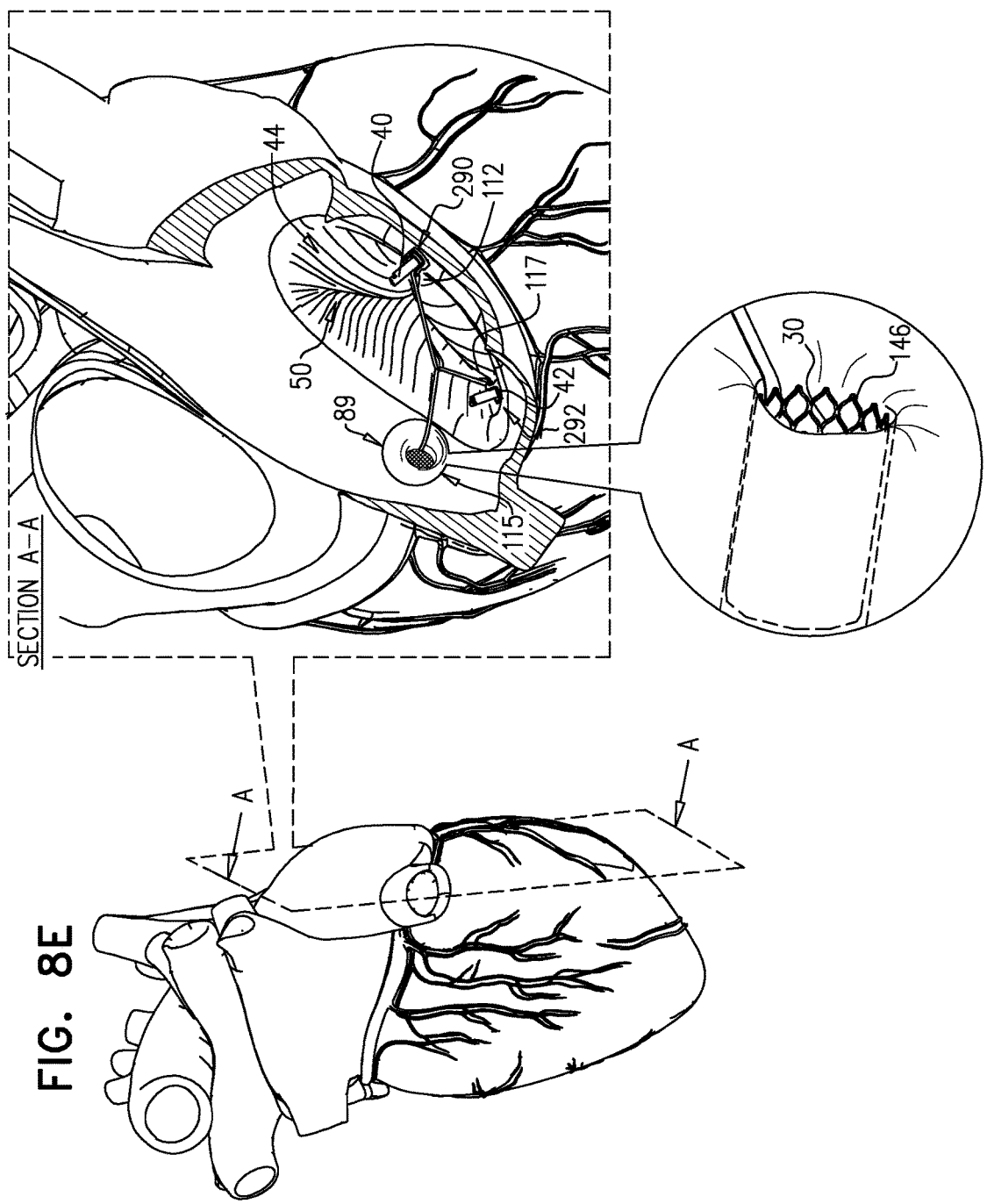

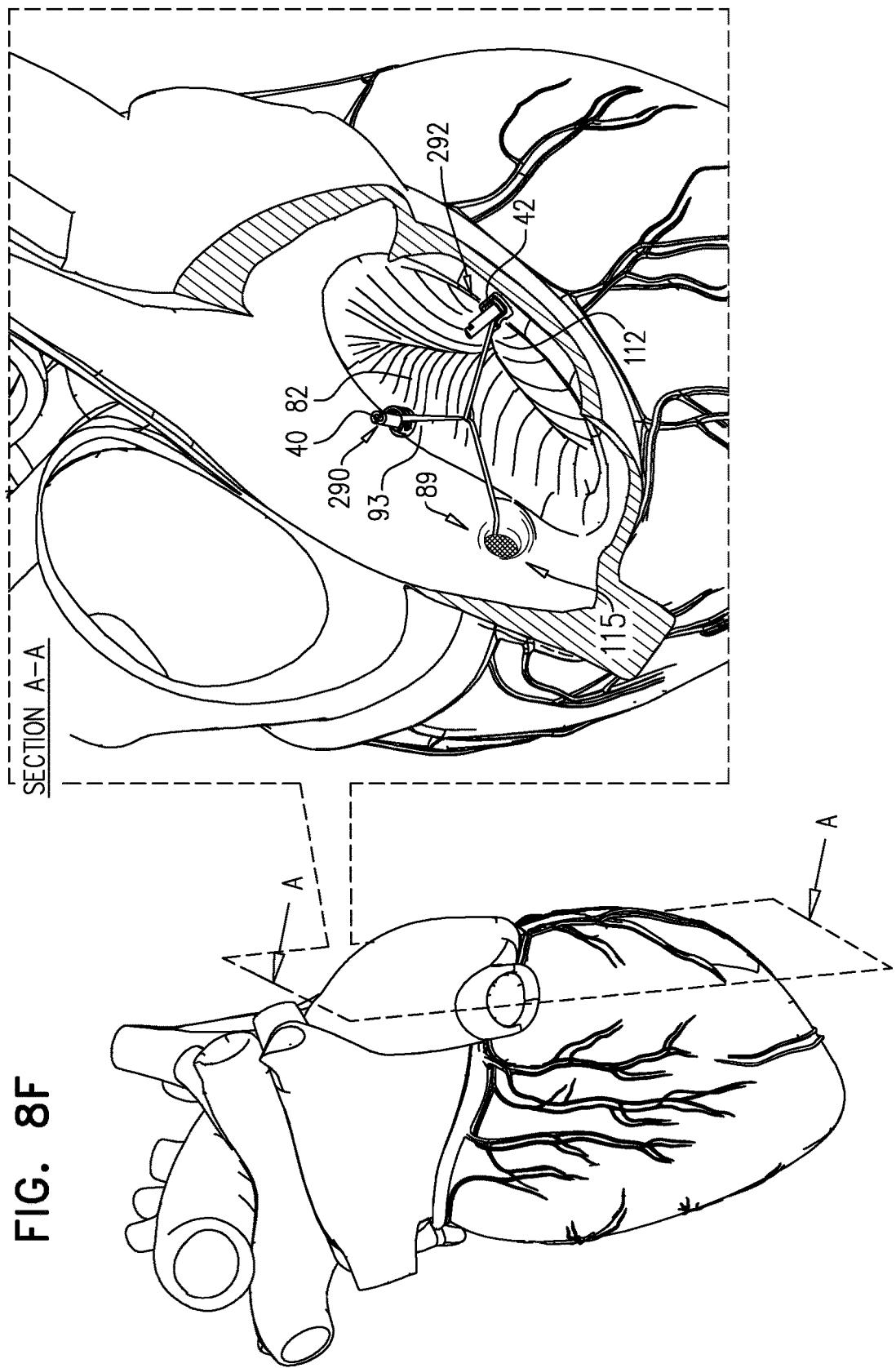

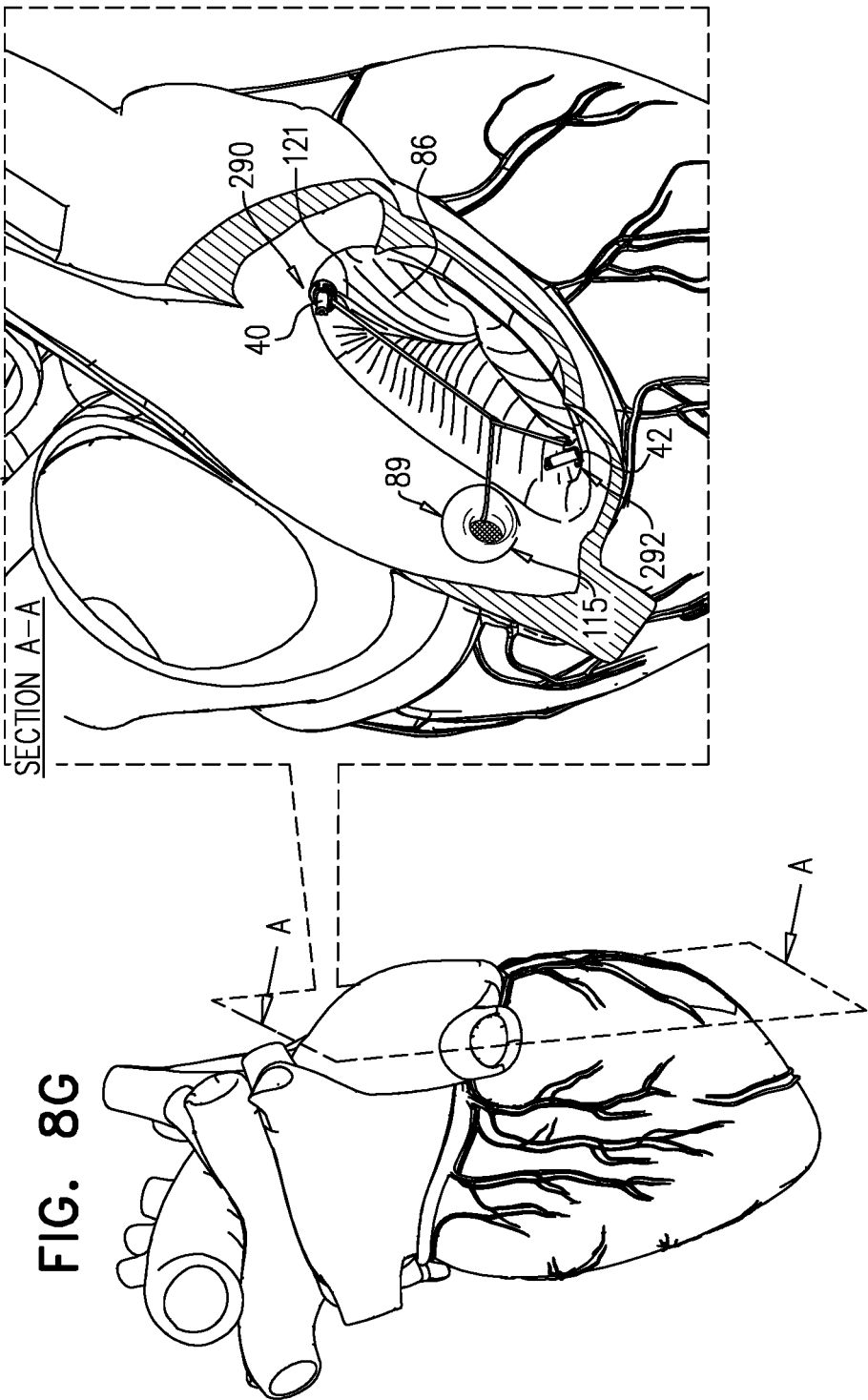

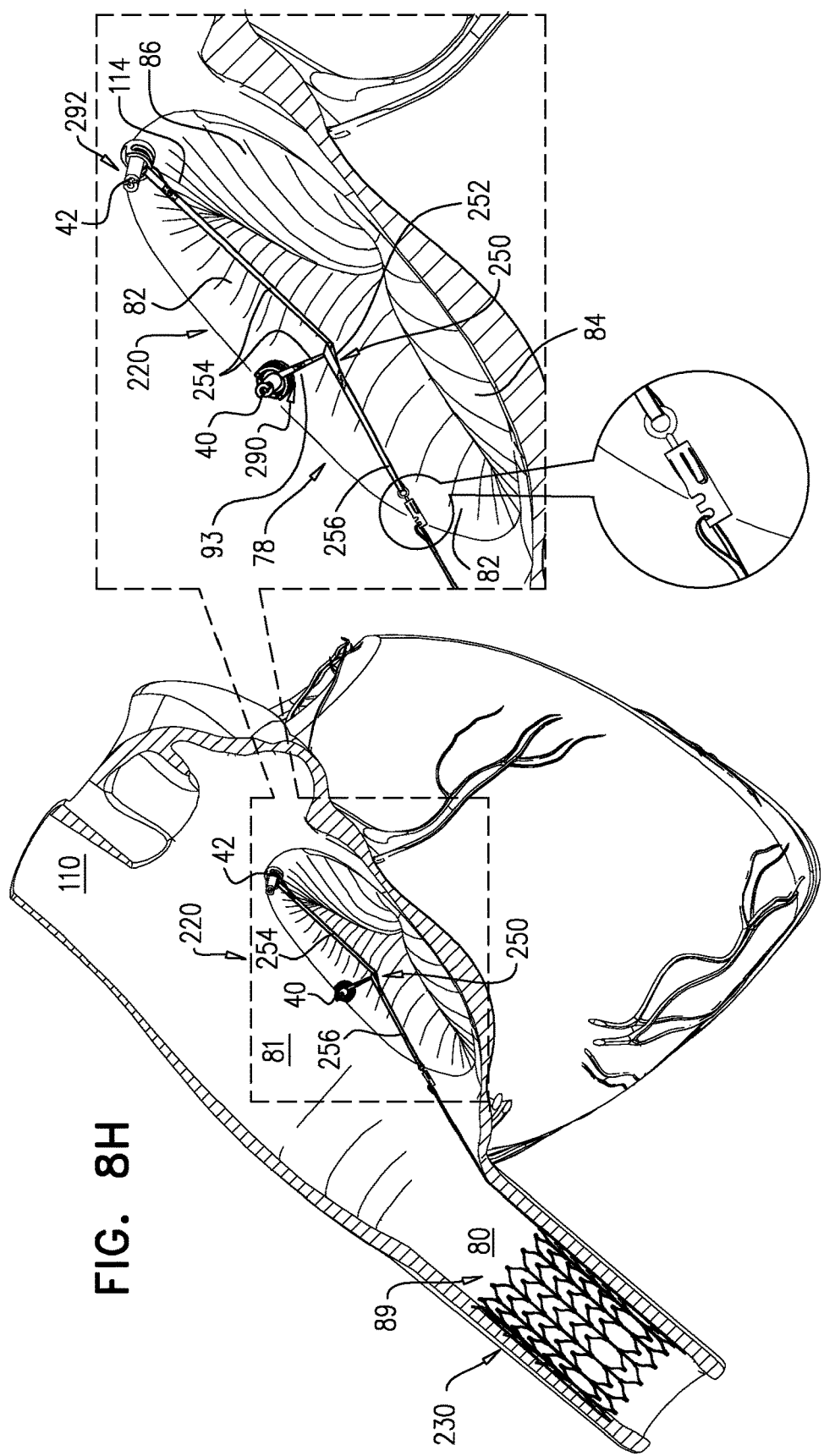

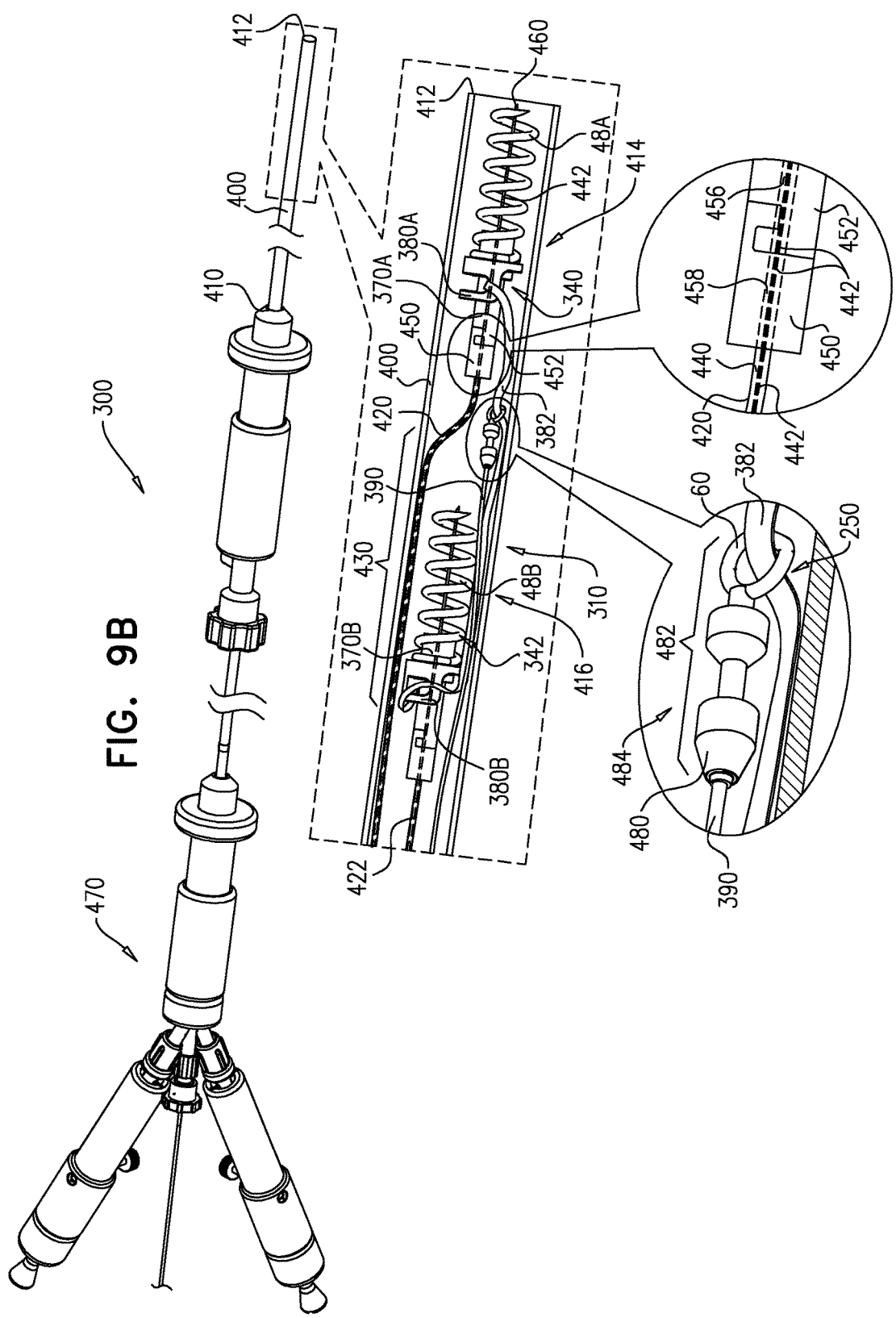

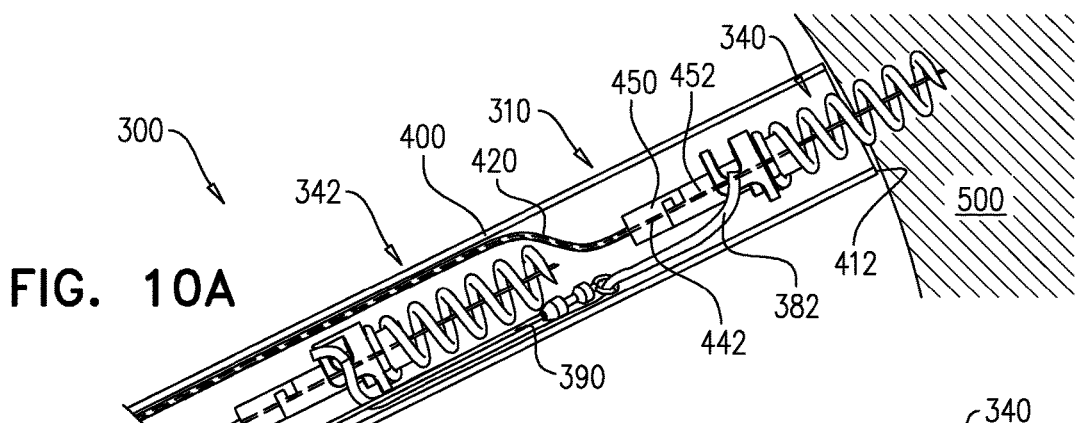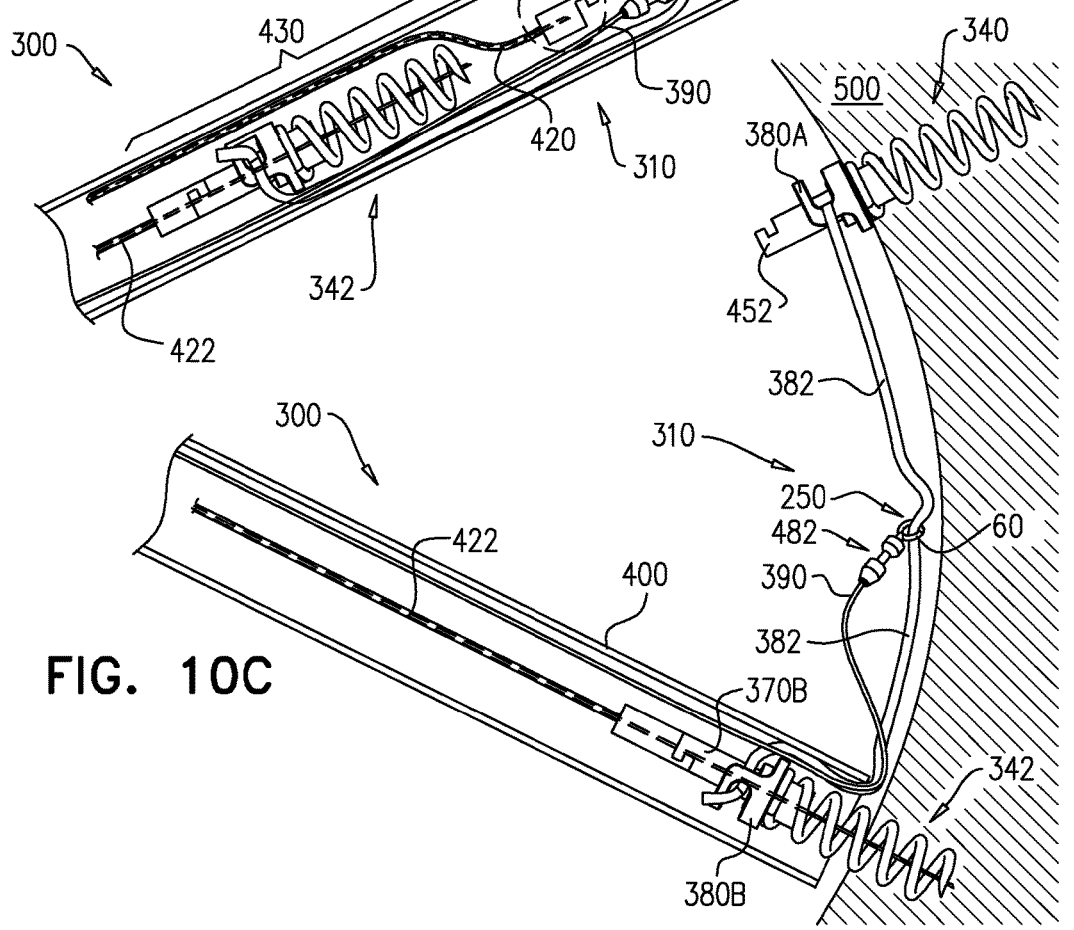

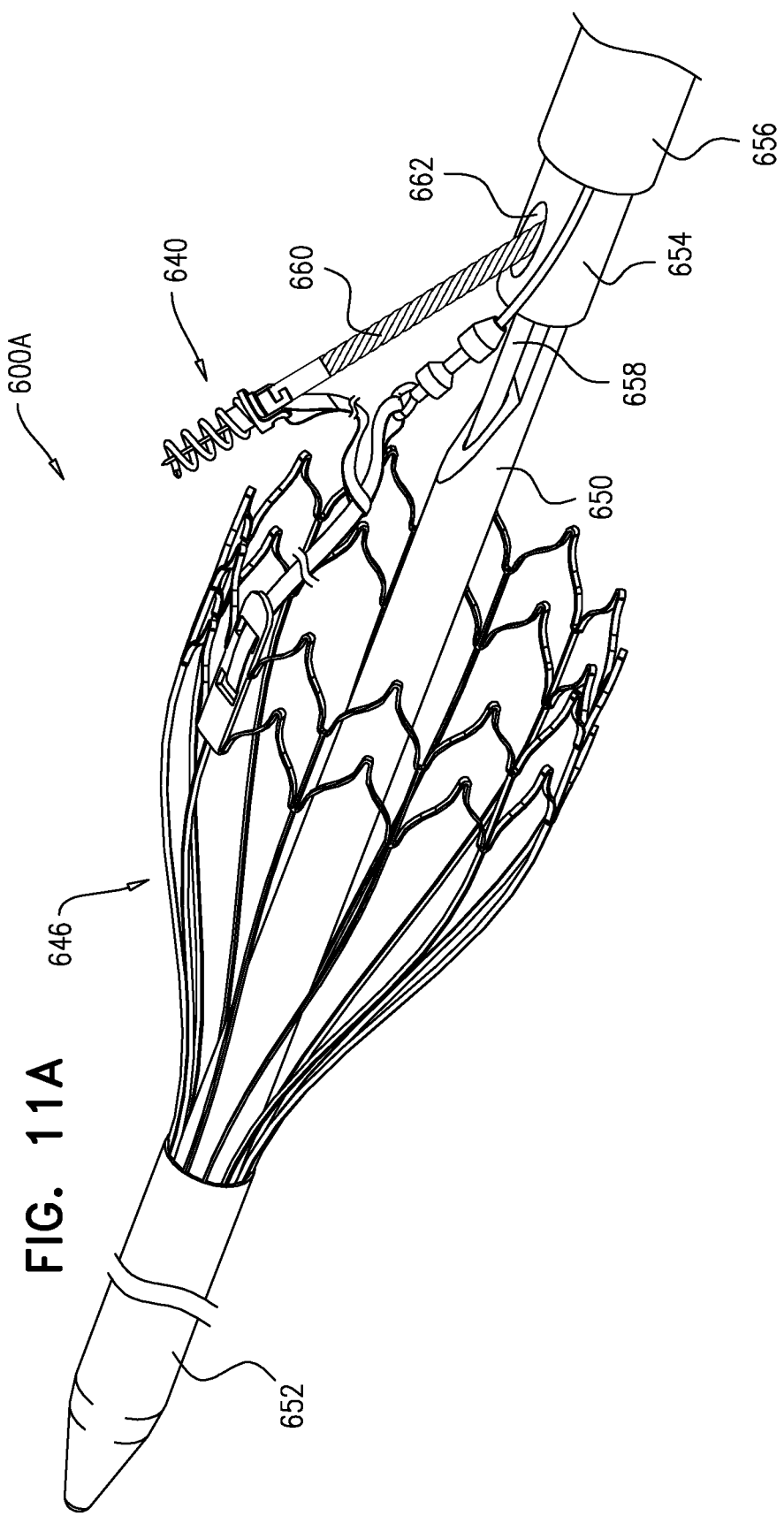

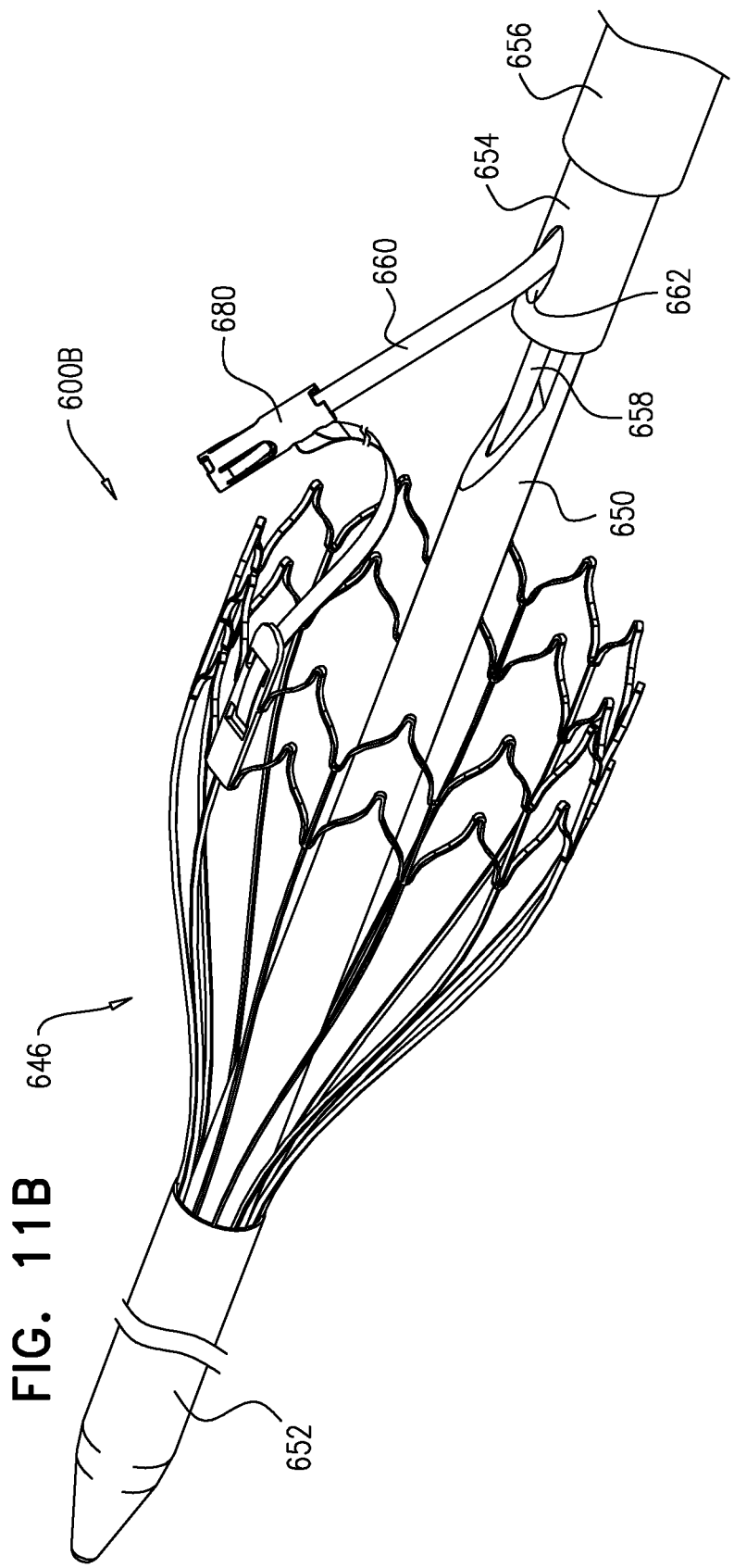

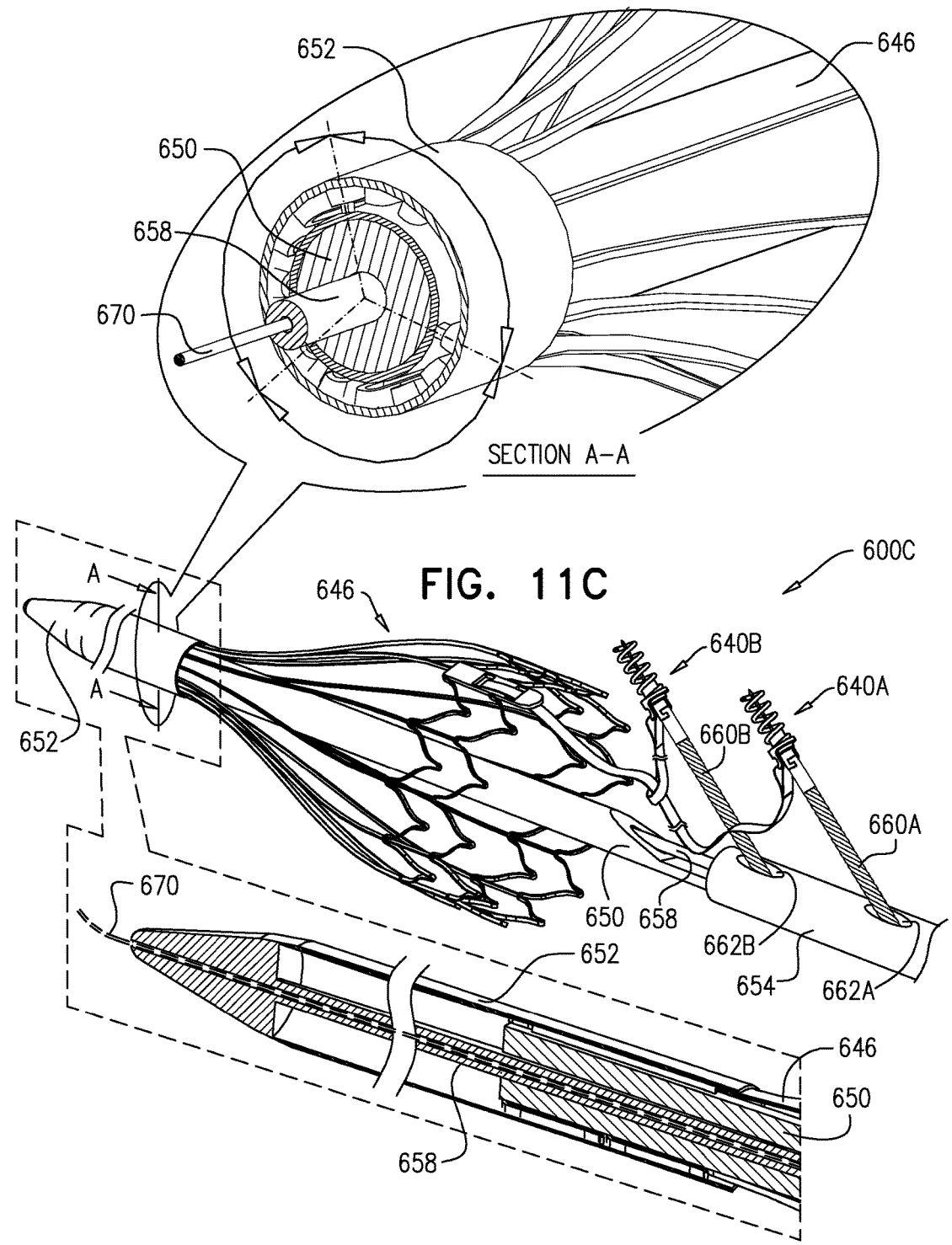

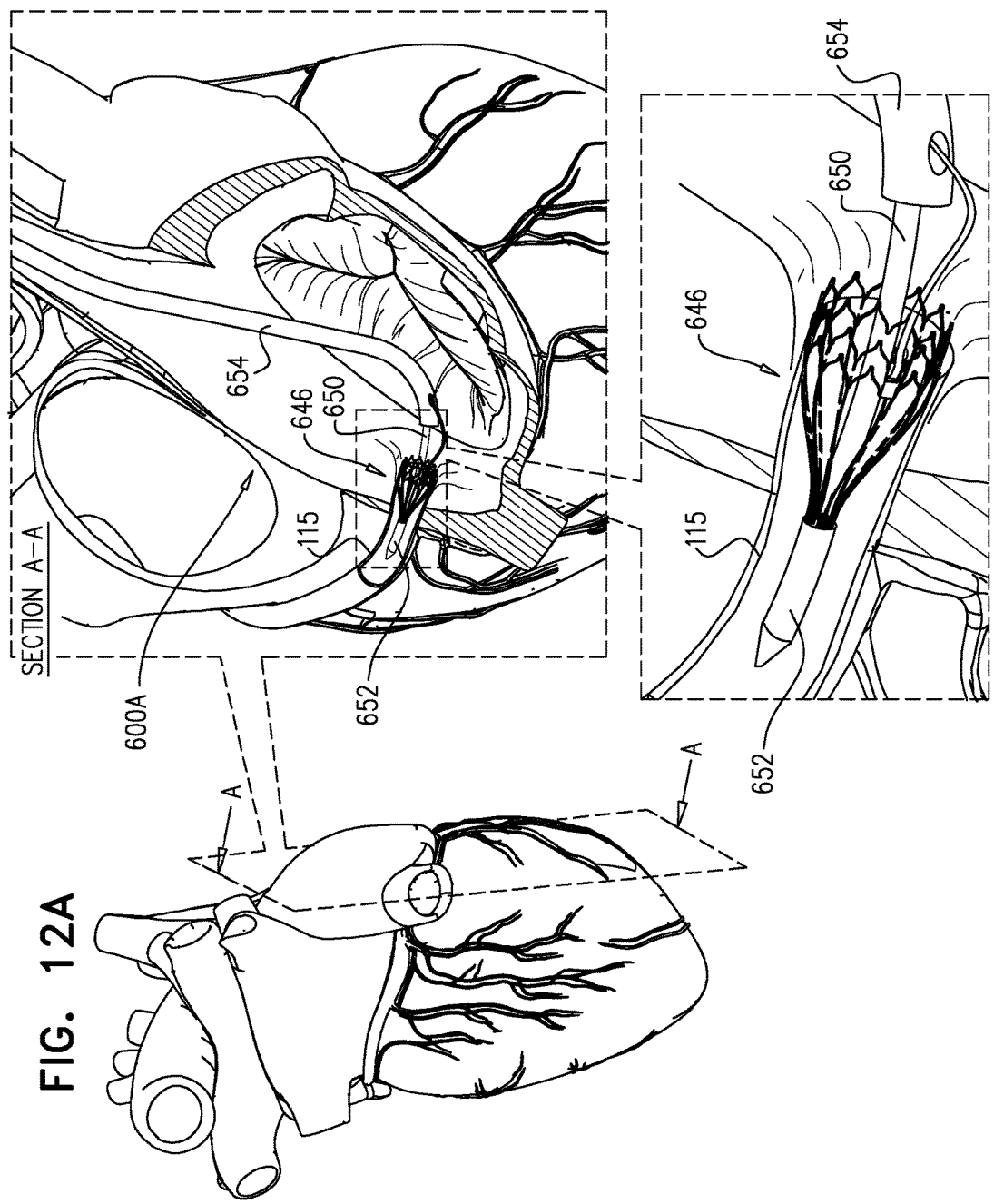

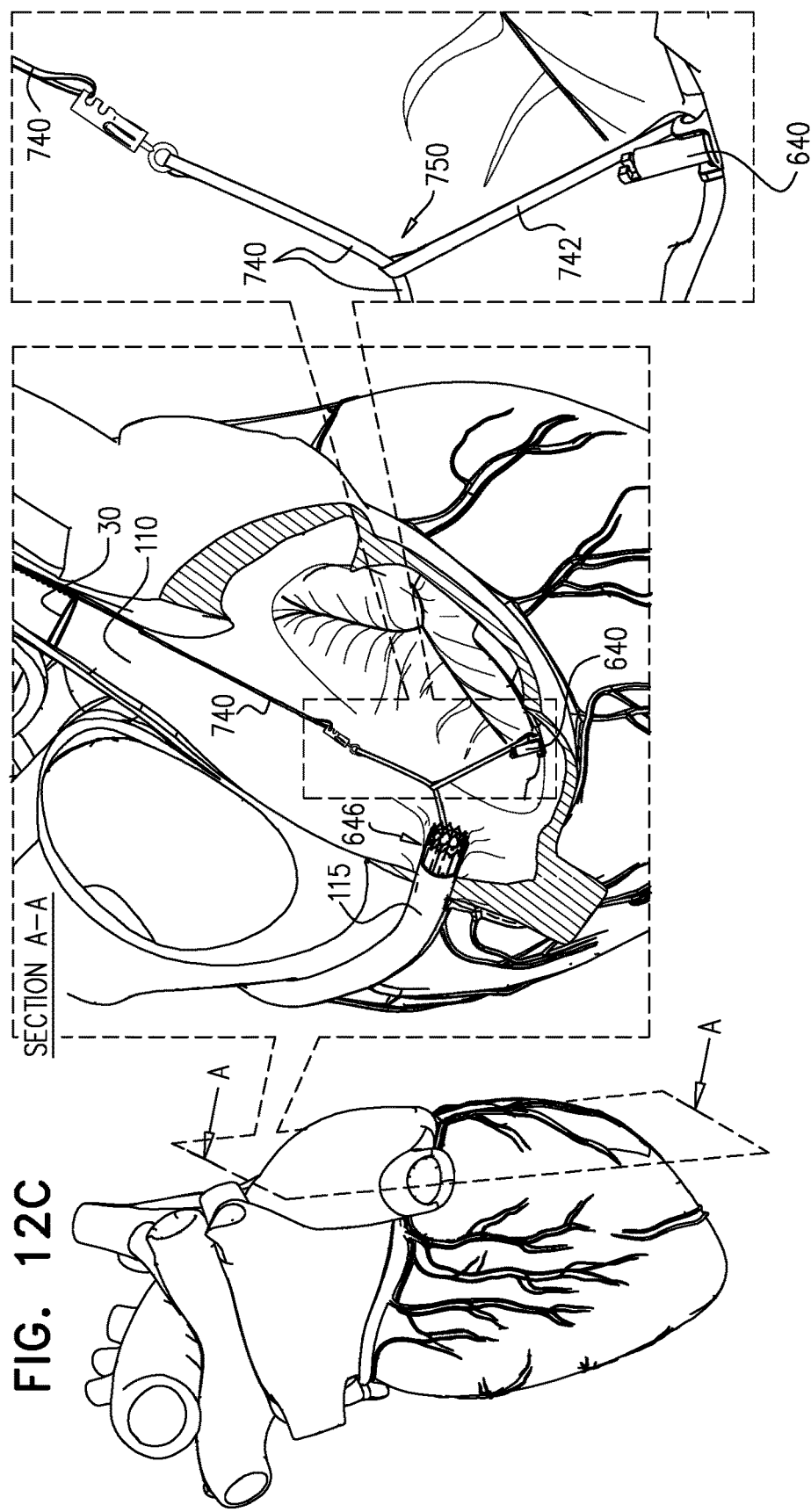

MULTIPLE ANCHORING-POINT TENSION SYSTEM

CROSS-REFERENCE TO RELATED APPLICATIONS

The present application is a continuation-in-part of U.S. application Ser. No. 15/031,069 to Gilmore et al., which is the US National Stage of International Application PCT/IB2014/002351, filed Oct. 28, 2014, which claims priority from U.S. Provisional Application 61/897,509, filed Oct. 30, 2013, all of which applications are assigned to the assignee of the present application and are incorporated herein by reference.

FIELD OF THE APPLICATION

Some applications of the present invention relate in general to valve repair. More specifically, some applications of the present invention relate to repair of an atrioventricular valve of a patient.

BACKGROUND OF THE APPLICATION

Functional tricuspid regurgitation (FTR) is governed by several pathophysiologic abnormalities such as tricuspid valve annular dilatation, annular shape abnormality, pulmonary hypertension, left or right ventricle dysfunction, right ventricle geometry, and leaflet tethering. Treatment options for FTR are primarily surgical. The current prevalence of moderate-to-severe tricuspid regurgitation is estimated to be 1.6 million in the United States. Of these, only 8,000 patients undergo tricuspid valve surgeries annually, most of them in conjunction with left heart valve surgeries.

SUMMARY OF THE INVENTION

In an application of the present invention, a valve-tensioning implant is provided for repairing an atrioventricular valve of a subject by applying tension using multiple anchor points. The valve-tensioning implant comprises at least first, second, and third tissue anchors, and a pulley system. The pulley system comprises a pulley and a first tether, which is connected to the second and the third tissue anchors, and is moveable through the pulley.

The pulley system is arranged so as to achieve a desired distribution and transfer of forces between the three or more tissue anchors. The pulley is arranged such that the maximum load applied when implanting the last of the tissue anchors (e.g., the third tissue anchor) is transferred between the other two tissue anchors that were earlier implanted (e.g., the first and the second tissue anchors). The load transferred to the first and the second tissue anchors approximates the first and the second tissue anchors. For some applications, two of the tissue anchors may be helical tissue anchors that are implanted around the annulus of the right atrium using mechanical purchase, and the other tissue anchor may comprise an intraluminal stent that is configured to be implanted in the superior vena cava, the inferior vena cava, or the coronary sinus and provide anchorage using friction only. The anchors and pulley system are arranged to apply relatively less force on the stent anchor than on one or both of the other helical tissue anchors. Alternatively or additionally, one of the tissue anchors may be located in a region of tissue which is thicker or stronger than the implantation sites at which the other tissue anchors are implanted. In addition, the pulley system may be arranged to align force vectors along a preferable direction which causes constriction of the tricuspid valve in a desired manner.

Repairing the atrioventricular valve typically facilitates reduction of atrioventricular valve regurgitation by altering the geometry of the atrioventricular valve and/or by altering the geometry of the wall of the right or left atrium of the heart. In some applications of the present invention, implantation of the valve-tensioning implant achieves bicuspidization of the tricuspid valve. For such applications, the anterior leaflet and the septal leaflet are typically drawn together to enhance coaptation.

In an application of the present invention, a multiple-anchor delivery tool is provided for sequentially delivering and implanting two or more helical tissue anchors of an implant. The implant comprises at least first and second helical tissue anchors, which comprise first and second heads, respectively, which comprise first and second tether interfaces. The implant also comprises a tether, which is connected to first tether interface, and coupled to second tether interface (optionally slidably coupled to second tether interface, such that the tether is moveable through the second tether interface).

The multiple-anchor delivery tool comprises a catheter shaft having proximal and distal ends. The first and the second tissue anchors are initially removably positioned in the catheter shaft at first and second longitudinal locations, respectively. The first longitudinal location is more distal than the second longitudinal location. In other words, the tissue anchors are initially positioned in the desired sequence of deployment in the tube, with the first anchor to be deployed positioned more distally than the subsequent anchor(s) to be deployed. The tissue anchors are interconnected by the tether.

The multiple-anchor delivery tool further comprises first and second torque cables, which (a) are removably coupled to the first and second heads, respectively, (b) extend within the tube proximally from the first and second heads, respectively, and (c) transmit torque when rotated, for rotating tissue-coupling elements of the anchors, respectively, into tissue. Typically, the torque cables additionally transmit axial force, to enable pushing of the tissue-coupling elements into the tissue as they are rotated. A portion of the first torque cable is initially removably positioned alongside the second tissue anchor in the tube. Thus each anchor is separately connected to a control handle of the multiple-anchor delivery tool by its own torque cable, which allows full and separate control of deployment of each anchor by an operator of the multiple-anchor delivery tool.

During use of multiple-anchor delivery tool for performing an implantation procedure, the first tissue anchor is implanted into tissue of the subject by rotating the first torque cable. The first torque cable is then decoupled from the first tissue anchor. After the first tissue anchor is implanted, the second tissue anchor is distally advanced in the tube. The second tissue anchor is implanted into tissue of the subject by rotating the second torque cable. The second torque cable is then decoupled from the second tissue anchor.

There is therefore provided, in accordance with an application of the present invention, apparatus including a valve-tensioning implant, which includes:

a first venous tissue anchor, which is configured to be implanted in a vein selected from the group of veins consisting of: a superior vena cava, an inferior vena cava, and a coronary sinus;

exactly two atrial tissue anchors, which consist of second and third atrial tissue anchors; and a pulley system, which includes:
  a pulley, which is connected to the second atrial tissue anchor; and
  a tether, which (a) is connected to the first venous tissue anchor and the third atrial tissue anchor, (b) is moveable through the pulley, and (c) has a length, measured between the first venous and the third atrial tissue anchors, of at least 30 mm.

For some applications, the pulley includes a loop, and the tether is slidably moveable through the loop. For some applications, a coefficient of kinetic friction between the tether and the loop is less than 0.5, such as less 0.2, e.g., less than 0.1. For some applications, the loop includes a closed loop. For some applications, the pulley includes a ring, and the tether is slidably moveable through the ring. For some applications, a coefficient of kinetic friction between the tether and the ring is less than 0.5, such as less 0.2, e.g., less than 0.1. For some applications, the pulley includes a wheel.

For some applications, the first venous tissue anchor includes an intraluminal stent. For some applications, the second and the third atrial tissue anchors include respective helical tissue-coupling elements.

For any of the applications described above, the tether may be a first tether, the length may be a first length, and the pulley system may further include a second tether which (a) is connected to the pulley and the second atrial tissue anchor, so as to connect the pulley to the second atrial tissue anchor, and (b) has a second length, measured between the second atrial tissue anchor and the pulley, of at least 3 mm. For some applications, the second length equals at least 10% of the first length. For some applications, the first length is between 30 and 120 mm, and/or the second length is between 5 and 8 mm.

For any of the applications described above, the second atrial tissue anchor may include (a) a tissue-coupling element, and (b) a head, and the pulley may be connected to the head such that, when the pulley is fully extended away from the head, a distance between (a) a site on the pulley farthest from the head and (b) a site on the head closest to the pulley, is at least 3 mm. For some applications, the head is rigid. For some applications, the head includes a tether interface that is rotatable with respect to the tissue-coupling element.

For any of the applications described above, the second atrial tissue anchor may include (a) a tissue-coupling element, and (b) a head, which includes the pulley. For some applications, the head includes an interface, which (a) includes the pulley and (b) is rotatable with respect to the tissue-coupling element. For some applications, the pulley includes an eyelet. For some applications, the pulley includes a roller. For some applications, the pulley includes a flexible longitudinal member that is connected to the head at two points along the flexible longitudinal member, so as to define a loop longitudinally between the two points. For some applications, the second tissue-coupling element is helical. For some applications, the third atrial tissue anchor includes a helical tissue-coupling element.

For any of the applications described above, the apparatus may further include a delivery system, configured to deliver and enable implantation of the valve-tensioning implant, and the delivery system may include at least one catheter shaft.

There is further provided, in accordance with an application of the present invention, apparatus including a valve-tensioning implant, which includes:
  a first venous tissue anchor, which is configured to be implanted in a vein selected from the group of veins consisting of: a superior vena cava, an inferior vena cava, and a coronary sinus;
  exactly two tissue anchors, which consist of second and third atrial tissue anchors; and
  a pulley system, which includes:
    a pulley, which is connected to the first venous tissue anchor;
    a first tether, which (a) is connected to the second and the third atrial tissue anchors, (b) is moveable through the pulley, and (c) has a first length, measured between the second and the third atrial tissue anchors, of at least 10 mm; and
    a second tether, which (a) is connected to the first venous tissue anchor and to the pulley, and (b) has a second length, measured between the first venous tissue anchor and the pulley, of at least 30 mm.

For some applications, the pulley includes a loop, and the second tether is slidably moveable through the loop. For some applications, a coefficient of kinetic friction between the second tether and the loop is less than 0.5, such as less 0.2, e.g., less than 0.1. For some applications, the loop includes a closed loop. For some applications, the pulley includes a ring, and the second tether is slidably moveable through the ring. For some applications, a coefficient of kinetic friction between the second tether and the ring is less than 0.5, such as less 0.2, e.g., less than 0.1. For some applications, the pulley includes a wheel.

For some applications, the first venous tissue anchor includes an intraluminal stent. For some applications, the second and the third atrial tissue anchors include respective helical tissue-coupling elements. For some applications, the second length equals at least the first length. For some applications, the first length is between 20 and 50 mm. For some applications, the second length is between 30 and 80 mm.

For any of the applications described above, the apparatus may further include a delivery system, configured to deliver and enable implantation of the valve-tensioning implant, and the delivery system may include at least one catheter shaft.

There is still further provided, in accordance with an application of the present invention, apparatus including a valve-tensioning implant, which includes:
  first, second, and third tissue anchors; and
  a pulley system, which includes:
    a pulley,
    a first tether, which (a) is connected to the second and the third tissue anchors, (b) is moveable through the pulley, and (c) has a first length, measured between the second and the third tissue anchors, of at least 15 mm; and
    a second tether, which (a) is connected to the first tissue anchor and to the pulley, and (b) has a second length, measured between the first tissue anchor and the pulley, of at least 15 mm.

For some applications, the apparatus includes exactly three tissue anchors, which consist of the first, the second, and the third tissue anchors, and no other tissue anchors.

For some applications, the pulley includes a loop, and the first tether is slidably moveable through the loop. For some applications, a coefficient of kinetic friction between the first tether and the loop is less than 0.5, such as less 0.2, e.g., less than 0.1. For some applications, the loop includes a closed loop. For some applications, the pulley includes a ring, and the first tether is slidably moveable through the ring. For some applications, a coefficient of kinetic friction between the first tether and the ring is less than 0.5, such as less 0.2, e.g., less than 0.1. For some applications, the pulley includes a wheel.

For some applications, the second length equals at least 80% of the first length. For some applications, the first length is between 15 and 30 mm. For some applications, the second length is between 25 and 80 mm. For some applications, the second length equals at least 15% of the first length. For some applications, the first length is between 15 and 140 mm. For some applications, the first length is between 30 and 120 mm.

For some applications, the third tissue anchor is configured to be implanted in a vein selected from the group of veins consisting of: a superior vena cava, an inferior vena cava, and a coronary sinus.

For any of the applications described above, the first anchor may be configured to be implanted in a vein selected from the group of veins consisting of: a superior vena cava, an inferior vena cava, and a coronary sinus. For some applications, the first tissue anchor includes an intraluminal stent. For some applications, the second and third tissue anchors include respective helical tissue-coupling elements.

For any of the applications described above, the third tissue anchor may include an intraluminal stent. For some applications, the first and the second tissue anchors include respective helical tissue-coupling elements.

For any of the applications described above, the apparatus may further include a delivery system, configured to deliver and enable implantation of the valve-tensioning implant, and the delivery system may include at least one catheter shaft.

There is additionally provided, in accordance with an application of the present invention, apparatus including a valve-tensioning implant, which includes:
  a first tissue anchor, which includes (a) a tissue-coupling element, and (b) a head:
    second and third tissue anchors; and
    a pulley system, which includes:
      a pulley, which is connected to the head of the first tissue anchor, such that, when the pulley is fully extended away from the head, a distance between (a) a site on the pulley farthest from the head and (b) a site on the head closest to the pulley, is at least 5 mm; and
      a tether, which (a) is connected to the second and the third tissue anchors, (b) is moveable through the pulley, and (c) has a length, measured between the second and the third tissue anchors, of at least 15 mm.

For some applications, the head is rigid.

For some applications, the head comprises a tether interface, to which the tether is connected, and the tether interface between the head of the tissue anchor and tether is rotatable with respect to the tissue-coupling element.

For some applications, the pulley includes a loop, and the tether is slidably moveable through the loop. For some applications, a coefficient of kinetic friction between the tether and the loop is less than 0.5, such as less 0.2. e.g., less than 0.1. For some applications, the loop includes a closed loop. For some applications, the pulley includes a ring, and the tether is slidably moveable through the ring. For some applications, a coefficient of kinetic friction between the tether and the ring is less than 0.5, such as less 0.2, e.g., less than 0.1. For some applications, the pulley includes a wheel.

For some applications, the third tissue anchor is configured to be implanted in a vein selected from the group of veins consisting of: a superior vena cava, an inferior vena cava, and a coronary sinus.

For some applications, the third tissue anchor includes an intraluminal stent. For some applications, the tissue-coupling element of the first tissue anchor includes a first helical tissue-coupling element, and the second tissue anchor includes a second helical tissue-coupling element.

For some applications, the distance equals at least 10% of the length. For some applications, the length is between 30 and 200 mm. For some applications, the distance is between 15 and 50 mm.

For any of the applications described above, the apparatus may further include a delivery system, configured to deliver and enable implantation of the valve-tensioning implant, and the delivery system may include at least one catheter shaft.

There is yet additionally provided, in accordance with an application of the present invention, apparatus including a valve-tensioning implant, which includes:
  a first venous tissue anchor, which is configured to be implanted in a vein selected from the group of veins consisting of: a superior vena cava and an inferior vena cava:
    a second atrial tissue anchor;
    a third venous tissue anchor, which is configured to be implanted in a coronary sinus; and
    a pulley system, which includes:
      a pulley, which is connected to the second atrial tissue anchor; and
      a tether, which (a) is connected to the first and the third venous tissue anchors, (b) is moveable through the pulley, and (c) has a length, measured between the first and the third venous tissue anchors, of at least 30 mm.

For some applications, the pulley includes a loop, and the tether is slidably moveable through the loop. For some applications, a coefficient of kinetic friction between the tether and the loop is less than 0.5, such as less 0.2, e.g., less than 0.1. For some applications, the loop includes a closed loop. For some applications, the pulley includes a ring, and the tether is slidably moveable through the ring. For some applications, a coefficient of kinetic friction between the tether and the ring is less than 0.5, such as less 0.2, e.g., less than 0.1. For some applications, the pulley includes a wheel.

For some applications, the first and the third venous tissue anchor includes first and second intraluminal stents, respectively. For some applications, a greatest outer diameter of the second intraluminal stent is no more than 80% of a greatest outer diameter of the first intraluminal stent, when the first and the second intraluminal stents are unconstrained and fully radially expanded. For some applications, the second atrial tissue anchor includes a helical tissue-coupling element.

For any of the applications described above, the tether may be a first tether, the length may be a first length, and the pulley system may further include a second tether, which (a) is connected to the pulley and the second atrial tissue anchor, so as to connect the pulley to the second atrial tissue anchor, and (b) has a second length, measured between the second atrial tissue anchor and the pulley, of at least 3 mm. For some applications, the second length equals at least 10% of the first length. For some applications, the first length is between 30 and 80 mm. For some applications, the second length is between 5 and 8 mm.

For any of the applications described above, the second atrial tissue anchor may include (a) a tissue-coupling element, and (b) a head, and the pulley may be connected to the head such that, when the pulley is fully extended away from the head, a distance between (a) a site on the pulley farthest from the head and (b) a site on the head closest to the pulley, is at least 3 mm. For some applications, the head is rigid. For some applications, the head includes an interface that is rotatable with respect to the tissue-coupling element.

For any of the applications described above, the second atrial tissue anchor may include (a) a tissue-coupling element, and (b) a head, which includes the pulley. For some applications, the head includes an interface, which (a)

includes the pulley and (b) is rotatable with respect to the tissue-coupling element. For some applications, the pulley includes an eyelet. For some applications, the pulley includes a roller. For some applications, the pulley includes a flexible longitudinal member that is connected to the head at two points along the flexible longitudinal member, so as to define a loop longitudinally between the two points. For some applications, the tissue-coupling element is helical.

For any of the applications described above, the apparatus may further include a delivery system, configured to deliver and enable implantation of the valve-tensioning implant, and the delivery system may include at least one catheter shaft.

There is also provided, in accordance with an application of the present invention, apparatus including:
  an implant, which includes:
    at least first and second tissue anchors, which include (a) first and second helical tissue-coupling elements, respectively, and (b) first and second heads, respectively, which include first and second tether interfaces; and
    a tether, which is connected to the first tether interface, and coupled to the second tether interface; and
  a multiple-anchor delivery tool, which includes:
    a catheter shaft having proximal and distal ends, wherein the first and the second tissue anchors are removably positioned in the catheter shaft at first and second longitudinal locations, respectively, the first longitudinal location more distal than the second longitudinal location; and
    first and second torque cables, which (a) are removably coupled to the first and the second heads, respectively, (b) extend within the catheter shaft proximally from the first and the second heads, respectively, and (c) transmit torque when rotated, wherein a portion of the first torque cable is removably positioned alongside the second tissue anchor in the catheter shaft.

For some applications:
  the implant further includes a third tissue anchor, which includes (a) a third helical tissue-coupling elements and (b) a third head, which includes a third tether interface,
  the tether, which is coupled to the third tether interface,
  the third tissue anchor is removably positioned in the catheter shaft at a third longitudinal location that is more proximal than the second longitudinal location, and
  the multiple-anchor delivery tool further includes a third torque cable, which (a) is removably coupled to the third head, (b) extends within the catheter shaft proximally from the third head, and (c) transmits torque when rotated, wherein a portion of the second torque cable is removably positioned alongside the third tissue anchor in the catheter shaft.

For some applications, the first tether interface is rotatable with respect to the first tissue-coupling element.

For any of the applications described above, the first torque cable may be shaped so as to define a lumen therethrough, and the multiple-anchor delivery tool may further include a shaft, which removably passes through the lumen. For some applications:
  the head is shaped so as to define a proximal coupling element,
  the head, including the proximal coupling element, is shaped so as to define a first longitudinal channel at least partially therethrough, which channel is coaxial with the head.
  a distal end of the first torque cable includes a distal coupling element, which is shaped so as to define a second longitudinal channel therethrough, which channel is coaxial with the lumen of the first torque cable,
  the proximal and the distal coupling elements are shaped so as to define corresponding interlocking surfaces, and
  the shaft, when disposed through the first and the second channels, prevents decoupling of the distal coupling element from the proximal coupling element.

For some applications, the shaft is shaped so as to define a sharp distal tip.

There is further provided, in accordance with an application of the present invention, a method including:
  implanting:
    a first venous tissue anchor in a vein selected from the group of veins consisting of: a superior vena cava, an inferior vena cava, and a coronary sinus,
    exactly two atrial tissue anchors, which consist of second and third atrial tissue anchors, at respective different atrial sites, each of which sites is selected from the group of sites consisting of: an annulus of a tricuspid valve, and a wall of a right atrium of a heart above the annulus of the tricuspid valve, and
    a pulley system, which includes (a) a pulley, which is connected to the second atrial tissue anchor, and (b) a tether, which (i) is connected to the first venous tissue anchor and the third atrial tissue anchor, (ii) is moveable through the pulley, and (iii) has a length, measured between the first venous and the third atrial tissue anchors, of at least 30 mm; and
  reducing a size of a tricuspid orifice by tensioning the tether.

For some applications, the pulley includes a loop, and tensioning the tether includes sliding the tether through the loop. For some applications, a coefficient of kinetic friction between the tether and the loop is less than 0.5, such as less 0.2, e.g., less than 0.1. For some applications, the loop is a closed loop.

For some applications, the pulley includes a ring, and tensioning the tether includes sliding the tether through the ring. For some applications, a coefficient of kinetic friction between the tether and the ring is less than 0.5, such as less 0.2, e.g., less than 0.1.

For some applications, the pulley includes a wheel, and tensioning the tether includes rotating the wheel by moving the tether through the pulley.

For some applications, the first venous tissue anchor includes an intraluminal stent, and implanting the first venous tissue anchor includes expanding the intraluminal stent in the selected vein. For some applications, the second and the third atrial tissue anchors include respective helical tissue-coupling elements, and implanting the second and the third atrial tissue anchors includes rotating the helical tissue-coupling elements into tissue at the sites, respectively.

For some applications, implanting the first venous tissue anchor, the second atrial tissue anchor, the third atrial tissue anchor, and the pulley system includes positioning the first venous tissue anchor, the second atrial tissue anchor, the third atrial tissue anchor, and the pulley system such that two longitudinal portions of the tether adjacent to and on opposite sides of the pulley define an angle therebetween of between 40 and 85 degrees.

For some applications, implanting the first venous tissue anchor includes implanting the first venous tissue anchor in the inferior vena cava. For some applications, implanting the second atrial tissue anchor includes implanting the second atrial tissue anchor within 1 cm of a site on the annulus that circumferentially corresponds to a circumferential middle of a septal leaflet of the tricuspid valve; and implanting the third atrial tissue anchor includes implanting the third atrial tissue anchor within 1 cm of a site on the annulus that circumferentially corresponds to an anteroposterior commissure of the tricuspid valve.

For some applications, implanting the second atrial tissue anchor includes implanting the second atrial tissue anchor within 1 cm of a site on the annulus that circumferentially corresponds to a septoanterior commissure of the tricuspid valve; and implanting the third atrial tissue anchor includes implanting the third atrial tissue anchor within 1 cm of a site on the annulus that circumferentially corresponds to an anteroposterior commissure of the tricuspid valve.

For some applications, implanting the second atrial tissue anchor includes implanting the second atrial tissue anchor within 1 cm of a site on the annulus that circumferentially corresponds to an anteroposterior commissure of the tricuspid valve. For some applications, implanting the third atrial tissue anchor includes implanting the third atrial tissue anchor within 1 cm of a site on the annulus that circumferentially corresponds to a septoanterior commissure of the tricuspid valve. For some applications, implanting the third atrial tissue anchor includes implanting the third atrial tissue anchor within 1 cm of a site on the annulus that circumferentially corresponds to a circumferential middle of a septal leaflet of the tricuspid valve. For some applications, implanting the third atrial tissue anchor includes implanting the third atrial tissue anchor in the coronary sinus. For some applications, implanting the second atrial tissue anchor includes implanting the second atrial tissue anchor within 1 cm of a site on the annulus that circumferentially corresponds to an anteroposterior commissure of the tricuspid valve; and implanting the third atrial tissue anchor includes implanting the third atrial tissue anchor within 1 cm of a site on the annulus that circumferentially corresponds to a septoanterior commissure of the tricuspid valve. For some applications, implanting the second atrial tissue anchor includes implanting the second atrial tissue anchor within 1 cm of a site on the annulus that circumferentially corresponds to a septoanterior commissure of the tricuspid valve; and implanting the third atrial tissue anchor includes implanting the third atrial tissue anchor within 1 cm of a site on the annulus that circumferentially corresponds to a septoposterior commissure of the tricuspid valve.

For some applications, implanting the first venous tissue anchor includes implanting the first venous tissue anchor in the superior vena cava. For some applications, implanting the second atrial tissue anchor includes implanting the second atrial tissue anchor within 1 cm of a site on the annulus that circumferentially corresponds to an anteroposterior commissure of the tricuspid valve. For some applications, implanting the third atrial tissue anchor includes implanting the third atrial tissue anchor within 1 cm of a site on the annulus that circumferentially corresponds to a septoanterior commissure of the tricuspid valve. For some applications, implanting the third atrial tissue anchor includes implanting the third atrial tissue anchor within 1 cm of a site on the annulus that circumferentially corresponds to a circumferential middle of a septal leaflet of the tricuspid valve. For some applications, implanting the third atrial tissue anchor includes implanting the third atrial tissue anchor in the coronary sinus. For some applications, implanting the second atrial tissue anchor includes implanting the second atrial tissue anchor within 1 cm of a site on the annulus that circumferentially corresponds to a septoanterior commissure of the tricuspid valve; and implanting the third atrial tissue anchor includes implanting the third atrial tissue anchor within 1 cm of a site on the annulus that circumferentially corresponds to an anteroposterior commissure of the tricuspid valve. For some applications, implanting the second atrial tissue anchor includes implanting the second atrial tissue anchor within 1 cm of a site on the annulus that circumferentially corresponds to a circumferential middle of a septal leaflet of the tricuspid valve; and implanting the third atrial tissue anchor includes implanting the third atrial tissue anchor within 1 cm of a site on the annulus that circumferentially corresponds to an anteroposterior commissure of the tricuspid valve.

For some applications, implanting the first venous tissue anchor includes implanting the first venous tissue anchor in the coronary sinus. For some applications, implanting the second atrial tissue anchor includes implanting the second atrial tissue anchor within 1 cm of a site on the annulus that circumferentially corresponds to an anteroposterior commissure of the tricuspid valve; and implanting the third atrial tissue anchor includes implanting the third atrial tissue anchor within 1 cm of a site on the annulus that circumferentially corresponds to a septoanterior commissure of the tricuspid valve.

For some applications, the tether is a first tether; the length is a first length; the pulley system further includes a second tether, which (a) is connected to the pulley and the second atrial tissue anchor, so as to connect the pulley to the second atrial tissue anchor, and (b) has a second length, measured between the second atrial tissue anchor and the pulley, of at least 3 mm; and implanting the pulley system further includes implanting the second tether.

For some applications, the second atrial tissue anchor includes (a) a tissue-coupling element, and (b) a head; the pulley is connected to the head; and tensioning the tether includes fully extending the pulley away from the head, such that a distance between (a) a site on the pulley farthest from the head and (b) a site on the head closest to the pulley, is at least 3 mm.

For some applications, the head is rigid. For some applications, the head includes a tether interface that is rotatable with respect to the tissue-coupling element.

For some applications, implanting the first venous tissue anchor, the second atrial tissue anchor, the third atrial tissue anchor, and the pulley system includes positioning the first venous tissue anchor, the second atrial tissue anchor, the third atrial tissue anchor, and the pulley system such that two longitudinal portions of the tether adjacent to and on opposite sides of the pulley define an angle therebetween of at least 120 degrees. For some applications, the angle is at least 135 degrees.

For some applications, implanting the first venous tissue anchor, the second atrial tissue anchor, the third atrial tissue anchor, and the pulley system includes positioning the first venous tissue anchor, the second atrial tissue anchor, the third atrial tissue anchor, and the pulley system such that two longitudinal portions of the tether adjacent to and on opposite sides of the pulley define an angle there between of less than 90 degrees. For some applications, the angle is less than 60 degrees.

For some applications, the second atrial tissue anchor includes (a) a tissue-coupling element, and (b) a head, which includes the pulley, and implanting the second atrial tissue anchor includes implanting the head. For some applications, the head includes an interface, which (a) includes the pulley, and (b) is rotatable with respect to the tissue-coupling element. For some applications, the pulley includes an eyelet. For some applications, the pulley includes a roller. For some applications, the pulley includes a flexible longitudinal member that is connected to the head at two points along the flexible longitudinal member, so as to define a loop longitudinally between the two points. For some applications, the tissue-coupling element is helical. For some applications, the third atrial tissue anchor includes a helical tissue-coupling element.

There is still further provided, in accordance with an application of the present invention, a method including:
  implanting:
    a first venous tissue anchor in a vein selected from the group of veins consisting of: a superior vena cava, an inferior vena cava, and a coronary sinus,
    exactly two atrial tissue anchors, which consist of second and third atrial tissue anchors, at respective different atrial sites, each of which sites is selected from the group of sites consisting of: an annulus of a tricuspid valve, and a wall of a right atrium of a heart above the annulus of the tricuspid valve, and
    a pulley system, which includes (a) a pulley, which is connected to the first venous tissue anchor, (b) a first tether, which (i) is connected to the second and the third atrial tissue anchors, (ii) is moveable through the pulley, and (iii) has a first length, measured between the second and the third atrial tissue anchors, of at least 10 mm, and (c) a second tether, which (i) is connected to the first venous tissue anchor and to the pulley, and (ii) has a second length, measured between the first venous tissue anchor and the pulley, of at least 30 mm; and
  reducing a size of a tricuspid orifice by tensioning the second tether.

For some applications, the pulley includes a loop, and tensioning the first tether includes sliding the first tether through the loop. For some applications, a coefficient of kinetic friction between the first tether and the loop is less than 0.5, such as less 0.2, e.g., less than 0.1. For some applications, the loop is a closed loop. For some applications, the pulley includes a ring, and tensioning the first tether includes sliding the first tether through the ring. For some applications, a coefficient of kinetic friction between the first tether and the ring is less than 0.5, such as less 0.2, e.g., less than 0.1. For some applications, the pulley includes a wheel.

For some applications, the first venous tissue anchor includes an intraluminal stent, and implanting the first venous tissue anchor includes expanding the intraluminal stent in the selected vein. For some applications, the second and the third atrial tissue anchors include respective helical tissue-coupling elements, and implanting the second and the third atrial tissue anchors includes rotating the helical tissue-coupling elements into tissue at the sites, respectively.

For some applications, implanting the first venous tissue anchor, the second atrial tissue anchor, the third atrial tissue anchor, and the pulley system includes positioning the first venous tissue anchor, the second atrial tissue anchor, the third atrial tissue anchor, and the pulley system such that two longitudinal portions of the first tether adjacent to and on opposite sides of the pulley define an angle therebetween of at least 120 degrees. For some applications, positioning the first venous tissue anchor, the second atrial tissue anchor, the third atrial tissue anchor, and the pulley system such that the two longitudinal portions of the first tether adjacent to and on the opposite sides of the pulley define an angle therebetween of at least 135 degrees.

For some applications, implanting the first venous tissue anchor includes implanting the first venous tissue anchor in the inferior vena cava. For some applications, implanting the second atrial tissue anchor includes implanting the second atrial tissue anchor within 1 cm of a site on the annulus that circumferentially corresponds to an anteroposterior commissure of the tricuspid valve. For some applications, implanting the third atrial tissue anchor includes implanting the third atrial tissue anchor within 1 cm of a site on the annulus that circumferentially corresponds to a septoanterior commissure of the tricuspid valve. For some applications, implanting the third atrial tissue anchor includes implanting the third atrial tissue anchor within 1 cm of a site on the annulus that circumferentially corresponds to a circumferential middle of a septal leaflet of the tricuspid valve.

For some applications, implanting the first venous tissue anchor includes implanting the first venous tissue anchor in the superior vena cava. For some applications, implanting the third atrial tissue anchor includes implanting the third atrial tissue anchor within 1 cm of a site on the annulus that circumferentially corresponds to an anteroposterior commissure of the tricuspid valve. For some applications, implanting the second atrial tissue anchor includes implanting the second atrial tissue anchor within 1 cm of a site on the annulus that circumferentially corresponds to a septoanterior commissure of the tricuspid valve. For some applications, implanting the second atrial tissue anchor includes implanting the second atrial tissue anchor within 1 cm of a site on the annulus that circumferentially corresponds to a circumferential middle of a septal leaflet of the tricuspid valve.

For some applications, implanting the first venous tissue anchor includes implanting the first venous tissue anchor in the coronary sinus. For some applications, implanting the third atrial tissue anchor includes implanting the third atrial tissue anchor within 1 cm of a site on the annulus that circumferentially corresponds to an anteroposterior commissure of the tricuspid valve. For some applications, implanting the second atrial tissue anchor includes implanting the second atrial tissue anchor within 1 cm of a site on the annulus that circumferentially corresponds to a septoanterior commissure of the tricuspid valve. For some applications, implanting the second atrial tissue anchor includes implanting the second atrial tissue anchor within 1 cm of a site on the annulus that circumferentially corresponds to a circumferential middle of a septal leaflet of the tricuspid valve.

There is additionally provided, in accordance with an application of the present invention, a method including:
  implanting:
    first, second, and third tissue anchors at respective different sites, and
    a pulley system, which includes (a) a pulley, (b) a first tether, which (i) is connected to the second and the third tissue anchors, (ii) is moveable through the pulley, and (iii) has a first length, measured between the second and the third tissue anchors, of at least 15 mm, and (c) a second tether, which (i) is connected to the first tissue anchor and to the pulley, and (ii) has a second length, measured between the first tissue anchor and the pulley, of at least 15 mm; and
  reducing a size of a tricuspid orifice by tensioning the second tether.

For some applications, implanting the first, the second, and the third tissue anchors includes implanting exactly three tissue anchors, which consist of the first, the second, and the third tissue anchors, and no other tissue anchors.

For some applications, the pulley includes a loop, and tensioning the second tether includes sliding the first tether through the loop. For some applications, a coefficient of kinetic friction between the first tether and the loop is less than 0.5, such as less 0.2. e.g., less than 0.1. For some applications, the loop is a closed loop. For some applications, the pulley includes a ring, and tensioning the second tether includes sliding the first tether through the ring. For some applications, a coefficient of kinetic friction between the first tether and the ring is less than 0.5, such as less 0.2, e.g., less than 0.1. For some applications, the pulley includes a wheel.

For some applications, implanting the first anchor includes implanting the first anchor in a vein selected from the group of veins consisting of: a superior vena cava, an inferior vena cava, and a coronary sinus. For some applications, the first tissue anchor includes an intraluminal stent, and implanting the first tissue anchor includes implanting the intraluminal stent in the selected vein. For some applications, the second and third tissue anchors include respective helical tissue-coupling elements, and implanting the second and the third tissue anchors includes rotating the helical tissue-coupling elements into tissue at the sites, respectively.

For some applications, implanting the third tissue anchor includes implanting the third tissue anchor in a vein selected from the group of veins consisting of: a superior vena cava, an inferior vena cava, and a coronary sinus. For some applications, the third tissue anchor includes an intraluminal stent, and implanting the third tissue anchor includes implanting the intraluminal stent in the selected vein. For some applications, the first and the second tissue anchors include respective helical tissue-coupling elements, and implanting the first and the second tissue anchors includes rotating the helical tissue-coupling elements into tissue at the sites, respectively.

There is yet additionally provided, in accordance with an application of the present invention, a method including:
 implanting:
  a first tissue anchor, which includes (a) a tissue-coupling element and (b) a head,
  second and third tissue anchors, and
  a pulley system, which includes (a) a pulley, which is connected to the head of the first tissue anchor, and (b) a tether, which (i) is connected to the second and the third tissue anchors, (ii) is moveable through the pulley, and (iii) has a length, measured between the second and the third tissue anchors, of at least 15 mm; and
 reducing a size of a tricuspid orifice by tensioning the tether, so as to fully extend the pulley away from the head, such that a distance between (a) a site on the pulley farthest from the head and (b) a site on the head closest to the pulley, is at least 5 mm.

For some applications, the head is rigid.

For some applications, the head includes an interface that is rotatable with respect to the tissue-coupling element.

For some applications, the pulley includes a loop, and tensioning the tether includes sliding the tether through the loop. For some applications, a coefficient of kinetic friction between the tether and the loop is less than 0.5, such as less 0.2, e.g., less than 0.1. For some applications, the loop is a closed loop. For some applications, the pulley includes a ring, and tensioning the tether includes sliding the tether through the ring. For some applications, a coefficient of kinetic friction between the tether and the ring is less than 0.5, such as less 0.2, e.g., less than 0.1. For some applications, the pulley includes a wheel.

For some applications, implanting the third tissue anchor includes implanting the third tissue anchor in a vein selected from the group of veins consisting of: a superior vena cava, an inferior vena cava, and a coronary sinus.

For some applications, the third tissue anchor includes an intraluminal stent, and implanting the third tissue anchor includes implanting the intraluminal stent in the selected vein. For some applications, the tissue-coupling element of the first tissue anchor includes a first helical tissue-coupling element, the second tissue anchor includes a second helical tissue-coupling element, and implanting the first and the second tissue anchors includes rotating the first and the second helical tissue-coupling elements into tissue, respectively.

There is also provided, in accordance with an application of the present invention, a method including:
 implanting:
  a first venous tissue anchor in a vein selected from the group of veins consisting of: a superior vena cava and an inferior vena cava,
  a second atrial tissue anchor at an atrial site selected from the group of sites consisting of: an annulus of a tricuspid valve, and a wall of a right atrium of a heart above the annulus of the tricuspid valve,
  a third venous tissue anchor in a coronary sinus, and
  a pulley system, which includes (a) a pulley, which is connected to the second atrial tissue anchor, and (b) a tether, which (i) is connected to the first and the third venous tissue anchors, (ii) is moveable through the pulley, and (iii) has a length, measured between the first and the third venous tissue anchors, of at least 15 mm; and
 reducing a size of a tricuspid orifice by tensioning the tether.

For some applications, the pulley includes a loop, and tensioning the tether includes sliding the tether through the loop. For some applications, a coefficient of kinetic friction between the tether and the loop is less than 0.5, such as less 0.2, e.g., less than 0.1. For some applications, the loop is a closed loop. For some applications, the pulley includes a ring, and tensioning the tether includes sliding the tether through the ring. For some applications, a coefficient of kinetic friction between the tether and the ring is less than 0.5, such as less 0.2, e.g., less than 0.1. For some applications, the pulley includes a wheel, and tensioning the tether includes rotating the wheel by moving the tether through the pulley.

For some applications:
 the first and the third venous tissue anchors include first and second intraluminal stents, respectively,
 implanting the first venous tissue anchor includes expanding the first intraluminal stent in the selected vein, and
 implanting the third venous tissue anchor includes expanding the second intraluminal stent in the coronary sinus.

For some applications, a greatest outer diameter of the second intraluminal stent is no more than 80% of a greatest outer diameter of the first intraluminal stent, when the first and the second intraluminal stents are unconstrained and fully radially expanded. For some applications, the second atrial tissue anchor includes a helical tissue-coupling element, and implanting the second atrial tissue anchor includes rotating the helical tissue-coupling element into tissue at the site.

For some applications, implanting the first venous tissue anchor, the second atrial tissue anchor, the third venous tissue anchor, and the pulley system includes positioning the first venous tissue anchor, the second atrial tissue anchor, the third venous tissue anchor, and the pulley system such that two longitudinal portions of the tether adjacent to and on opposite sides of the pulley define an angle therebetween of between 5 and 150 degrees. For some applications, implanting the first venous tissue anchor includes implanting the first venous tissue anchor in the inferior vena cava. For some applications, implanting the second atrial tissue anchor includes implanting the second atrial tissue anchor within 1 cm of a site on the annulus that circumferentially corresponds to an anteroposterior commissure of the tricuspid valve. For some applications, implanting the first venous tissue anchor includes implanting the first venous tissue anchor in the superior vena cava. For some applications, implanting the second atrial tissue anchor includes implanting the second atrial tissue anchor within 1 cm of a site on the annulus that circumferentially corresponds to an anteroposterior commissure of the tricuspid valve.

For some applications, the tether is a first tether; the length is a first length; the pulley system further includes a second tether, which (a) is connected to the pulley and the second atrial tissue anchor, so as to connect the pulley to the second atrial tissue anchor, and (b) has a second length, measured between the second atrial tissue anchor and the pulley, of at least 3 mm; and implanting the pulley system further includes implanting the second tether.

For some applications, the second atrial tissue anchor includes (a) a tissue-coupling element, and (b) a head; the pulley is connected to the head; and tensioning the tether includes fully extending the pulley away from the head, such that a distance between (a) a site on the pulley farthest from the head and (b) a site on the head closest to the pulley, is at least 3 mm. For some applications, the head is rigid. For some applications, the head includes an interface that is rotatable with respect to the tissue-coupling element.

For some applications, the second atrial tissue anchor includes (a) a tissue-coupling element, and (b) a head, which includes the pulley, and implanting the second atrial tissue anchor includes implanting the head. For some applications, the head includes an interface, which (a) includes the pulley, and (b) is rotatable with respect to the tissue-coupling element. For some applications, the pulley includes an eyelet. For some applications, the pulley includes a roller. For some applications, the pulley includes a flexible longitudinal member that is connected to the head at two points along the flexible longitudinal member, so as to define a loop longitudinally between the two points. For some applications, the tissue-coupling element is helical.

There is further provided, in accordance with an application of the present invention, a method including:

advancing a distal end of a catheter shaft of a multiple-anchor delivery tool into a body of a subject, while (a) first and second tissue anchors are removably positioned in the catheter shaft at first and second longitudinal locations, respectively, the first longitudinal location more distal than the second longitudinal location, wherein the first and the second tissue anchors include (i) first and second helical tissue-coupling elements, respectively, and (ii) first and second heads, respectively, which include first and second tether interfaces, and (b) a tether, which is connected to the first tether interface, and is coupled to the second tether interface, is removably positioned in the catheter shaft, wherein the multiple-anchor delivery tool includes first and second torque cables, which (a) are removably coupled to the first and the second heads, respectively, (b) extend within the catheter shaft proximally from the first and the second heads, respectively, and (c) transmit torque when rotated, wherein a portion of the first torque cable is removably positioned alongside the second tissue anchor in the catheter shaft:

implanting the first tissue anchor into tissue of the subject by rotating the first torque cable;

decoupling the first torque cable from the first tissue anchor;

after implanting the first tissue anchor, distally advancing the second tissue anchor in the catheter shaft:

implanting the second tissue anchor into tissue of the subject by rotating the second torque cable; and decoupling the second torque cable from the second tissue anchor.

For some applications, the first torque cable is shaped so as to define a lumen therethrough; the multiple-anchor delivery tool further includes a sharpened wire, which removably passes through the lumen, and which is initially positioned such that a distal end of the sharpened wire extends distally out of a distal end of the lumen; and the method further includes withdrawing the sharpened wire proximally.

For some applications:

the head is shaped so as to define a proximal coupling element, the head, including the proximal coupling element, is shaped so as to define a first longitudinal channel at least partially therethrough, which channel is coaxial with the head, a distal end of the first torque cable includes a distal coupling element, which is shaped so as to define a second longitudinal channel therethrough, which channel is coaxial with the lumen of the first torque cable, the proximal and the distal coupling elements are shaped so as to define corresponding interlocking surfaces, the sharpened wire, when disposed through the first and the second channels, prevents decoupling of the distal coupling element from the proximal coupling element, and withdrawing the sharpened wire proximally includes decoupling the distal coupling element from the proximal coupling element by withdrawing the sharpened wire proximally.

For some applications, the sharpened wire is shaped so as to define a sharp distal tip. For some applications, implanting the first tissue anchor includes inserting the sharp distal tip of the sharpened wire into the tissue.

For some applications:

advancing includes advancing the distal end of the catheter shaft into the body while (a) a third tissue anchor is removably positioned in the catheter shaft at a third longitudinal location that is more proximal than the second longitudinal location, the third tissue anchor includes (i) a third helical tissue-coupling elements and (ii) a third head, which includes a third tether interface, (b) the tether is coupled to the third tether interface, the multiple-anchor delivery tool further includes a third torque cable, which (a) is removably coupled to the third head, (b) extends within the catheter shaft proximally from the third head, and (c) transmits torque when rotated, a portion of the second torque cable is removably positioned alongside the third tissue anchor in the catheter shaft, and the method further includes:

after implanting the second tissue anchor, distally advancing the third tissue anchor in the catheter shaft;

implanting the third tissue anchor into tissue of the subject by rotating the third torque cable; and decoupling the third torque cable from the third tissue anchor.

For some applications, the first tether interface is rotatable with respect to the first tissue-coupling element.

There is still further provided, in accordance with an application of the present invention, a method including:
  implanting:
    a venous first tissue anchor in a vein selected from the group of veins consisting of: a superior vena cava and an inferior vena cava,
    an atrial second tissue anchor at an atrial site selected from the group of sites consisting of: an annulus of a tricuspid valve, and a wall of a right atrium of a heart above the annulus of the tricuspid valve,
    a venous third tissue anchor in a coronary sinus, and
    one or more tethers, which connect the venous first tissue anchor, the atrial second tissue anchor, and the venous third tissue anchor; and
  reducing a size of a tricuspid orifice by tensioning the one or more tethers.

For some applications:
  the venous first tissue anchor and the venous third tissue anchor include first and second intraluminal stents, respectively,
  implanting the venous first tissue anchor includes expanding the first intraluminal stent in the selected vein, and
  implanting the venous third tissue anchor includes expanding the second intraluminal stent in the coronary sinus.

For some applications, a greatest outer diameter of the second intraluminal stent is no more than 80% of a greatest outer diameter of the first intraluminal stent, when the first and the second intraluminal stents are unconstrained and fully radially expanded. For some applications, the greatest outer diameter of the second intraluminal stent is no more than 60% of the greatest outer diameter of the first intraluminal stent, when the first and the second intraluminal stents are unconstrained and fully radially expanded.

For some applications, the atrial second tissue anchor includes a helical tissue-coupling element, and implanting the atrial second tissue anchor includes rotating the helical tissue-coupling element into tissue at the site.

For some applications, implanting the venous first tissue anchor includes implanting the venous first tissue anchor in the inferior vena cava. For some applications, implanting the atrial second tissue anchor includes implanting the atrial second tissue anchor within 1 cm of a site on the annulus that circumferentially corresponds to an anteroposterior commissure of the tricuspid valve.

For some applications, implanting the venous first tissue anchor includes implanting the venous first tissue anchor in the superior vena cava. For some applications, implanting the atrial second tissue anchor includes implanting the atrial second tissue anchor within 1 cm of a site on the annulus that circumferentially corresponds to an anteroposterior commissure of the tricuspid valve.

For some applications, the atrial second tissue anchor includes a helical tissue-coupling element and a head.

For some applications:
  implanting includes implanting a pulley system, which (a) is connected to the venous first tissue anchor, the atrial second tissue anchor, and the venous third tissue anchor, and (b) includes a pulley, and
  reducing the size of the tricuspid orifice by tensioning the one or more tethers includes using the pulley system to distribute and transfer forces between the venous first tissue anchor, the atrial second tissue anchor, and the venous third tissue anchor.

For some applications, implanting includes implanting a pulley system, which includes (a) a pulley, which is connected to the atrial second tissue anchor, and (b) a first tether of the one or more tethers, which first tether (i) is connected to the venous first tissue anchor and the venous third tissue anchor, (ii) is moveable through the pulley, and (iii) has a first length, measured between the venous first tissue anchor and the venous third tissue anchor, of at least 15 mm. For some applications, the pulley includes a loop, and tensioning the first tether includes sliding the first tether through the loop. For some applications, a coefficient of kinetic friction between the first tether and the loop is less than 0.5. For some applications, the loop is a closed loop. For some applications, the pulley includes a ring, and tensioning the first tether includes sliding the first tether through the ring. For some applications, a coefficient of kinetic friction between the first tether and the ring is less than 0.5. For some applications, the pulley includes a wheel, and tensioning the first tether includes rotating the wheel by moving the first tether through the pulley.

For some applications, implanting the venous first tissue anchor, the atrial second tissue anchor, the venous third tissue anchor, and the pulley system includes positioning the venous first tissue anchor, the atrial second tissue anchor, the venous third tissue anchor, and the pulley system such that two longitudinal portions of the first tether adjacent to and on opposite sides of the pulley define an angle therebetween of between 5 and 150 degrees.

For some applications:
  the pulley system further includes a second tether of the one or more tethers, which second tether (a) is connected to the pulley and the atrial second tissue anchor, so as to connect the pulley to the atrial second tissue anchor, and (b) has a second length, measured between the atrial second tissue anchor and the pulley, of at least 3 mm, and
  implanting the pulley system further includes implanting the second tether.

For some applications:
  the atrial second tissue anchor includes (a) a tissue-coupling element, and (b) a head,
  the pulley is connected to the head, and
  tensioning the one or more tethers includes tensioning the first tether by fully extending the pulley away from the head, such that a distance between (a) a site on the pulley farthest from the head and (b) a site on the head closest to the pulley, is at least 3 mm.

For some applications, the head is rigid. For some applications, the head includes an interface that is rotatable with respect to the tissue-coupling element. For some applications, the atrial second tissue anchor includes (a) a tissue-coupling element, and (b) a head, which includes the pulley, and implanting the atrial second tissue anchor includes implanting the head. For some applications, the head includes an interface, which (a) includes the pulley and (b) is rotatable with respect to the tissue-coupling element. For some applications, the pulley includes an eyelet. For some applications, the pulley includes a roller. For some applications, the pulley includes a flexible longitudinal member that is connected to the head at two points along the flexible longitudinal member, so as to define a loop longitudinally between the two points. For some applications, the tissue-coupling element is helical.

For some applications, implanting includes implanting a pulley system, which includes (a) a pulley, which is connected to the venous third tissue anchor, and (b) a first tether of the one or more tethers, which first tether (i) is connected to the venous first tissue anchor and the atrial second tissue anchor, (ii) is moveable through the pulley, and (iii) has a first length, measured between the venous first tissue anchor and the atrial second tissue anchor, of at least 15 mm. For some applications, the pulley includes a loop, and tensioning the one or more tethers includes tensioning the first tether by sliding the first tether through the loop. For some applications, a coefficient of kinetic friction between the first tether and the loop is less than 0.5. For some applications, the loop is a closed loop. For some applications, the pulley includes a ring, and tensioning the one or more tethers includes tensioning the first tether by sliding the first tether through the ring. For some applications, a coefficient of kinetic friction between the first tether and the ring is less than 0.5. For some applications, the pulley includes a wheel, and tensioning the one or more tethers includes tensioning the first tether by rotating the wheel by moving the first tether through the pulley.

For some applications, implanting the venous first tissue anchor, the atrial second tissue anchor, the venous third tissue anchor, and the pulley system includes positioning the venous first tissue anchor, the atrial second tissue anchor, the venous third tissue anchor, and the pulley system such that two longitudinal portions of the first tether adjacent to and on opposite sides of the pulley define an angle therebetween of between 5 and 150 degrees.

For some applications:
the pulley system further includes a second tether of the one or more tethers, which second tether (a) is connected to the pulley and the venous third tissue anchor, so as to connect the pulley to the venous third tissue anchor, and (b) has a second length, measured between the venous third tissue anchor and the pulley, of at least 3 mm, and
implanting the pulley system further includes implanting the second tether.

There is additionally provided, in accordance with an application of the present invention, apparatus including a valve-tensioning implant, which includes:
a venous first tissue anchor, which is configured to be implanted in a vein selected from the group of veins consisting of: a superior vena cava and an inferior vena cava;
an atrial second tissue anchor;
a venous third tissue anchor, which is configured to be implanted in a coronary sinus; and
one or more tethers, which connect the venous first tissue anchor, the atrial second tissue anchor, and the venous third tissue anchor.

For some applications, the venous first tissue anchor and the venous third tissue anchor include first and second intraluminal stents, respectively.

For some applications, a greatest outer diameter of the second intraluminal stent is no more than 80% of a greatest outer diameter of the first intraluminal stent, when the first and the second intraluminal stents are unconstrained and fully radially expanded. For some applications, the greatest outer diameter of the second intraluminal stent is no more than 60% of the greatest outer diameter of the first intraluminal stent, when the first and the second intraluminal stents are unconstrained and fully radially expanded.

For some applications, the atrial second tissue anchor includes a helical tissue-coupling element. For some applications, the atrial second tissue anchor includes a helical tissue-coupling element and a head.

For some applications, the valve-tensioning implant further includes a pulley system, which (a) is connected to the venous first tissue anchor, the atrial second tissue anchor, and the venous third tissue anchor, (b) includes a pulley, and (c) is arranged so as to distribute and transfer forces between the venous first tissue anchor, the atrial second tissue anchor, and the venous third tissue anchor.

For some applications, the valve-tensioning implant further includes a pulley system, which includes:
a pulley, which is connected to the atrial second tissue anchor; and
a first tether of the one or more tethers, which first tether (a) is connected to the venous first tissue anchor and the venous third tissue anchor, (b) is moveable through the pulley, and (c) has a first length, measured between the venous first tissue anchor and the venous third tissue anchor, of at least 15 mm.

For some applications, the pulley includes a loop, and the first tether is slidably moveable through the loop. For some applications, a coefficient of kinetic friction between the first tether and the loop is less than 0.5. For some applications, the loop includes a closed loop. For some applications, the pulley includes a ring, and the first tether is slidably moveable through the ring. For some applications, a coefficient of kinetic friction between the first tether and the ring is less than 0.5. For some applications, the pulley includes a wheel.

For some applications, the pulley system further includes a second tether of the one or more tethers, which second tether (a) is connected to the pulley and the atrial second tissue anchor, so as to connect the pulley to the atrial second tissue anchor, and (b) has a second length, measured between the atrial second tissue anchor and the pulley, of at least 3 mm. For some applications, the second length equals at least 10% of the first length. For some applications, the first length is between 30 and 80 mm. For some applications, the second length is between 5 and 8 mm.

For some applications:
the atrial second tissue anchor includes (a) a tissue-coupling element, and (b) a head, and
the pulley is connected to the head such that, when the pulley is fully extended away from the head, a distance between (a) a site on the pulley farthest from the head and (b) a site on the head closest to the pulley, is at least 3 mm.

For some applications, the head is rigid. For some applications, the head includes an interface that is rotatable with respect to the tissue-coupling element. For some applications, the atrial second tissue anchor includes (a) a tissue-coupling element, and (b) a head, which includes the pulley. For some applications, the head includes an interface, which (a) includes the pulley and (b) is rotatable with respect to the tissue-coupling element. For some applications, the pulley includes an eyelet. For some applications, the pulley includes a roller. For some applications, the pulley includes a flexible longitudinal member that is connected to the head at two points along the flexible longitudinal member, so as to define a loop longitudinally between the two points. For some applications, the tissue-coupling element is helical.

For some applications, the valve-tensioning implant further includes a pulley system, which includes:
a pulley, which is connected to the venous third tissue anchor:
a first tether of the one or more tethers, which first tether (a) is connected to the venous first tissue anchor and the atrial second tissue anchor, (b) is moveable through the pulley, and (c) has a first length, measured between the venous first tissue anchor and the atrial second tissue anchor, of at least 15 mm.

For some applications, the pulley includes a loop, and the first tether is slidably moveable through the loop. For some applications, a coefficient of kinetic friction between the first tether and the loop is less than 0.5. For some applications, the loop includes a closed loop. For some applications, the pulley includes a ring, and the first tether is slidably moveable through the ring. For some applications, a coefficient of kinetic friction between the first tether and the ring is less than 0.5. For some applications, the pulley includes a wheel. For some applications, the pulley system further includes a second tether of the one or more tethers, which second tether (a) is connected to the pulley and the venous third tissue anchor, so as to connect the pulley to the venous third tissue anchor, and (b) has a second length, measured between the venous third tissue anchor and the pulley, of at least 3 mm. For some applications, the second length equals at least 10% of the first length. For some applications, the first length is between 30 and 80 mm. For some applications, the second length is between 3 and 8 mm.

For some applications, the apparatus further includes a delivery system, configured to deliver and enable implantation of the valve-tensioning implant, and the delivery system includes at least one catheter shaft.

The present invention will be more fully understood from the following detailed description of applications thereof, taken together with the drawings, in which:

BRIEF DESCRIPTION OF THE DRAWINGS

FIGS. 6A-1 are schematic illustrations of implantations of the valve-tensioning implant of FIG. 4, in accordance with respective applications of the present invention:

FIGS. 8A-H are schematic illustrations of implantations of the valve-tensioning implant of FIG. 7, in accordance with respective applications of the present invention;

FIGS. 9A and 9B are schematic illustrations of a delivery system comprising a multiple-anchor delivery tool, in accordance with respective applications of the present invention; and FIGS. 10A-C are schematic illustrations of a deployment method using the multiple-anchor delivery tool and implant shown in FIG. 9B, in accordance with an application of the present invention;

FIGS. 11A-D are schematic illustrations of a delivery system comprising respective multiple-anchor delivery tools, in accordance with respective applications of the present invention; and FIGS. 12A-C are schematic illustrations of the deployment of a valve-tensioning implant system using the multiple-anchor delivery tool of FIG. 11A, in accordance with an application of the present invention.

DETAILED DESCRIPTION OF APPLICATIONS

Figure 1:
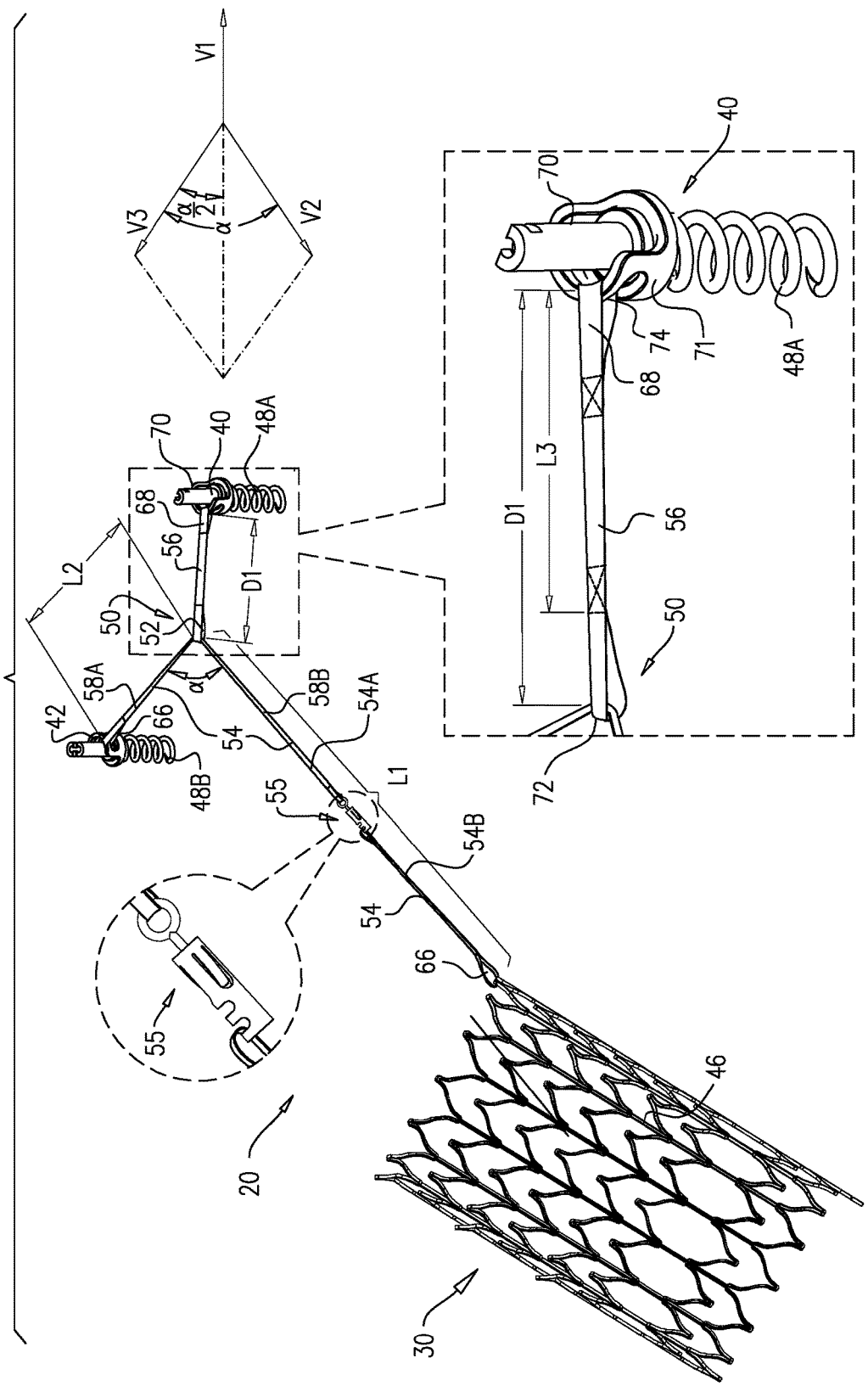
FIG. 1 is a schematic illustration of a valve-tensioning implant, in accordance with an application of the present invention.

FIG. 1 is a schematic illustration of a valve-tensioning implant system 20, in accordance with an application of the present invention. Valve-tensioning implant system 20 is configured to repair an atrioventricular valve of a subject (e.g., a tricuspid valve), using tension applied between multiple anchors of the implant. Typically, repair of the atrioventricular valve facilitates a reduction in atrioventricular valve regurgitation by altering the geometry of the atrioventricular valve and/or by altering the geometry of the wall of the right or left atrium of a heart of the subject.

For some applications, valve-tensioning implant system 20 comprises a first venous tissue anchor 30, such as exactly one first venous tissue anchor 30. First venous tissue anchor 30 is configured to be implanted at an implantation site upstream of the atrioventricular valve. For example, for applications in which the atrioventricular valve is the tricuspid valve, first venous tissue anchor 30 is typically configured to be implanted in a vein selected from the group of veins consisting of: a superior vena cava (SVC) 110 (such as described hereinbelow with reference to FIGS. 3E-H, 3M, 3O, and 3Q), an inferior vena cava (IVC) 80 (such as described hereinbelow with reference to FIGS. 3A-D, 3I, 3L, and 3P), and a coronary sinus 115 (such as described hereinbelow with reference to FIGS. 3J-M). Valve-tensioning implant system 20 further comprises second and third atrial tissue anchors 40 and 42. For some applications, valve-tensioning implant system 20 comprises exactly two atrial tissue anchors, which consist of second and third atrial tissue anchors 40 and 42.

Valve-tensioning implant system 20 further comprises a pulley system 44, which comprises:
 a pulley 50, which is connected (e.g., permanently fixed) to second atrial tissue anchor 40; and
 a tether 54, which is connected (e.g., permanently fixed) to first venous tissue anchor 30 and third atrial tissue anchor 42, and is moveable through pulley 50.

Tether 54 comprises an elongate flexible element, such as a cord, suture, or band. Typically, tether 54 has a high tensile strength and low friction, in order to enable the tether to apply tension, as described hereinbelow. Typically, tether 54 has a length, measured between first venous tissue anchor 30 and third atrial tissue anchor 42, of at least 15 mm, no more than 200 mm, and/or between 15 and 200 mm, such at least 30 mm, no more than 120 mm, and/or between 30 and 120 mm. The length equals the sum of (a) a first sub-length L1 of a first portion of the tether between first venous tissue anchor 30 and pulley 50 and (b) a second sub-length L2 of a second portion of the tether between pulley 50 and third atrial tissue anchor 42, (First and second sub-lengths L1 and L2 are not fixed, because tether 54 is both moveable through pulley 50 as well as rotatable around the pivot point; however, the sum of the two sub-lengths is fixed.) Because tether 54 typically has a high tensile strength, the length thereof does not vary based on the particular disposition of the tether at any given point in time. In other words, the length of the tether does not depend on the amount of force applied to it. For some applications, tether 54 is configured so as to define an anchor-fixing loop 66, which passes through a corresponding interface (e.g., defined by struts of the stent) on first venous tissue anchor 30, so as to connect (e.g., permanently fix) the tether to the first venous tissue anchor.

For some applications, tether 54 comprises two separate sections 54A and 54B, which may be connected by an intraluminal locking mechanism 55 that comprises coupling elements (e.g., male and female coupling elements), which are connected during the implantation procedure, such as in order to allow implantation of first venous tissue anchor 30 with a separate catheter delivery system, such as described in US Patent Application Publication 2013/0018459, which is assigned to the assignee of the present application, and is incorporated herein by reference, such as with reference to FIGS. 20-32 thereof.

Reference is made to FIGS. 2A-D, which are schematic illustrations of several configurations of pulley 50, in accordance with respective applications of the present invention. As used in the present application, including in the claims, a "pulley" is an element that transfers force along a tether, changing a direction of the force without substantially changing a magnitude of the force, while the tether moves through the pulley. As used herein, a pulley need not comprise a wheel, as is common in conventional pulleys. For some applications, a wheel is not necessary because the movement required during the cardiac cycle is reciprocal (back-and-forth) in nature, and limited in magnitude, about a few millimeters in each direction. It is noted that at some time after implantation, tissue growth may inhibit or entirely obstruct the tether's movement through the pulley, thereby disabling the pulley's "pulley" functionality. As used in the present application, including the claims, the feature that the tether is moveable through the pulley characterizes the pulley system at least at the time of implantation, but not necessarily after implantation.

Figure 2A:
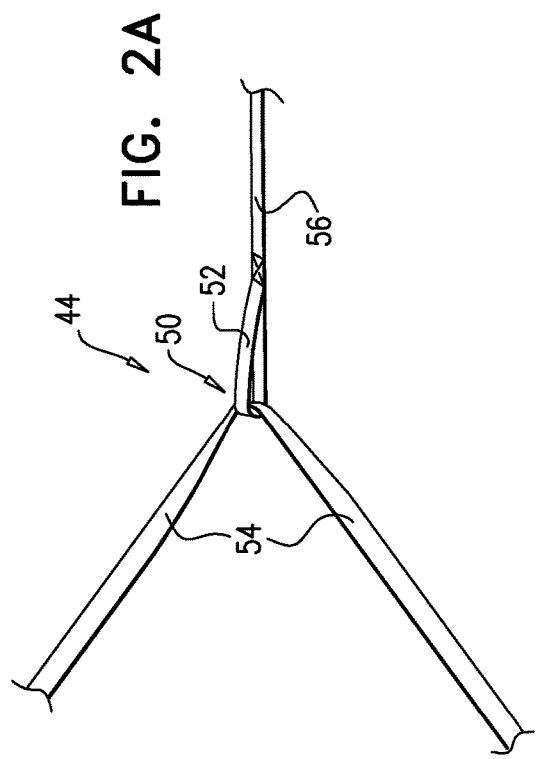
FIGS. 2A-D are schematic illustrations of several configurations of a pulley of the valve-tensioning implant of FIG. 1, in accordance with respective applications of the present invention.
Figure 2B:
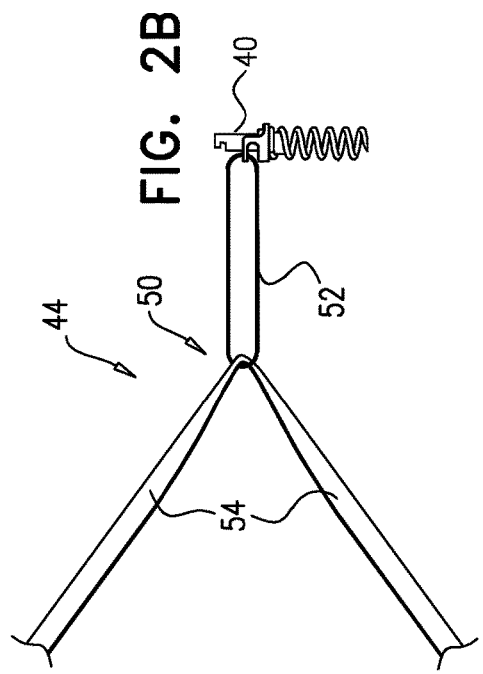

For some applications, as shown in FIGS. 2A and 2B (and in FIG. 1), pulley 50 comprises a loop 52, through which tether 54 is slidably moveable. Typically, a coefficient of kinetic friction between the tether and the loop is less than 0.5, such as less than 0.2, e.g., less than 0.1. For some applications, as shown in FIGS. 1 and 2A, loop 52 comprises a closed loop; in other words, the ends of the loop are joined together. For other applications, as shown in FIG. 2B, loop 52 comprises an open loop; both ends of the cord that defines the loop are connected (e.g., permanently fixed) to second atrial tissue anchor 40, but not to one another. In other words, pulley 50 comprises a flexible longitudinal member that is connected (e.g., permanently fixed) to the head of anchor 40 at two points along the flexible longitudinal member, so as to define loop 52 longitudinally between the two points.

Figure 2C:
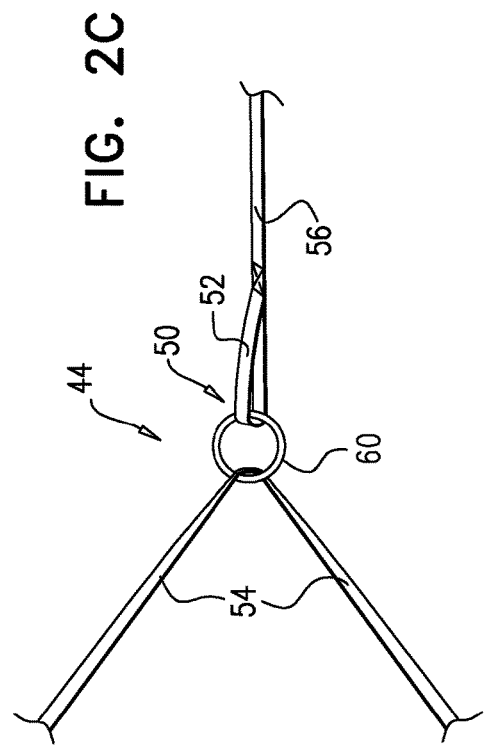
Figure 2D:
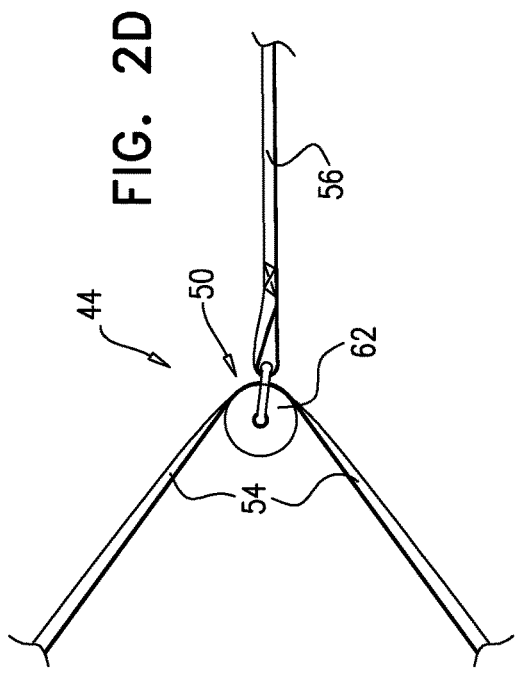

For some applications, such as shown in FIG. 2C, pulley 50 comprises a ring 60, through which tether 54 is slidably moveable. Typically, a coefficient of kinetic friction between tether 54 and ring 60 is less than 0.5, such as less 0.2, e.g., less than 0.1. For some applications, such as shown in FIG. 2D, pulley 50 comprises a wheel 62 on an axle that supports movement of tether 54 along the wheel's circumference. Wheel 62 typically is shaped so as to define a groove between two flanges around its circumference, as is well-known in the pulley art. Pulley 50 may alternatively comprise an eyelet or a roller, such as described hereinbelow with reference to FIGS. 4 and 5A-B.

Reference is again made to FIG. 1. For some applications, first venous tissue anchor 30 comprises an intraluminal stent 46. The stent is configured to be implanted in the vein by applying an outward radial force to the wall of the vein. Typically, the stent is configured to self-expand. For example, the stent may comprise a shape-memory alloy, such as Nitinol. Alternatively, the stent comprises a deformable metal, and is expanded by a tool, such as a balloon. For some applications, stent 46 comprises a plurality of interconnected superelastic metallic struts, arranged so as to allow crimping the stent into a relatively small diameter (typically less than 8 mm) catheter, while allowing deployment to a much larger diameter (typically more than 20 mm) in the vein, while still maintaining radial force against the tissue of the wall of the vein, in order to anchor stent 46 to the wall of the vein by friction. Typically, the stent is configured to not penetrate tissue of the wall of the vein. For some applications, stent 46 implements techniques described in U.S. Provisional Application 61/783,224, filed Mar. 14, 2013, which is assigned to the assignee of the present application and is incorporated herein by reference.

For some applications, second and third atrial tissue anchors 40 and 42 comprise respective helical tissue-coupling elements 48A and 48B, which puncture and screw into the cardiac muscle tissue. For some applications, second and third atrial tissue anchors 40 and 42 implement techniques described in U.S. Provisional Application 61/750,427, filed Jan. 9, 2013. Alternatively, each of second and third atrial tissue anchors 40 and 42 comprises a clip, jaws, or a clamp which grips and squeezes a portion of cardiac muscle tissue and does not puncture the cardiac muscle tissue.

For some applications, as shown in FIG. 1, tether 54 is a first tether 54, and the length of first tether 54 is a first length. Pulley system 44 further comprises a second tether 56, which is connected (e.g., permanently fixed) to pulley 50 and second atrial tissue anchor 40, so as to fix pulley 50 to second atrial tissue anchor 40. Second tether 56 comprises an elongate flexible element, such as a cord, a suture, or a band (e.g., a textile band). Typically, second tether 56 has a high tensile strength. Typically, second tether 56 has a second length L3, measured between second atrial tissue anchor 40 and pulley 50, of at least 3 mm, no more than 20 mm, and/or between 3 and 20 mm, such as at least 5 mm, no more than 8 mm, and/or between 5 and 8 mm. Because second tether 56 typically has a high tensile strength, the length thereof does not vary based on the particular disposition of the second tether at any given point in time. In other words, the length of the second tether does not depend on the tensile forces applied to it. For some applications, the second length equals at least 10% of the first length, no more than 50% of the first length, and/or between 10% and 50% of the second length, such as at least 20% of the first length, no more than 40% of the second length, and/or between 20% and 40% of the second length. For some applications, second tether 56 is configured so as to define an anchor-fixing loop 68, which passes through a corresponding interface on second atrial tissue anchor 40, so as to connect (e.g., permanently fix) the second tether to the second atrial tissue anchor.

For some applications, second atrial tissue anchor 40 comprises (a) tissue-coupling element 48A (which is optionally helical) and (b) a head 70. Pulley 50 is connected (e.g., permanently fixed) to head 70 such that, when pulley 50 is fully extended away from the head, a distance D1 between (a) a site 72 on pulley 50 farthest from head 70 and (b) a site 74 on head 70 closest to pulley 50, is at least 3 mm (e.g., at least 5 mm), no more than 40 mm, and/or between 3 and 40 mm or between 5 and 40 mm. For some applications, distance D1 equals at least 10% of the length of tether 54, no more than 50% of the length of tether 54, and/or between 10% and 50% of the length of tether 54. Typically, head 70 comprises a tether interface 71, to which second tether 56 is connected (such as by anchor-fixing loop 68). Typically, tether interface 71 is rotatable with respect to tissue-coupling element 48A. For some applications, head 70 is rotatable with respect to tissue-coupling element 48A, so that tether interface 71 is rotatable with respect to tissue-coupling element 48A. Alternatively, tether interface 71 is rotatable with respect to head 70 (which may be rotationally fixed with respect to tissue-coupling element 48A), such that tether interface 71 is rotatable with respect to tissue-coupling element 48A.

Figure 3C:
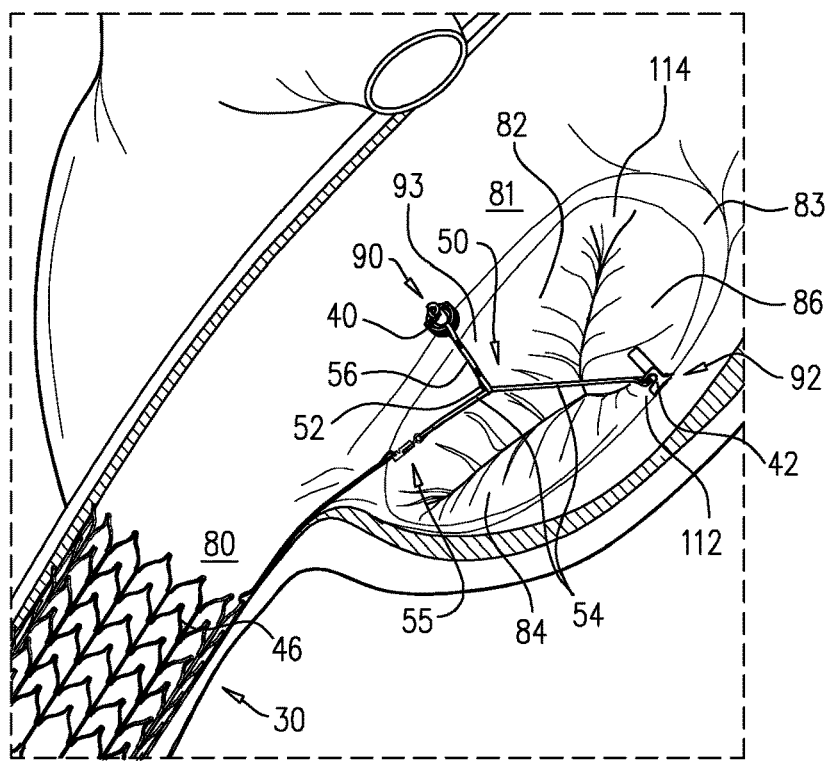
FIGS. 3A-Q are schematic illustrations of implantations of the valve-tensioning implant of FIG. 1, in accordance with respective applications of the present invention.
Figure 3D:
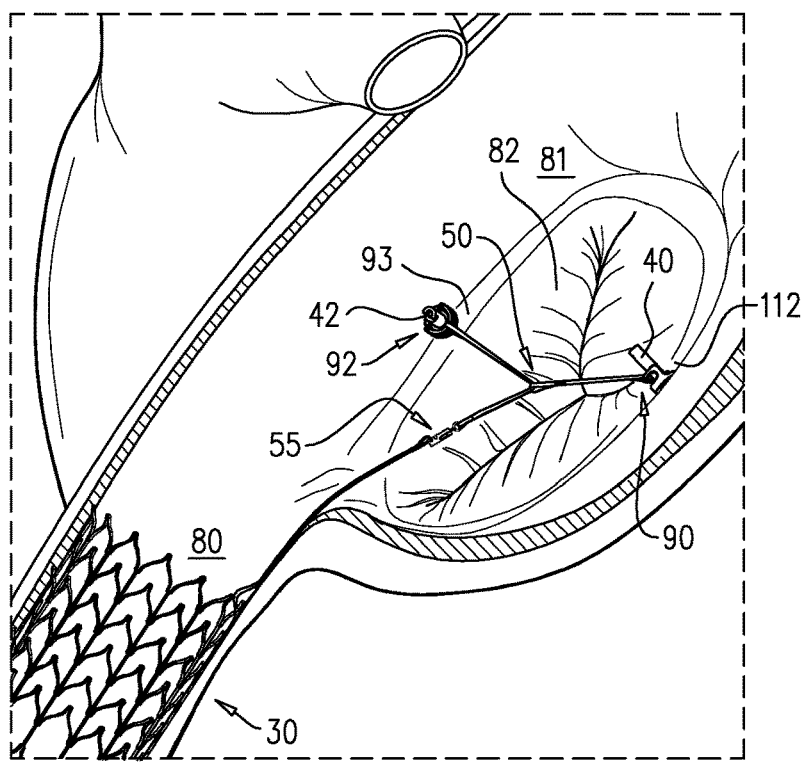
Figure 3E:
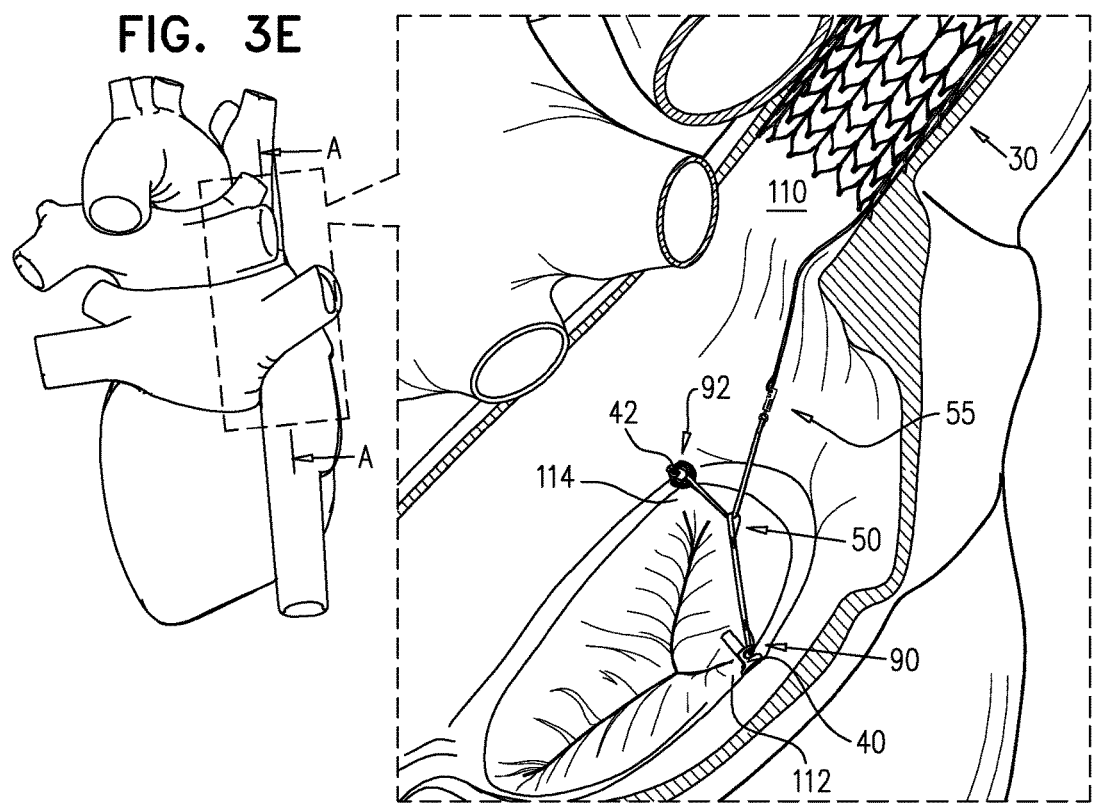
Figure 3F:
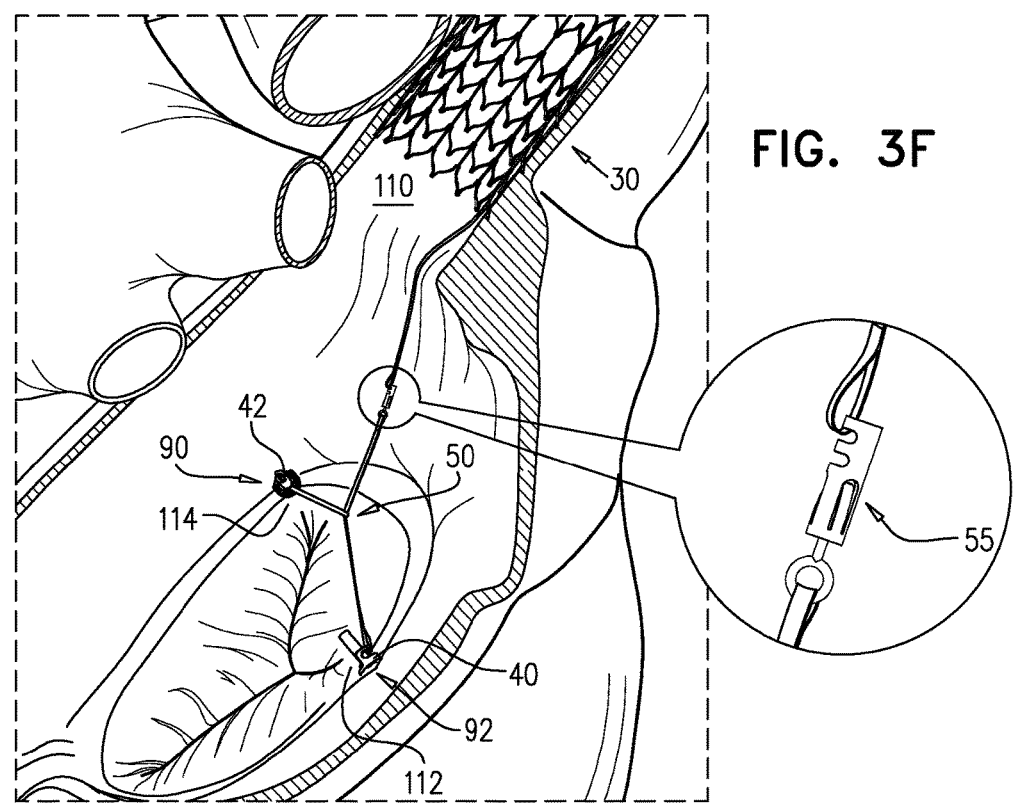
Figure 3I:
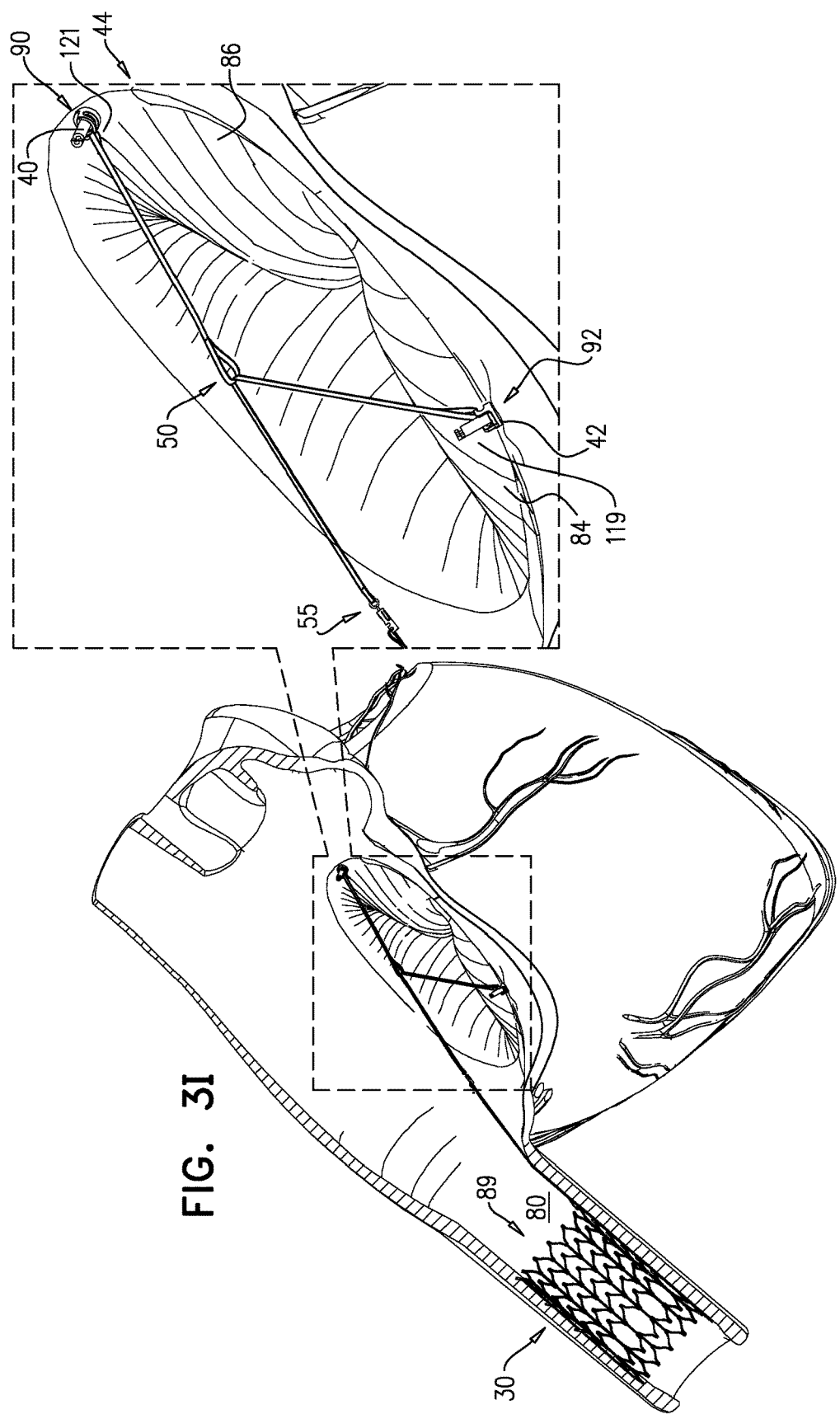
Figure 3K:
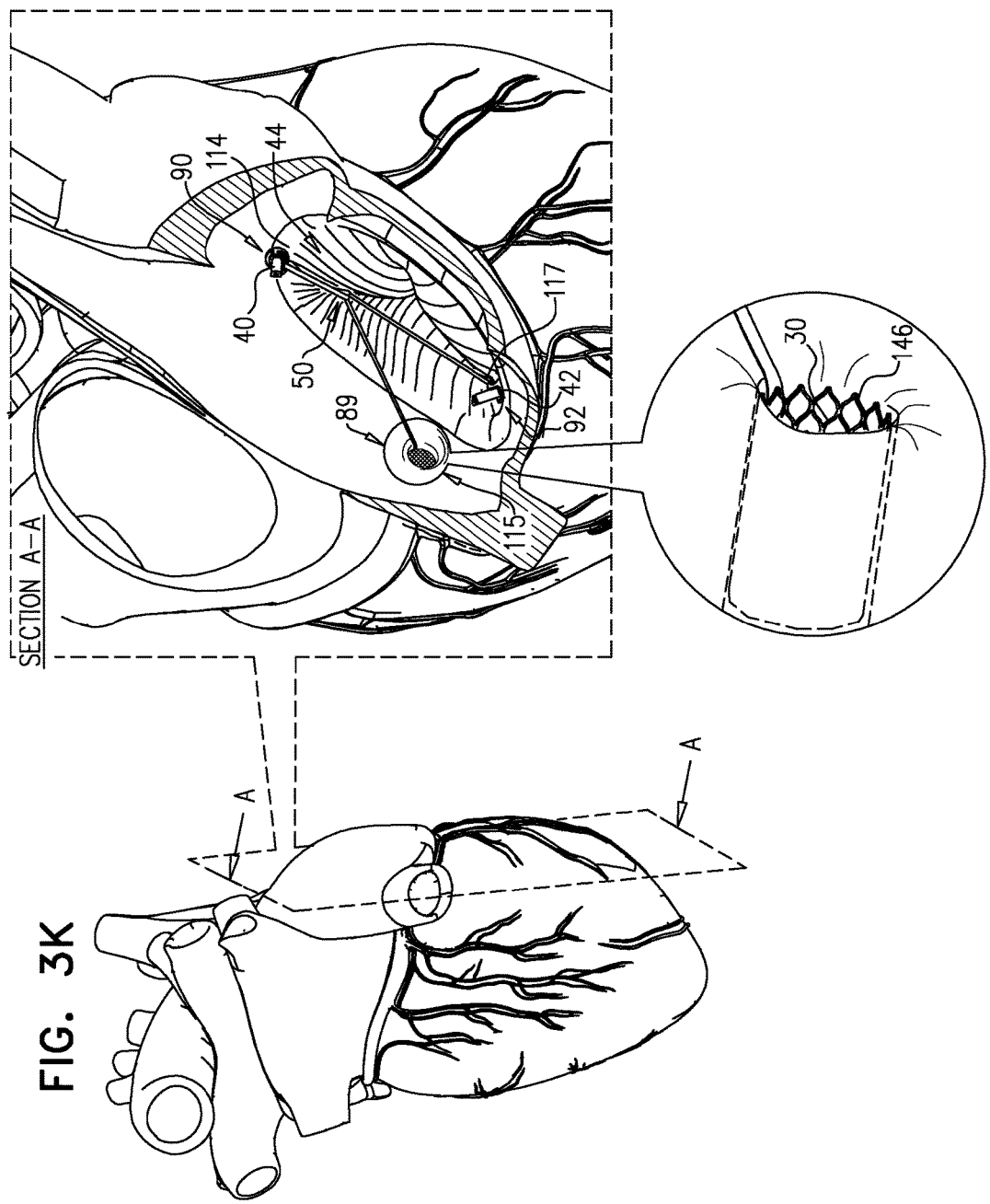
Figure 3L:
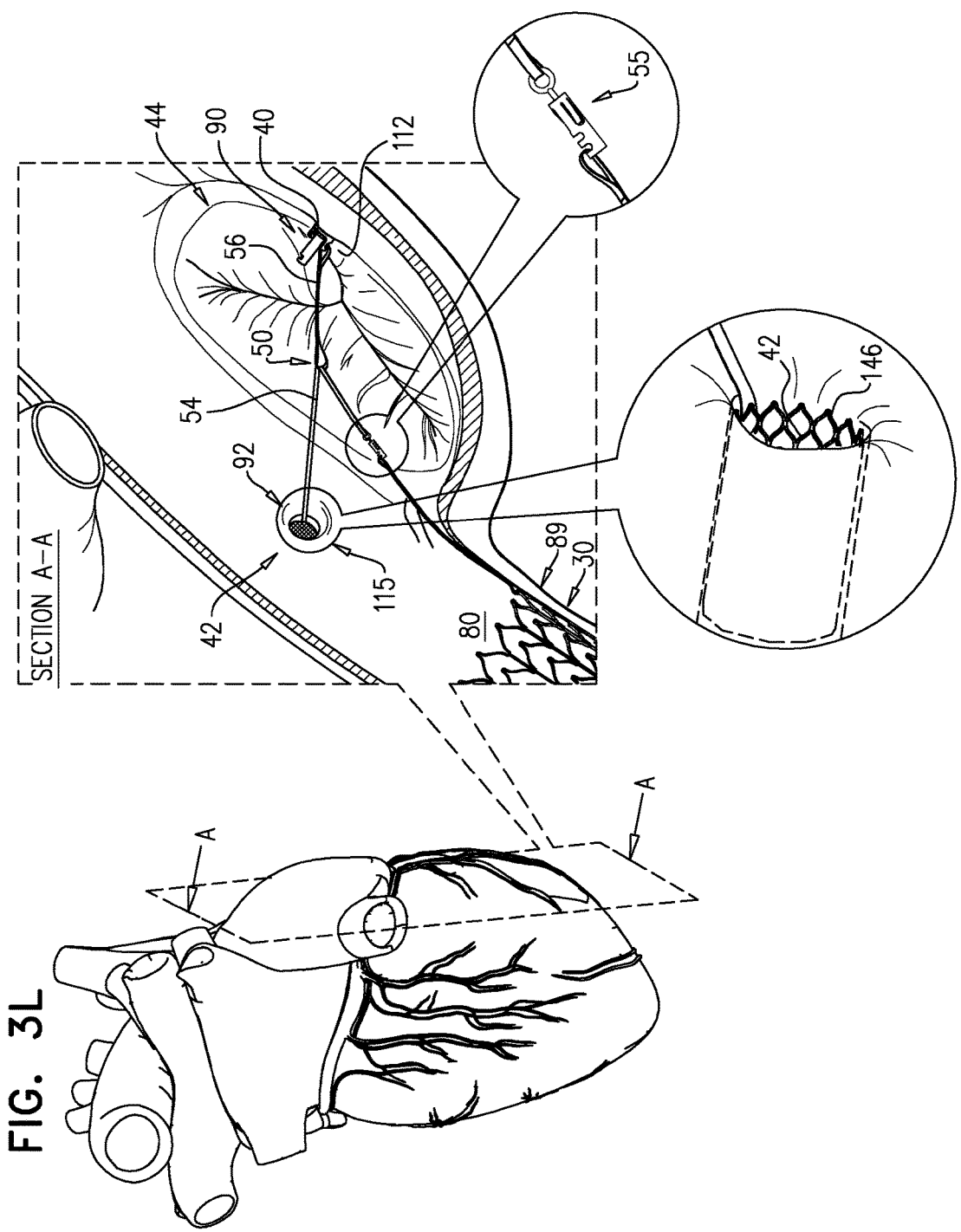
Figure 3M:
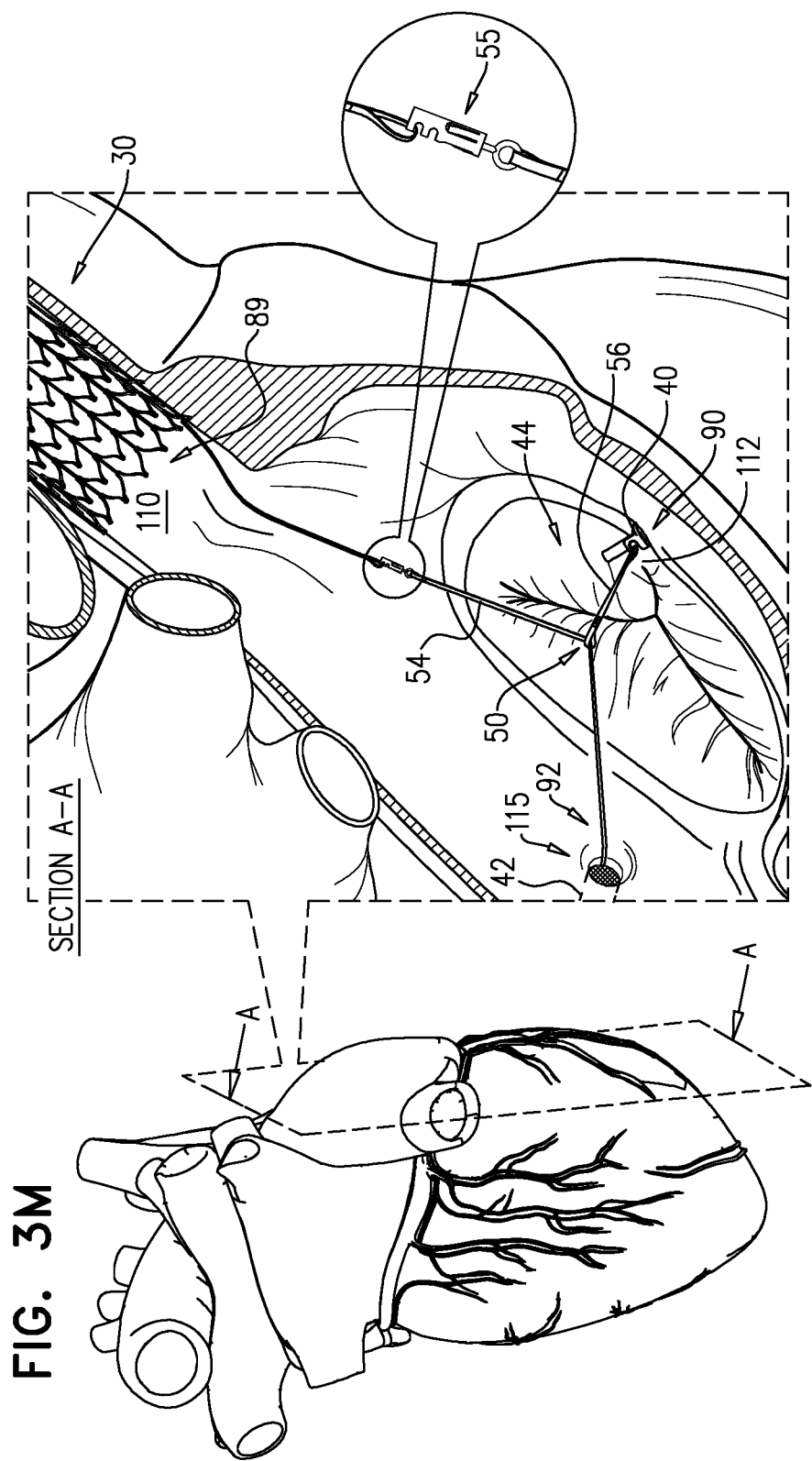
Figure 30:
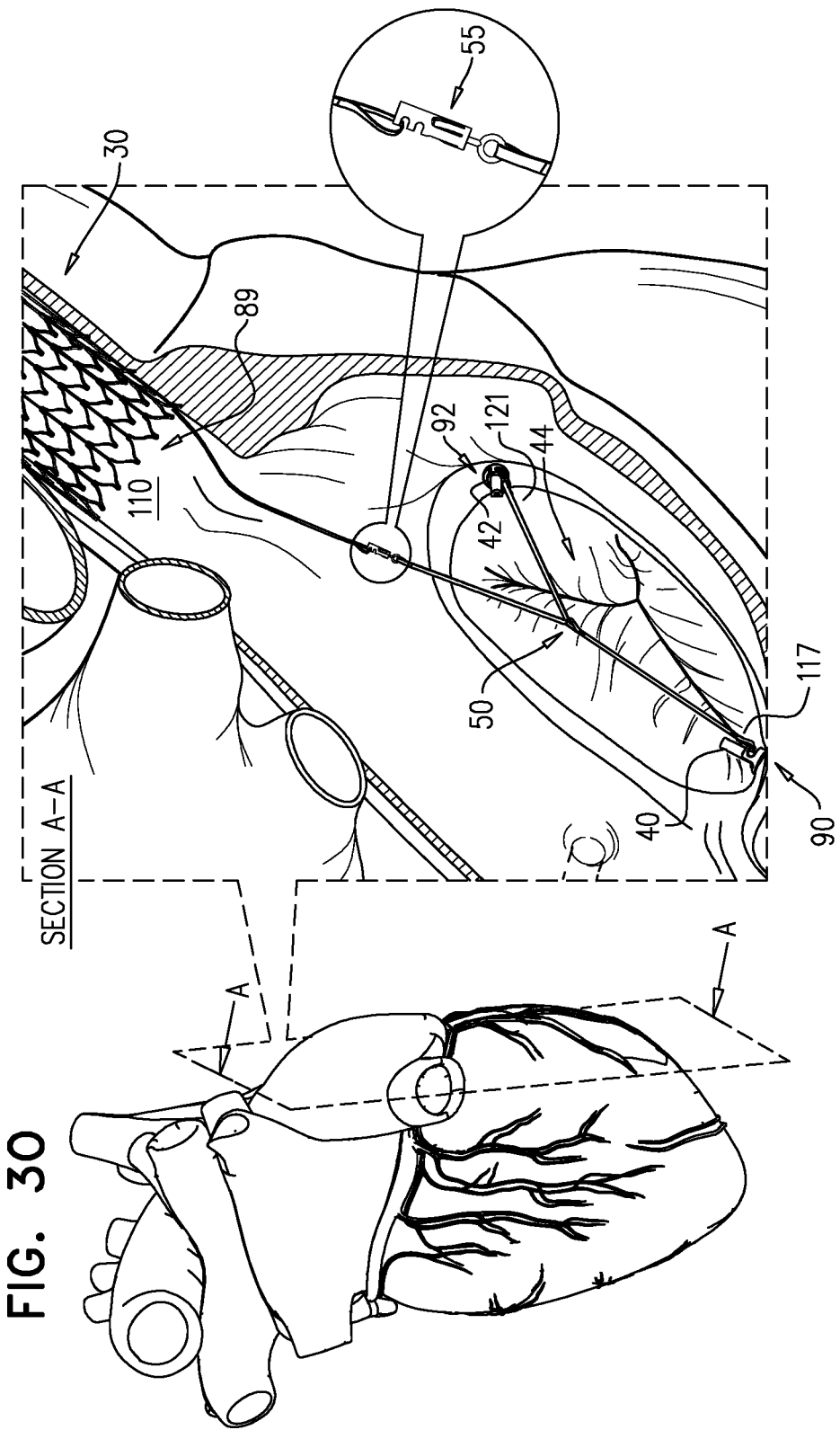
Figure 3P:
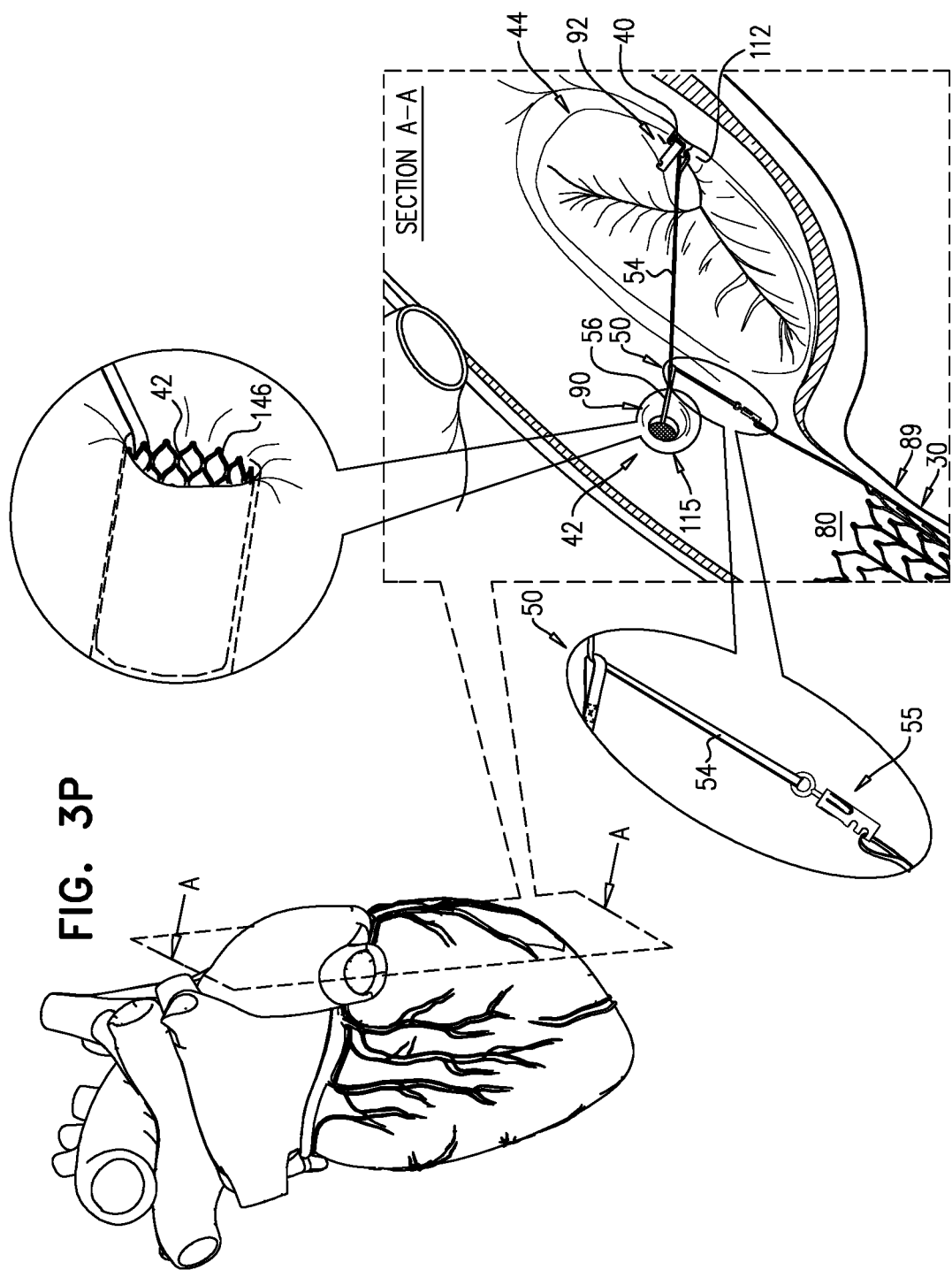
Figure 3Q:
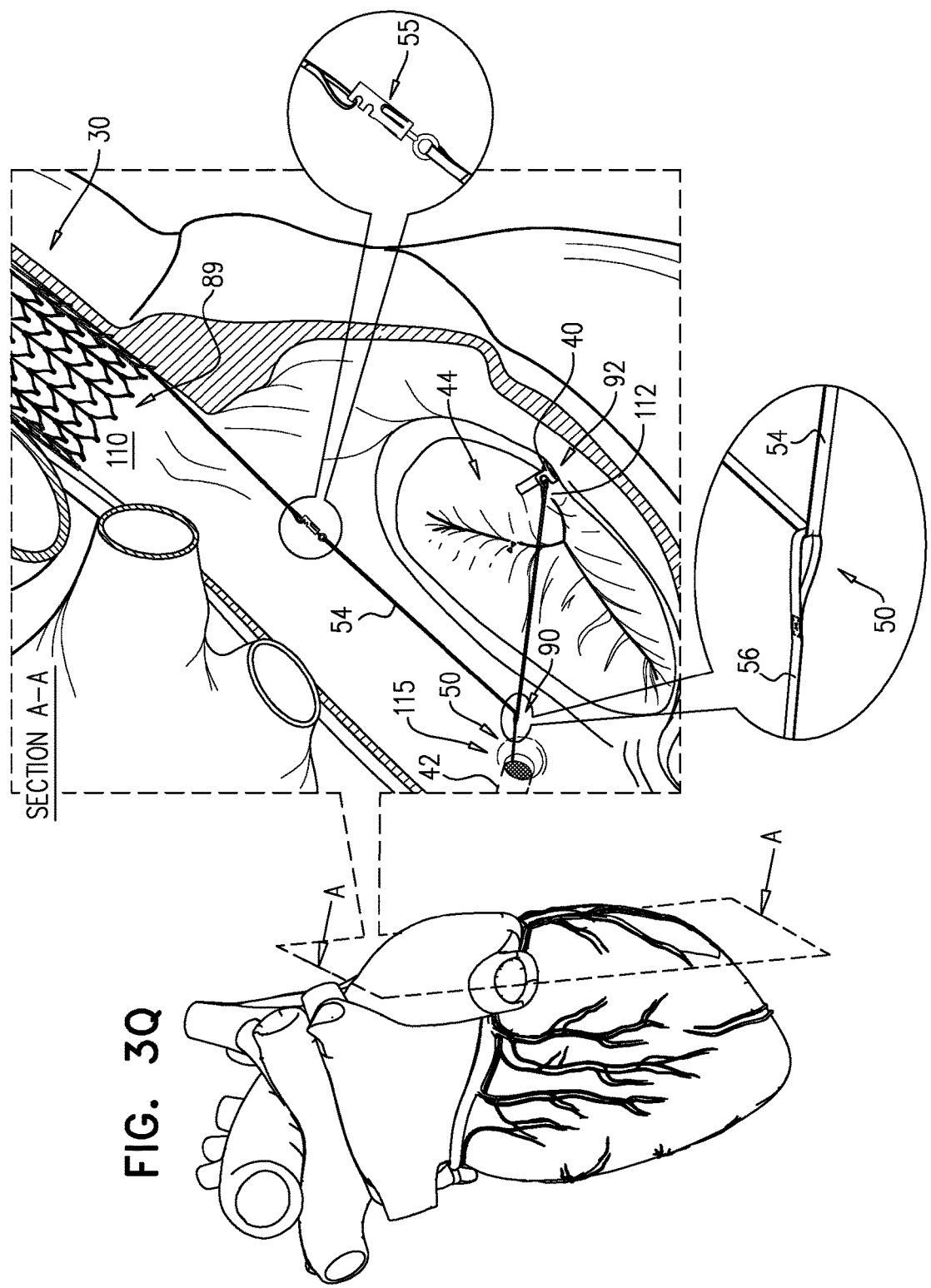

Reference is now made to FIGS. 3A-Q, which are schematic illustrations of implantations of valve-tensioning implant system 20, in accordance with respective applications of the present invention. The implantations are typically performed transvascularly, using a delivery system comprising one or more catheters introduced with the aid of a guidewire, through vasculature of the subject, such as (a) via the femoral vein, through inferior vena cava 80, and into a right atrium 81, (b) via the basilic vein, through the subclavian vein through superior vena cava 110, and into right atrium 81, or (c) via the external jugular vein, through the subclavian vein through superior vena cava 110, and into right atrium 81. (Right atrium 81 includes a septal leaflet 82, a posterior leaflet 84, and an anterior leaflet 86.) The procedure is typically performed with the aid of imaging, such as fluoroscopy, transesophageal echo, and/or echocardiography. The procedure may be performed using techniques described in US Patent Application Publication 2012/0035712, which is assigned to the assignee of the present application and is incorporated herein by reference, with reference to FIGS. 1A-D thereof, mutatis mutandis, and/or using techniques described hereinbelow with reference to FIGS. 9A-B, 10A-C, 11A-D, and/or 12A-C, mutatis mutandis.

Second and third atrial tissue anchors 40 and 42, e.g., exactly second and third atrial tissue anchors 40 and 42, are implanted at respective different second and third atrial sites 90 and 92, each of which sites is selected from the group of sites consisting of: an annulus 83 of a tricuspid valve 78, and a wall of right atrium 81 of the heart above annulus 83. For applications in which second and third atrial tissue anchors 40 and 42 comprise respective helical tissue-coupling elements 48A and 48B, the helical tissue-coupling elements are rotated into tissue at the sites, respectively.

First venous tissue anchor 30 is implanted at a first site 89 in a vein selected from the group of veins consisting of: superior vena cava 110 (as shown, for example, in FIGS. 3E-H, 3M, 3O, and 3Q), inferior vena cava 80 (as shown, for example, in FIGS. 3A-D, 3I, 3L, and 3P), and coronary sinus 115 (as shown, for example, in FIGS. 3J-K). For applications in which first venous tissue anchor 30 comprises intraluminal stent 46, the stent is expanded in the selected vein in order to anchor the stent to the wall of the vein by the outward radial force applied by the stent. (As used herein, including in the claims, the labels "first," "second," and "third" of first, second, and third sites 89, 90, and 92, and of first, second, and third tissue anchors 30, 40, and 42, are to be understood only as convenient references to distinguish the sites and anchors from one another, and are not to be understood as implying or requiring any order of implantation or of other properties of the sites or anchors.)

For applications in which first venous tissue anchor 30 is implanted in superior vena cava 110 or inferior vena cava 80, intraluminal stent 46 typically has a greatest outer diameter of between 25 and 55 mm, when unconstrained and fully radially expanded, i.e., no forces are applied to the stent by a delivery tool, walls of a blood vessel, or otherwise. For applications in which first venous tissue anchor 30 is implanted in coronary sinus 115, intraluminal stent 46 typically has a greatest outer diameter of between 5 and 20 mm, when unconstrained and fully radially expanded (the stent may somewhat enlarge the coronary sinus).

Once pulley system 44 has been implanted, a size of a tricuspid orifice is reduced by tensioning tether 54, so as to reduce regurgitation. For some applications in which second atrial tissue anchor 40 comprises tissue-coupling element 48A and head 70, as described hereinabove with reference to FIG. 1, tensioning tether 54 comprise fully extending pulley 50 away from head 70, such that distance D1, described hereinabove, between (a) site 72 on pulley 50 farthest from head 70 and (b) site 74 on head 70 closest to pulley 50, is at least 3 mm (e.g., at least 5 mm), no more than 40 mm, and/or between 3 and 40 mm or between 5 and 30 mm.

Pulley system 44 enables the controlled, uneven distribution of forces on tissue at first, second, and third implantation sites 89, 90, and 92. As labeled in FIG. 1, a force vector V1 on the tissue at second implantation site 90, which is connected (e.g., permanently fixed) to pulley 50 by second atrial tissue anchor 40, equals the vector sum of force vectors V2 and V3 acting on tissue at first and third implantation sites 89 and 92, respectively, which are connected (e.g., permanently fixed) to tether 54 by first venous tissue anchor 30 and third atrial tissue anchor 42, respectively. As a result, the forces acting on first and third implantation sites 89 and 92 are less than the force acting on second implantation site 90 (to which the pulley is fixed).

This controlled distribution of forces may be particularly beneficial if, for example:
- second implantation site 90 (to which the pulley is fixed) is located in a region of tissue which is thicker or stronger than first and third implantation sites 89 and 92. For example, tissue of the septum between the ventricles is thicker and stronger than the atrium wall and the vena cava wall;
- the anchoring mechanism of the anchor to which the pulley is connected anchors using mechanical purchase, e.g., using a helical anchor, while the anchoring mechanism of at least one of the other anchoring points (e.g., first implantation site 89) is friction based, e.g., using an intraluminal stent; and/or
- the force vectors acting on first implantation site 89 and second implantation site 90 (to which the pulley is fixed) are aligned along a preferable direction which causes constriction of the tricuspid valve in a more favorable manner than tensioning towards third implantation site 92 alone. For example, the sites may be selected apply the maximum force on the implantation site that is desired to be moved.

The tissue anchors and pulley system 44 are arranged such that the vector sum of the forces on all of the implantation sites is zero, and the force vector on second implantation site 90 (to which the pulley is fixed) is the vector sum of the forces acting on first and third implantation sites 89 and 92. The scalar force acting on first and third implantation sites 89 and 92 depends on an angle α (alpha) (labeled in FIG. 1) formed by tether 54 at pulley 50, and may be expressed by the following equation:

$$|F_s| = \frac{|F_p|}{2\cos(\frac{\alpha}{2})} \quad \text{(Equation 1)}$$

in which:
$F_s$ is the force acting on each of the first and third implantation sites 89 and 92;
$F_p$ is the force acting on second implantation site 90 (to which the pulley is fixed); and
α (alpha) is the angle formed by tether 54 at pulley 50 (sometimes referred to in the pulley art as the "included angle").

In accordance with this equation, the force acting on each of first and third implantation sites 89 and 92 is less than the force acting on second implantation site 90 (to which the pulley is fixed). The force acting on each of first and third implantation sites 89 and 92 is approximately 50% of the force acting on second implantation site 90 when angle α (alpha) is 45 degrees or less. (Angle α (alpha) is defined by two longitudinal portions 58A and 58B (labeled in FIG. 1) of tether 54 adjacent to and on opposite sides of pulley 50.) For some applications, in order to achieve the desired force distribution among the implantation sites, when implanting the tissue anchors, the surgeon positions the tissue anchors and pulley system 44 such that angle α (alpha) is acute (less than 90-degree), typically between 40 and 85 degrees, typically as close as possible to 45 degrees or lower.

For some applications in which pulley system 44 further comprises second tether 56, a kit is provided that comprises a plurality of pulleys 50 connected (e.g., permanently fixed) to a respective plurality of second tissue anchors 40 by respective second tethers 56 having different respective lengths. The surgeon selects an appropriate pulley/second tether/second anchor assembly based on the particular anatomy of the subject, in order to achieve a desired angle α (alpha). The length of the second tether affects the location of the pulley. Alternatively, valve-tensioning implant system 20 comprises a single pulley, a single second tether, and a single second anchor, and the second tether has an adjustable length, which the surgeon can set before and/or during the implantation procedure as appropriate for the particular anatomy of the subject. Either option provides for an adjustable distance D1, as described hereinabove with reference to FIG. 1.

The following table sets forth exemplary combinations of first implantation site 89 and anatomical markers for second and third implantation sites 90 and 92, and figures that show exemplary deployments at these sites. These sites are listed by way of example and not limitation; the surgeon typically selects the exact sites based on the subject's individual needs and anatomy. Each of second and third implantation sites 90 and 92 is located within 1 cm of the site on the annulus that circumferentially corresponds to the respective anatomical marker (i.e., is at the same angular location or "o'clock" as the respective anatomical marker). The direction of the 1 cm from the site on the annulus may be either circumferentially (i.e., clockwise or counterclockwise) around the annulus, up the wall of right atrium 81 above annulus 83, or a combination of circumferentially around the annulus and up the wall of the atrium. For example, as shown in FIG. 3B, anteroposterior commissure 112 is near, but not on, the annulus, and second tissue anchor 40 is shown implanted at second implantation site 90, which is at the site on the annulus that circumferentially corresponds to this commissure. Second implantation site 90 could also be up to 1 cm clockwise or counterclockwise around the annulus from this site on the annulus, up to 1 cm up the wall of the atrium, or a combination of these two directions.

Typically, the surgeon uses the anatomical markers to find the exact locations of second and third implantation sites 90 and 92, which are within 1 cm of the anatomical markers, as described above. For example, the commissures are easily detectable using imaging, and thus represent good anatomical markers. However, the commissures are not appropriate for implantation (because they are too delicate), so, in this example, the anchors are implanted on the annulus or up the wall of the atrium, within 1 cm from the commissure.

TABLE 1

| First implantation site 89 | Second implantation site 90 (pulley) anatomical marker | Third implantation site 92 anatomical marker | FIG. |
| --- | --- | --- | --- |
| Inferior vena cava 80 | Septoanterior commissure 114 | Anteroposterior commissure 112 | FIG. 3A |
| Inferior vena cava 80 | Anteroposterior commissure 112 | Septoanterior commissure 114 | FIG. 3B |
| Inferior vena cava 80 | A circumferential middle 93 of septal leaflet 82 | Anteroposterior commissure 112 | FIG. 3C |
| Inferior vena cava 80 | Anteroposterior commissure 112 | Circumferential middle 93 of septal leaflet 82 | FIG. 3D |
| Superior vena cava 110 | Anteroposterior commissure 112 | Septoanterior commissure 114 | FIG. 3E |
| Superior vena cava 110 | Septoanterior commissure 114 | Anteroposterior commissure 112 | FIG. 3F |
| Superior vena cava 110 | Anteroposterior commissure 112 | Circumferential middle 93 of septal leaflet 82 | FIG. 3G |
| Superior vena cava 110 | Circumferential middle 93 of septal leaflet 82 | Anteroposterior commissure 112 | FIG. 3H |
| Inferior vena cava 80 | A circumferential middle 121 of anterior leaflet 86 | A circumferential middle 119 of posterior leaflet 84 | FIG. 3I |
| Coronary sinus 115 | Anteroposterior commissure 112 | Septoanterior commissure 114 | FIG. 3J |
| Coronary sinus 115 | Septoanterior commissure 114 | A septopostenor commissure 117 | FIG. 3K |
| Inferior vena cava 80 | Anteroposterior commissure 112 | Coronary sinus 115 | FIG. 3L |
| Superior vena cava 110 | Anteroposterior commissure 112 | Coronary sinus 115 | FIG. 3M |
| Coronary sinus 115 | Circumferential middle 121 of anterior leaflet 86 | Circumferential middle 119 of posterior leaflet 84 | FIG. 3N |
| Superior vena cava 110 | Septoposterior commissure 117 | Circumferential middle 121 of anterior leaflet 86 | FIG. 3O |
| Inferior vena cava 80 | Coronary sinus 115 | Anteroposterior commissure 112 | FIG. 3P |
| Superior vena cava 110 | Coronary sinus 115 | Anteroposterior commissure 112 | FIG. 3Q |

Thus, for some applications, an implantation method comprises implanting first venous tissue anchor 30 at first implantation site 89 in inferior vena cava 80. For some applications, second atrial tissue anchor 40 is implanted at second implantation site 90 which is located within 1 cm of a site on the annulus that circumferentially corresponds to circumferential middle 93 of septal leaflet 82 of tricuspid valve 78, and third atrial tissue anchor 42 is implanted at third implantation site 92 which is located within 1 cm of a site on the annulus that circumferentially corresponds to anteroposterior commissure 112 of tricuspid valve 78. Alternatively, for some applications, second atrial tissue anchor 40 is implanted at second implantation site 90 which is located within 1 cm of a site on the annulus that circumferentially corresponds to septoanterior commissure 114 of tricuspid valve 78, and third atrial tissue anchor 42 is implanted at third implantation site 92 which is located within 1 cm of a site on the annulus that circumferentially corresponds to anteroposterior commissure 112 of tricuspid valve 78.

Reference is again made to FIGS. 3L, 3M, 3P, and 3Q. For some applications, third tissue anchor 42 comprises a venous third tissue anchor 42, rather than an atrial third tissue anchor. For these applications, venous third tissue anchor 42 typically comprises an intraluminal stent 146 that is configured to be implanted in coronary sinus 115. Intraluminal stent 146 typically has a greatest outer diameter of at least 10 mm, no more than 20 mm, and/or between 10 to 20 mm, when unconstrained and fully radially expanded. For some applications, the greatest outer diameter of (second) intraluminal stent 146 is less than (such as less than 80% of, e.g., less than 60% of) the greatest outer diameter of (first) intraluminal stent 46, when both stents are unconstrained and fully radially expanded.

For some of these applications, such as shown in FIGS. 3L and 3M, atrial second tissue anchor 40 is implanted at second implantation site 90, and venous third tissue anchor 42 is implanted at third implantation site 92 (which is coronary sinus 115). Pulley 50 is connected to atrial second tissue anchor 40. First tether 54 (i) is connected to venous first tissue anchor 30 and venous third tissue anchor 42, (ii) is moveable through pulley 50, and (iii) typically has a first length, measured between venous first tissue anchor 30 and venous third tissue anchor 42, of at least 15 mm, such as at least 30 mm. For some applications, as mentioned above with reference to FIG. 1, tether 54 is first tether 54, and the length of first tether 54 is the first length, which may be between 30 and 80 mm, for example. Pulley system 44 further comprises second tether 56, which is connected (e.g., permanently fixed) to pulley 50 and atrial second tissue anchor 40, so as to fix pulley 50 to atrial second tissue anchor 40. For some applications, the second length of second tether 56, measured between the second atrial tissue anchor and the pulley, is at least 3 mm (e.g., between 5 and 8 mm), and/or at least 10% of the first length. For some applications, during implantation, venous first tissue anchor 30, atrial second tissue anchor 40, venous third tissue anchor 42, and pulley system 44 are positioned such that two longitudinal portions of first tether 54 adjacent to and on opposite sides of pulley 50 define an angle therebetween of (a) between 5 and 115 degrees, such as between 10 and 110 degrees, such as in the configuration shown in FIG. 3L, or (b) between 30 and 150 degrees, such as between 45 and 135 degrees, such as in the configuration shown in FIG. 3M.

For others of these applications, such as shown in FIGS. 3P and 3Q, venous third tissue anchor 42 is implanted at second implantation site 90 (which is coronary sinus 115), and atrial second tissue anchor 40 is implanted at third implantation site 92. Pulley 50 is connected to venous third tissue anchor 42. First tether 54 (i) is connected to venous first tissue anchor 30 and atrial second tissue anchor 40, (ii) is moveable through pulley 50, and (iii) typically has a first length, measured between venous first tissue anchor 30 and atrial second tissue anchor 40, of at least 15 mm, such as at least 30 mm. For some applications, as mentioned above with reference to FIG. 1, tether 54 is first tether 54, and the length of first tether 54 is the first length, which may be between 30 and 80 mm, for example. Pulley system 44 further comprises second tether 56, which is connected (e.g., permanently fixed) to pulley 50 and venous third tissue anchor 42, so as to fix pulley 50 to venous third tissue anchor 42. For some applications, the second length of second tether 56, measured between the venous third tissue anchor and the pulley, is at least 3 mm (e.g., between 3 and 8 mm), and/or at least 10% of the first length. For some applications, during implantation, venous first tissue anchor 30, atrial second tissue anchor 40, venous third tissue anchor 42, and pulley system 44 are positioned such that two longitudinal portions of first tether 54 adjacent to and on opposite sides of pulley 50 define an angle therebetween of (a) between 5 and 100 degrees, such as between 15 and 90 degrees, such as in the configuration shown in FIG. 3P, or (b) between 30 and 150 degrees, such as between 45 and 135 degrees, such as in the configuration shown in FIG. 3Q.

Figure 4:
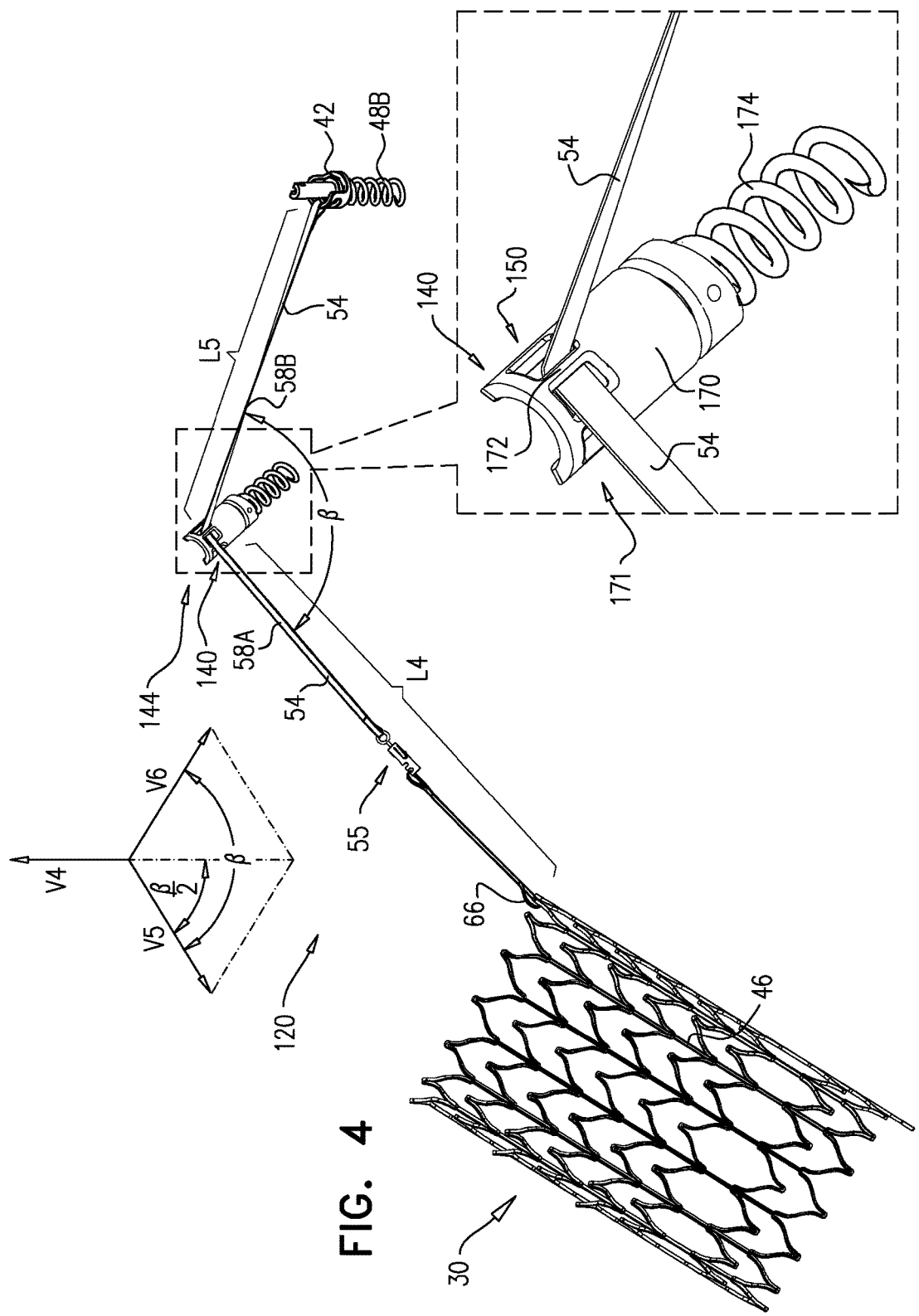
FIG. 4 is a schematic illustration of another valve-tensioning implant, in accordance with an application of the present invention.

Reference is now made to FIG. 4, which is a schematic illustration of a valve-tensioning implant system 120, in accordance with an application of the present invention. Other than as described hereinbelow, valve-tensioning implant system 120 is similar to, and may implement any of the features of, valve-tensioning implant system 20, described hereinabove with reference to FIGS. 1-3O. Valve-tensioning implant system 120 is configured to repair an atrioventricular valve of a subject (e.g., a tricuspid valve), using tension applied between multiple anchors of the implant. Typically, repair of the atrioventricular valve facilitates a reduction in atrioventricular valve regurgitation by altering the geometry of the atrioventricular valve and/or by altering the geometry of the wall of the right or left atrium of a heart of the subject.

For some applications, valve-tensioning implant system 120 comprises first venous tissue anchor 30, which is configured to be implanted in a vein selected from the group of veins consisting of: superior vena cava 110, inferior vena cava 80, and coronary sinus 115, such as described hereinbelow with reference to FIGS. 6A-I. First venous tissue anchor 30 may have any of the features described hereinabove with reference to FIG. 1.

Valve-tensioning implant system 120 further comprises a second atrial tissue anchor 140 and third atrial tissue anchor 42. For some applications, valve-tensioning implant system 120 comprises exactly two atrial tissue anchors, which consist of second and third atrial tissue anchors 140 and 42. Second atrial tissue anchor 140 comprises a head 170 and a tissue-coupling element 174. For some applications, head 170 is rotatable with respect to tissue-coupling element 174. Second and third atrial tissue anchors 140 and 42 may have any of the features of second and third atrial tissue anchors 40 and 42, described hereinabove with reference to FIG. 1.

Valve-tensioning implant system 120 further comprises a pulley system 144, which comprises (a) a pulley 150, which is connected (e.g., permanently fixed) to second atrial tissue anchor 140, and (b) tether 54 (described hereinabove with reference to FIG. 1), which is connected (e.g., permanently fixed) to first venous tissue anchor 30 and third atrial tissue anchor 42, and is moveable through pulley 150. Head 170 comprises pulley 150. For some applications, head 170 comprises a tether interface 171, which comprises pulley 150. For some applications, tether interface 171 and/or pulley 150 are rotatable with respect to tissue-coupling element 174. Such rotation may help reduce the torque applied to the atrial tissue by second atrial tissue anchor 140. Furthermore, the rotation allows a biased friction, i.e., more friction towards the anchor point than towards the stent point, thus reducing the forces acting on the stent which is anchored in place using friction only, as compared to the helical tissue anchors, which use mechanical purchase.

In the configuration described with reference to FIGS. 4-6I, tether 54 typically has a length, measured between first venous tissue anchor 30 and third atrial tissue anchor 42, of at least 20 mm, no more than 200 mm, and/or between 20 and 200 mm, such at least 30 mm, no more than 120 mm, and/or between 30 and 120 mm. The length equals the sum of (a) a first sub-length L4 of a first portion of the tether between first venous tissue anchor 30 and pulley 150 and (b) a second sub-length L5 of a second portion of the tether between pulley 150 and third atrial tissue anchor 42. (First and second sub-lengths L4 and L5 are not fixed, because tether 54 is both moveable through pulley 50 as well as rotatable around the pivot point; however, the sum of the two sub-lengths is fixed.) Because tether 54 typically has a high tensile strength, the length thereof does not vary based on the particular disposition of the tether at any given point in time. In other words, the length of the tether does not depend on the amount of force applied to it. For some applications, as described hereinabove with reference to FIG. 1, tether 54 is configured so as to define anchor-fixing loop 66, which passes through a corresponding interface (e.g., defined by struts of a stent) on first venous tissue anchor 30, so as to connect (e.g., permanently fix) the tether to the first venous tissue anchor.

For some applications, as shown in FIG. 4, pulley 150 comprises an eyelet 172, through which tether 54 is slidably moveable. Typically, a coefficient of kinetic friction between the tether and the eyelet is less than 0.5, such as less than 0.2, e.g., less than 0.1.

Figure 5A:
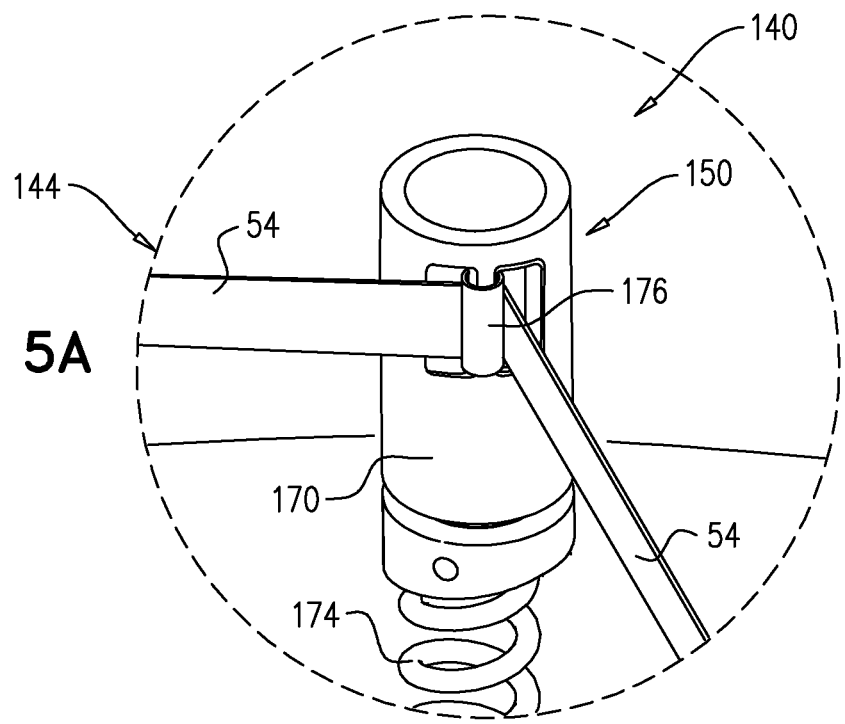
FIGS. 5A-B are schematic illustrations of two configurations of a pulley of the valve-tensioning implant of FIG. 4, in accordance with respective applications of the present invention.
Figure 5B:
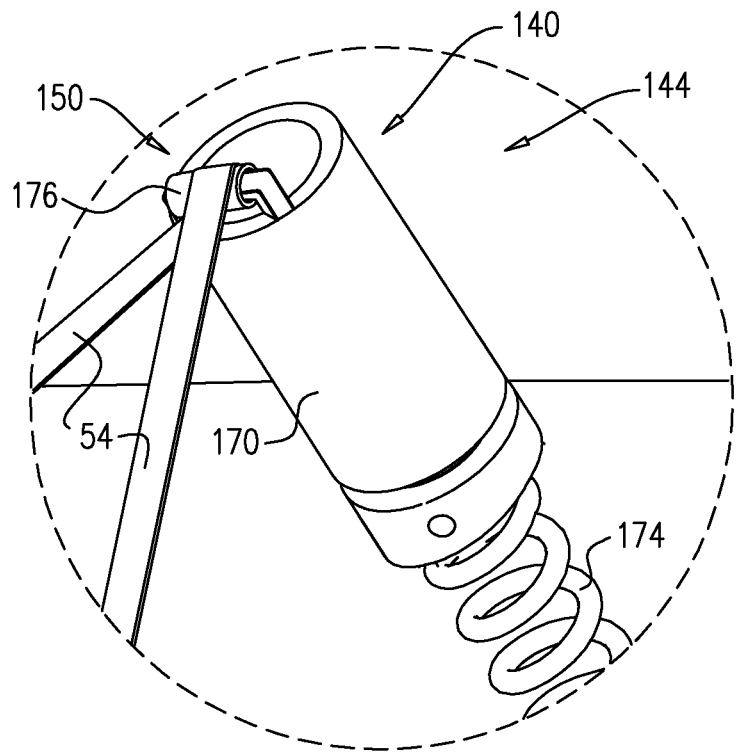

Reference is made to FIGS. 5A-B, which are schematic illustrations of two configurations of pulley 150, in accordance with respective applications of the present invention. In these configurations, pulley 150 comprises a roller 176, which is rotatable with respect to head 170, and around which tether 54 passes. For some applications, such as shown in FIG. 5A, the roller axis is oriented parallel with a longitudinal axis of head 170, while for other applications, such as shown in FIG. 5B, the roller axis is oriented perpendicular to the longitudinal axis of head 170.

Reference is now made to FIGS. 6A-I, which are schematic illustrations of implantations of valve-tensioning implant system 120, in accordance with respective applications of the present invention. The implantations are typically performed transvascularly, such as described hereinabove with reference to FIGS. 3A-Q. First venous tissue anchor 30 is implanted at first site 89 in a vein selected from the group of veins consisting of: inferior vena cava 80 (as shown, for example, in FIGS. 6A-D), superior vena cava 110 (as shown, for example, in FIGS. 6E-G), and coronary sinus 115 (as shown, for example, in FIGS. 6H-I). For applications in which first venous tissue anchor 30 comprises intraluminal stent 46, the stent is expanded in the selected vein in order to anchor the stent to the wall of the vein by the outward radial force applied by the stent.

Second and third atrial tissue anchors 140 and 42, e.g., exactly second and third atrial tissue anchors 140 and 42, are implanted at respective different second atrial sites 190 and 192, each of which sites is selected from the group of sites consisting of: annulus 83 of tricuspid valve 78, and a wall of right atrium 81 above annulus 83. For applications in which second and third atrial tissue anchors 140 and 42 comprise respective helical tissue-coupling elements 174 and 48B, the helical tissue-coupling elements are rotated into tissue at the sites, respectively.

Pulley system 144 is implanted (including by implanting second atrial tissue anchor 140). For applications in which intraluminal locking mechanism 55 is used, the male and female coupling elements thereof are locked together. A size of a tricuspid orifice is reduced by tensioning tether 54, so as to reduce regurgitation.

(As used herein, including in the claims, the labels "first," "second," and "third" of first, second, and third sites 89, 190, and 192, and of first, second, and third tissue anchors 30, 40, and 42, are to be understood only as convenient references to distinguish the sites and anchors from one another, and are not to be understood as implying or requiring any order of implantation or of other properties of the sites or anchors.)

Pulley system 144 enables the controlled, uneven distribution of forces on tissue at first, second, and third implantation sites 89, 190, and 192. As labeled in FIG. 4, a force vector V4 on the tissue at second implantation site 190, which is connected (e.g., permanently fixed) to pulley 150 by second tissue anchor 140, equals the vector sum of force vectors V5 and V6 acting on tissue at first and third implantation sites 189 and 192, respectively, which are connected (e.g., permanently fixed) to tether 54 by first venous tissue anchor 30 and third atrial tissue anchor 42, respectively. (Force vectors V4, V5, and V6 are not drawn to scale in FIG. 4.) As a result, the forces acting on first and third implantation sites 89 and 192 are less than the force acting on second implantation site 190 (to which the pulley is fixed).

This controlled distribution of forces may be particularly beneficial if, for example:
  second implantation site 190 (to which the pulley is fixed) is located in a region of tissue which is thicker or stronger than first and/or third implantation sites 89 and 192. For example, tissue of the septum between the ventricles is thicker and stronger than the atrium wall and the vena cava wall;
  the anchoring mechanism of the anchor to which the pulley is not fixed performs anchoring using mechanical purchase, e.g., using a helical anchor, while the anchoring mechanism of another of the anchors the (e.g., at first implantation site 89) is friction based, e.g., using an intraluminal stent; and/or
  the force vectors acting on first implantation site 89 and second implantation site 190 (to which the pulley is fixed) are aligned along a preferable direction which causes constriction of the tricuspid valve in a more favorable manner than tensioning towards third implantation site 192 alone. For example, the sites may be selected apply the maximum force on the implantation site that is desired to be moved.

The tissue anchors and pulley system 144 are arranged such that the vector sum of the forces on all of the implantation sites is zero, and the force vector on second implantation site 190 (to which the pulley is fixed) is the vector sum of the forces acting on first and third implantation sites 89 and 192. The scalar force acting on first and third implantation sites 89 and 192 depends on an angle β (beta) (labeled in FIG. 4) formed by tether 54 at pulley 150, and may be expressed by Equation 1, described above with reference to FIG. 1, mutatis mutandis.

In accordance with this equation, the force acting on each of first and third implantation sites 89 and 192 is equal to the force acting on second implantation site 190 when the angle is 120 degrees, and increases as the angle increases, to approximately 46% greater than the force acting on second implantation site 190 when the angle is 140 degrees. (Angle β (beta) is defined by two longitudinal portions 58A and 58B (labeled in FIG. 4) of tether 54 adjacent to and on opposite sides of pulley 150.) For some applications, in order to achieve the desired force distribution among the implantation sites, when implanting the tissue anchors, the surgeon positions the tissue anchors and pulley system 144 such that angle β (beta) is between 120 and 180 degrees, such as between 135 and 175 degrees, typically as close as possible to 180 degrees, which will result in zero force on the pulley point (although achieving 180 degrees is difficult, if not impossible, in practice).

The following table sets forth exemplary combinations of first implantation site 89 and anatomical markers for second and third implantation sites 190 and 192, and figures that show exemplary deployments at these sites. These sites are listed by way of example and not limitation; the surgeon typically selects the exact sites based on the subject's individual needs and anatomy. Each of second and third implantation sites 190 and 192 is located within 1 cm of the site on the annulus that circumferentially corresponds to the respective anatomical marker. The direction of the 1 cm from the site may be either circumferentially around the annulus, up the wall of right atrium 81 above annulus 83, or a combination of circumferentially around the annulus and up the wall of the atrium.

Figure 7:
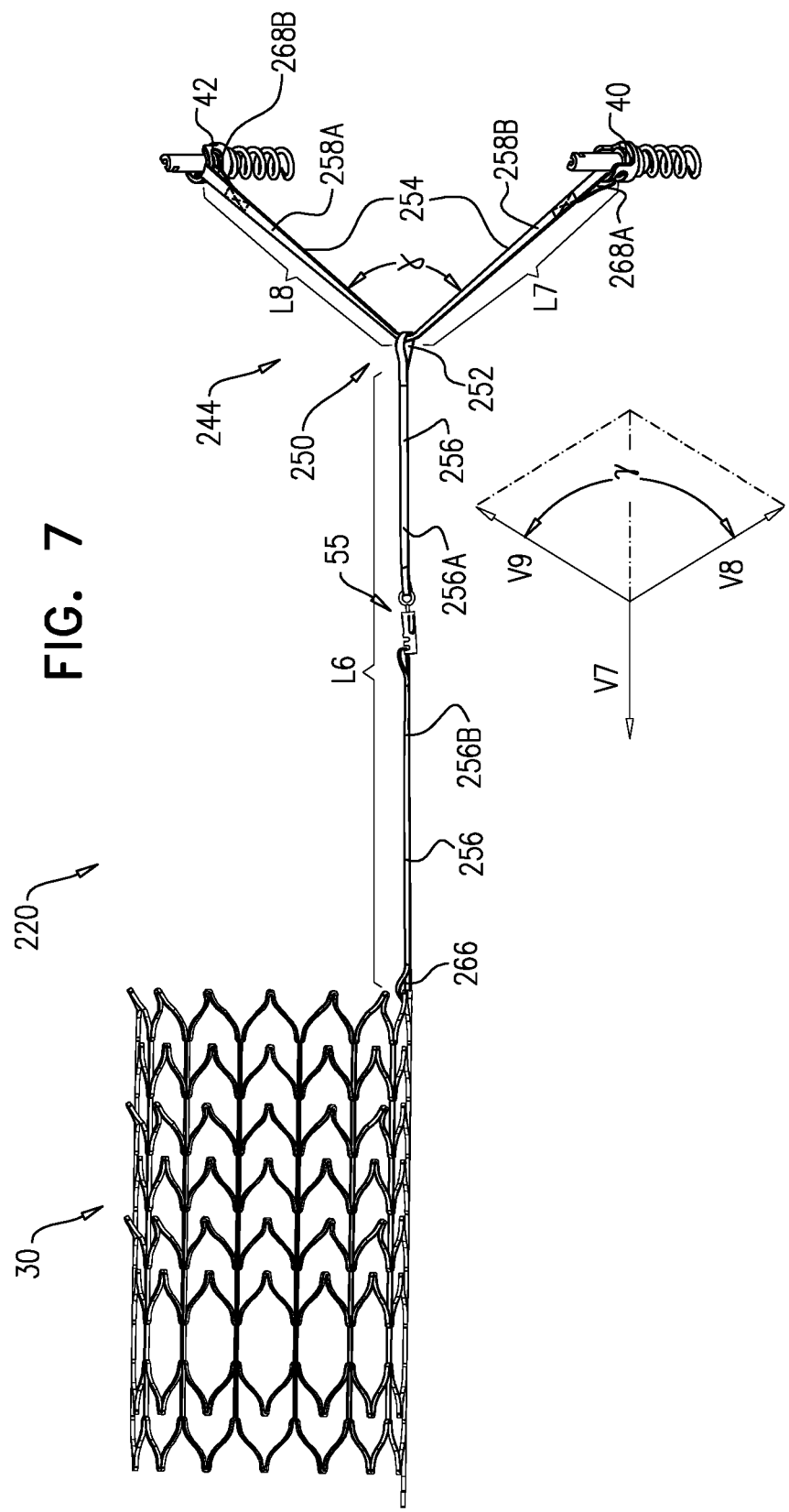
FIG. 7 is a schematic illustration of yet another valve-tensioning implant, in accordance with an application of the present invention.

Reference is now made to FIG. 7, which is a schematic illustration of a valve-tensioning implant system 220, in accordance with an application of the present invention. Other than as described hereinbelow, valve-tensioning implant system 220 is similar to, and may implement any of the features of, valve-tensioning implant system 20, described hereinabove with reference to FIGS. 1-3O. Valve-tensioning implant system 220 is configured to repair an atrioventricular valve of a subject (e.g., a tricuspid valve), using tension applied between multiple anchors of the implant. Typically, repair of the atrioventricular valve facilitates a reduction in atrioventricular valve regurgitation by altering the geometry of the atrioventricular valve and/or by altering the geometry of the wall of the right or left atrium of a heart of the subject.

For some applications, valve-tensioning implant system 220 comprises first venous tissue anchor 30, which is configured to be implanted in a vein selected from the group of veins consisting of: superior vena cava 110, inferior vena cava 80, and coronary sinus 115. First venous tissue anchor 30 may have any of the features described hereinabove with reference to FIG. 1.

Valve-tensioning implant system 220 further comprises second and third atrial tissue anchors 40 and 42. For some applications, valve-tensioning implant system 220 comprises exactly two atrial tissue anchors, which consist of second and third atrial tissue anchors 40 and 42. Second and third atrial tissue anchors 40 and 42 may have any of the features of second and third atrial tissue anchors 40 and 42, described hereinabove with reference to FIG. 1.

Valve-tensioning implant system 220 further comprises a pulley system 244, which comprises:

a pulley 250, which is connected (e.g., permanently fixed) to first venous tissue anchor 30;

TABLE 2

Figure 6A:
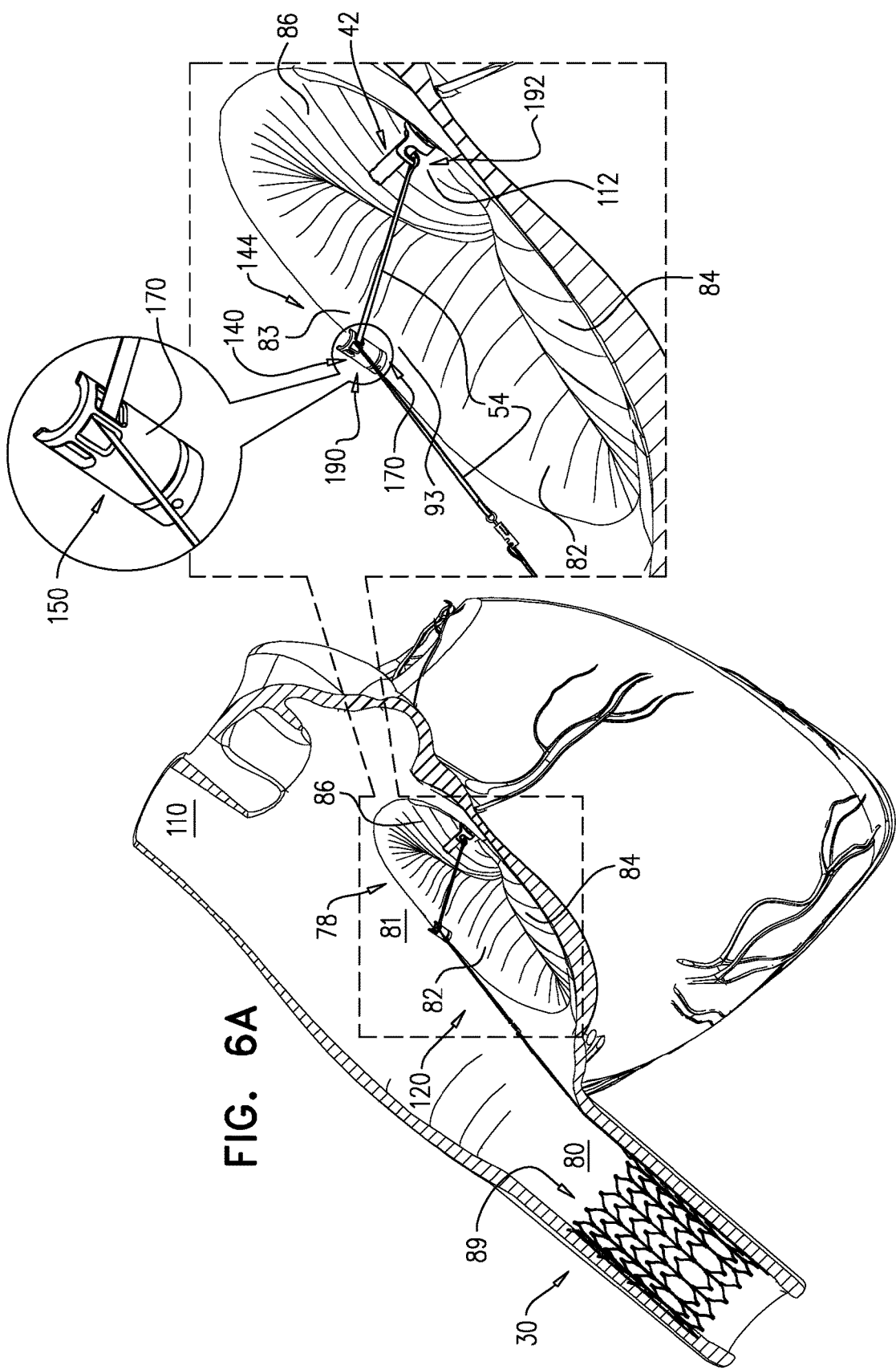
Figure 6B:
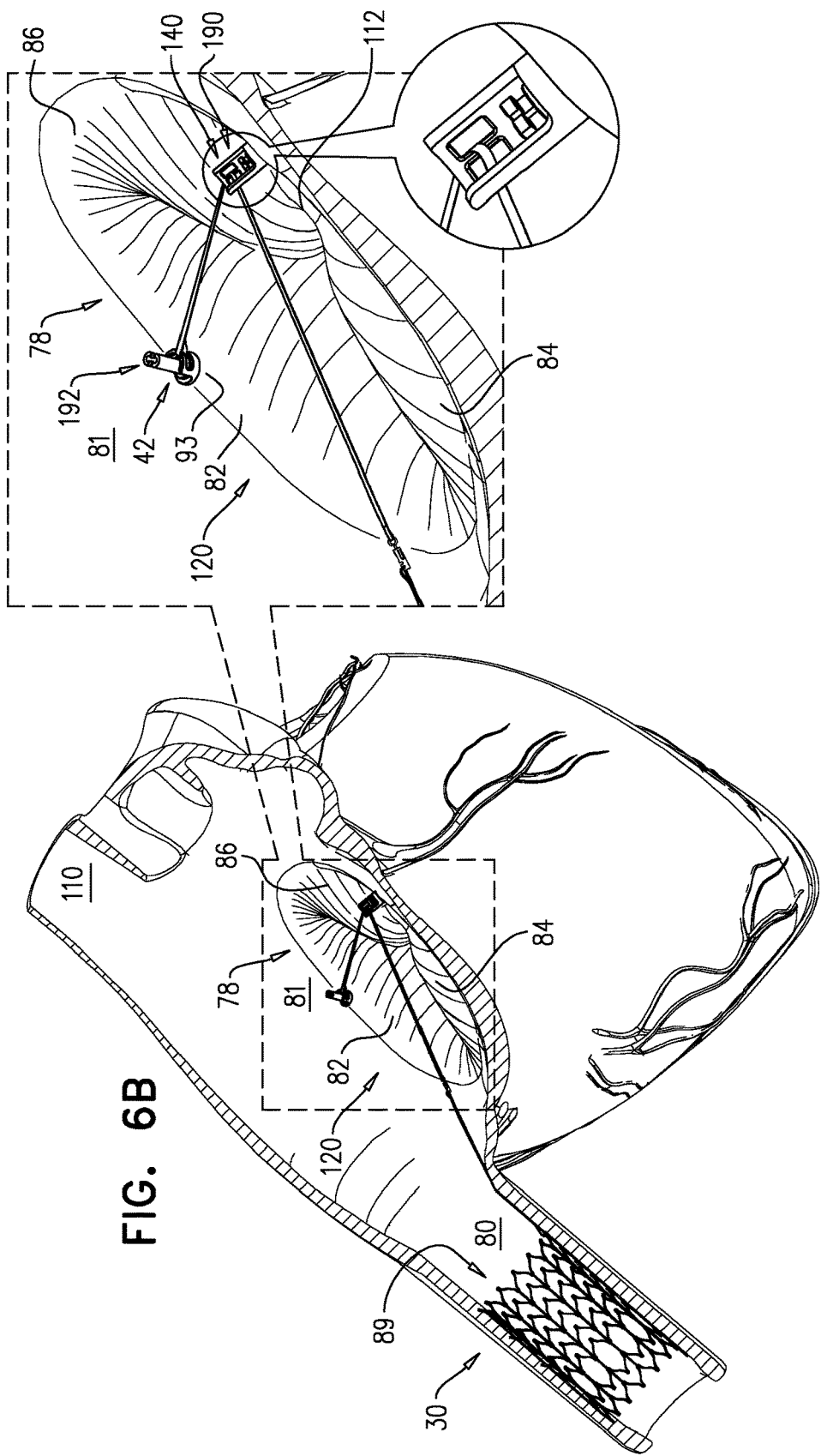
Figure 6C:
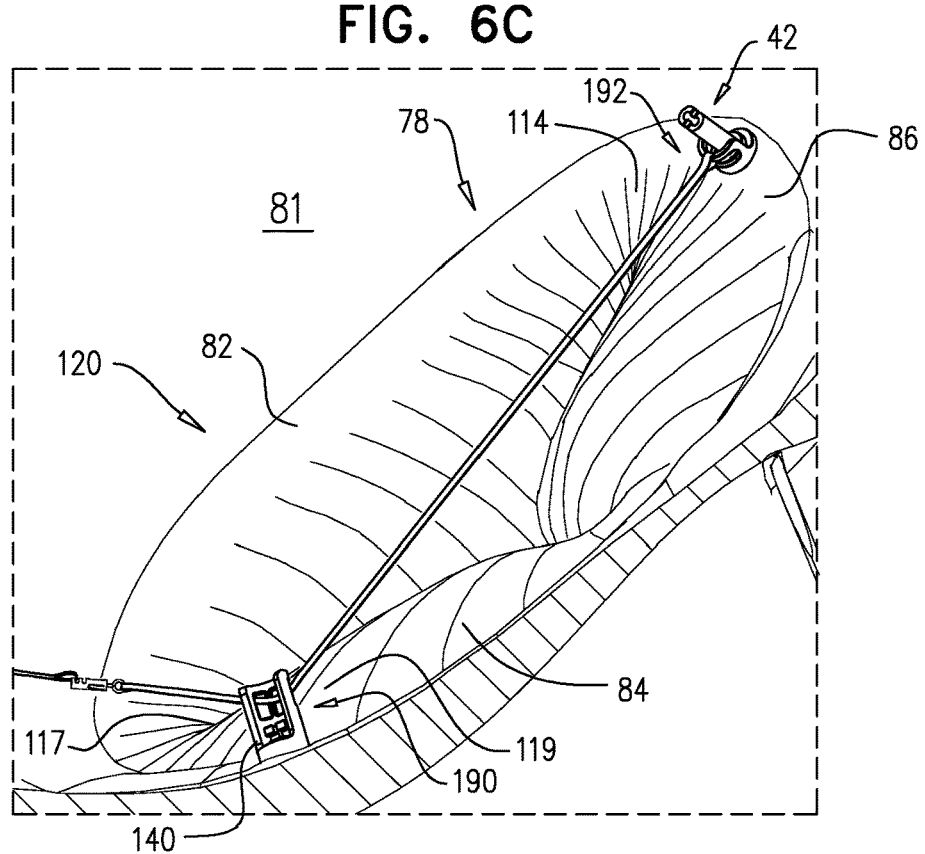
Figure 6D:
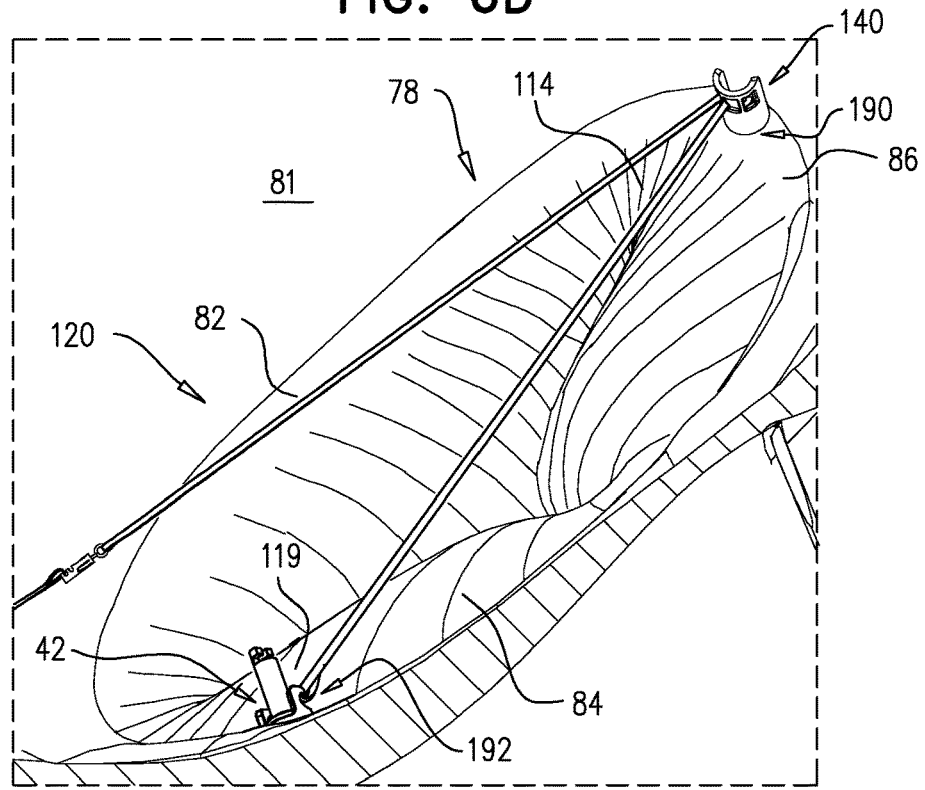
Figure 6E:
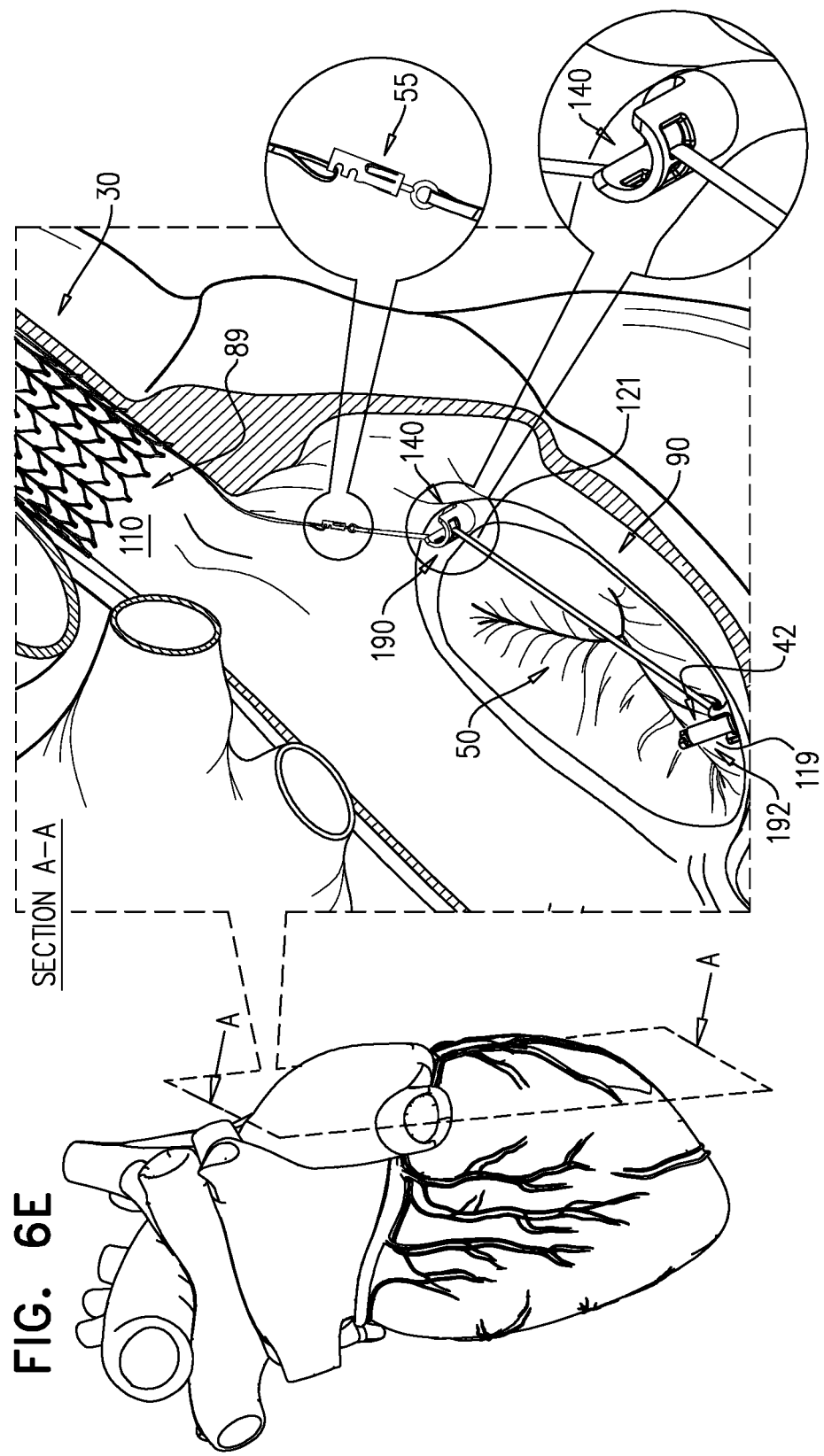
Figure 6F:
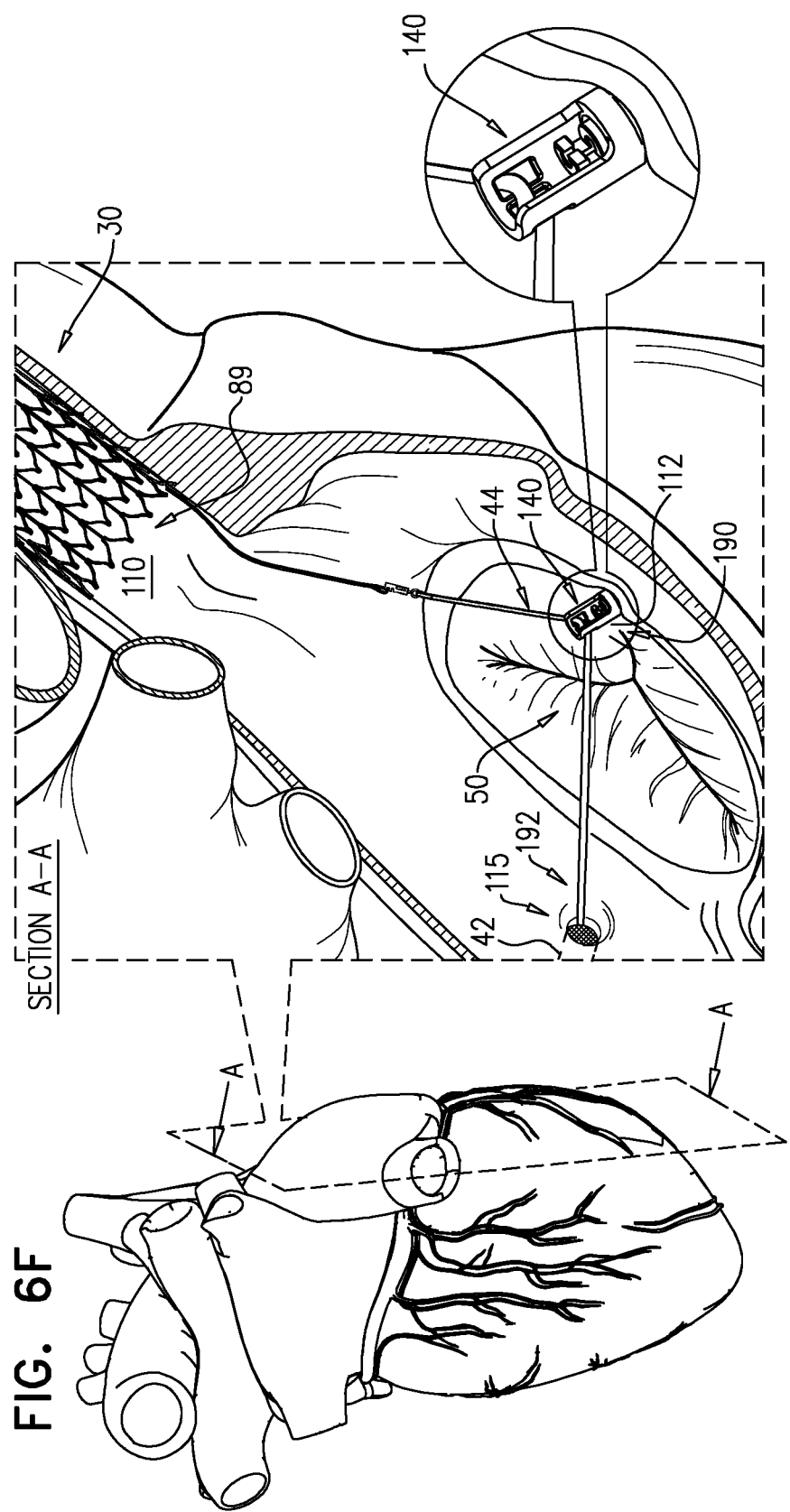
Figure 61:
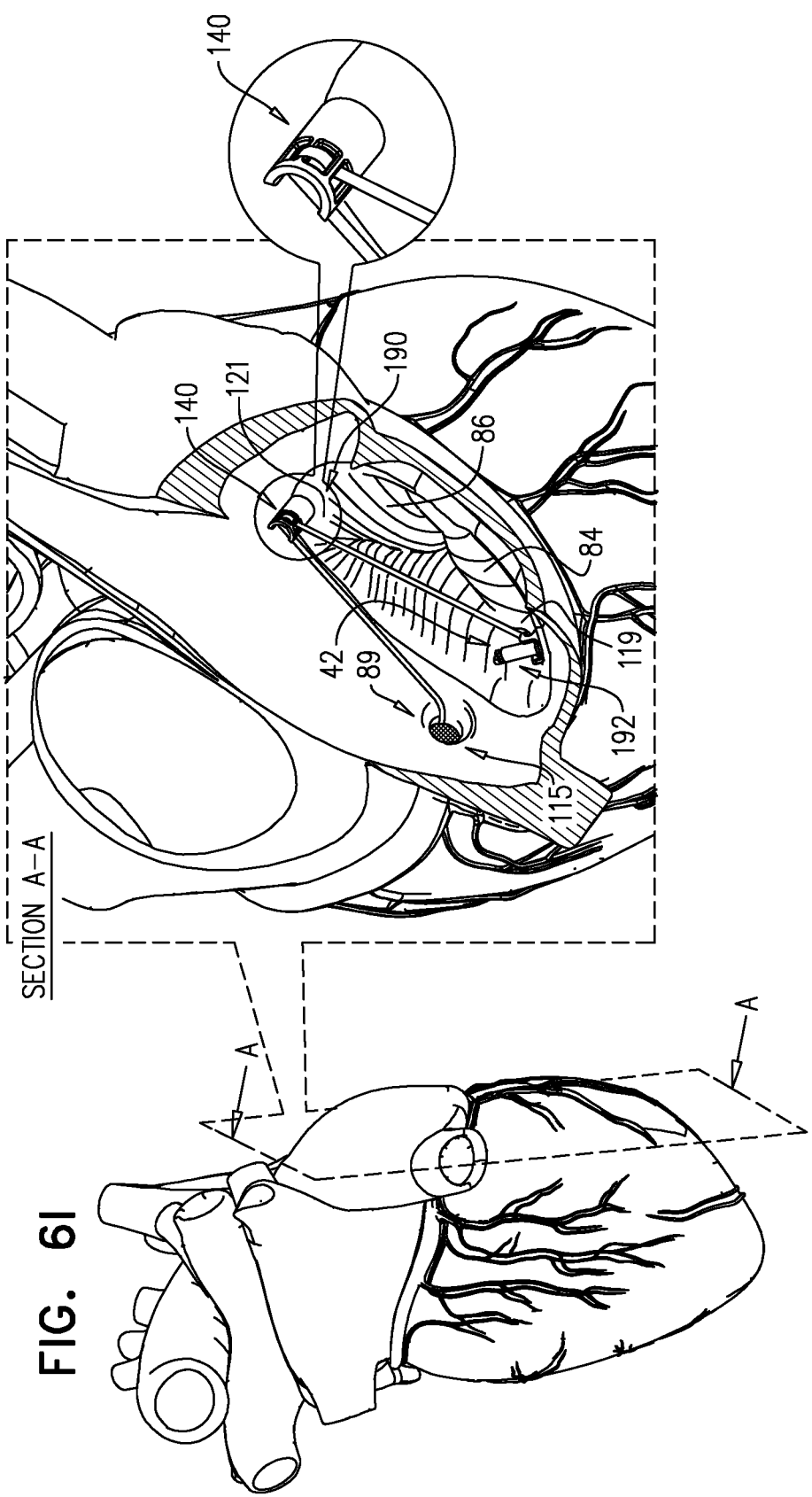

| First implantation site 89 | Second implantation site 190 (pulley) anatomical marker | Third implantation site 192 anatomical marker | FIG. |
| --- | --- | --- | --- |
| Inferior vena cava 80 | Circumferential middle 93 of septal leaflet 82 | Anteroposterior commissure 112 | FIG. 6A |
| Inferior vena cava 80 | Anteroposterior commissure 112 | Circumferential middle 93 of septal leaflet 82 | FIG. 6B |
| Inferior vena cava 80 | Circumferential middle 119 of posterior leaflet 84 | Septoanterior commissure 114 | FIG. 6C |
| Inferior vena cava 80 | Septoanterior commissure 114 | Circumferential middle 119 of posterior leaflet 84 | FIG. 6D |
| Superior vena cava 110 | Circumferential middle 121 of anterior leaflet 86 | Circumferential middle 119 of posterior leaflet 84 | FIG. 6E |
| Superior vena cava 110 | Anteroposterior commissure 112 | Coronary Sinus 115 | FIG. 6F |
| Superior vena cava 110 | Circumferential middle 119 of posterior leaflet 84 | Circumferential middle 121 of anterior leaflet 86 | FIG. 6G |
| Coronary Sinus 115 | Anteroposterior commissure 112 | Septoanterior commissure 114 | FIG. 6H |
| Coronary Sinus 115 | Circumferential middle 121 of anterior leaflet 86 | Circumferential middle 119 of posterior leaflet 84 | FIG. 6I |

Thus, for some applications, an implantation method comprises implanting first venous tissue anchor 30 at first implantation site 89 in inferior vena cava 80. For some applications, second atrial tissue anchor 140 is implanted at second implantation site 190 which is located within 1 cm of a site on the annulus that circumferentially corresponds to circumferential middle 93 of septal leaflet 82 of tricuspid valve 78, and third atrial tissue anchor 42 is implanted at third implantation site 192 which is located within 1 cm of a site on the annulus that circumferentially corresponds to anteroposterior commissure 112 of tricuspid valve 78.

a first tether 254, which (a) is connected (e.g., permanently fixed) to second and third atrial tissue anchors 40 and 42, (b) is moveable through pulley 250, and/or the pulley is rotatable around a pivot point, and (c) has a first length, measured between the second and the third atrial tissue anchors, of at least 10 mm, e.g., at least 15 mm, such as at least 20 mm, no more than 50 mm, and/or between 20 and 50 mm, or between 15 and 30 mm; and a second tether 256, which (a) is connected (e.g., permanently fixed) to first venous tissue anchor 30 and to pulley 250, and (b) has a second length L6, measured between first venous tissue anchor 30 and pulley 250, equal to at least 80% (e.g., at least 100%) of the first length, of at least 25 mm (e.g., at least 30 mm), no more than 180 mm, and/or between 25 mm (e.g., 30 mm) and 180 mm, e.g., no more than 120 mm and/or between 30 and 120 mm.

First and second tethers 254 and 256 comprise respective elongate flexible elements, such as cords, sutures, or bands. The tethers are typically sufficiently flexible for twisting or bending but are inelastic against tension. Typically, first and second tethers 254 and 256 have a high tensile strength, in order to enable the tethers to apply tension, as described hereinbelow.

The first length equals the sum of (a) a first sub-length L7 of a first portion of first tether 254 between second atrial tissue anchor 40 and pulley 250 and (b) a second sub-length L8 of a second portion of first tether 254 between pulley 250 and third atrial tissue anchor 42. (First and second sub-lengths L7 and L8 are not fixed, because tether 54 is both moveable through pulley 50 as well as rotatable around the pivot point; however, the sum of the two sub-lengths is fixed.) Because the first and the second tethers typically have a high tensile strength, the lengths thereof do not vary based on the particular disposition of the first and the second tethers at any given point in time. In other words, the lengths of the tethers do not depend on the amount of force applied to them.

For some applications, the second length L6 equals at least 100% of the first length.

For some applications, second tether 256 is configured so as to define an anchor-fixing loop 266, which passes through a corresponding interface (e.g., defined by struts of the stent) on first venous tissue anchor 30, so as to connect (e.g., permanently fix) the second tether to the first venous tissue anchor. For some applications, first tether 254 is configured so as to define one or both of anchor-fixing loops 268A and 268B, which pass through corresponding interfaces on second and third atrial tissue anchors 40 and 42, respectively, so as to connect (e.g., permanently fix) the first tether to the second and third atrial tissue anchors, respectively.

For some applications, tether 256 comprises two separate sections 256A and 256B, which may be connected by intraluminal locking mechanism 55, described hereinabove with reference to FIG. 1.

For some applications, as shown in FIG. 7, pulley 250 comprises a loop 252, through which first tether 254 is slidably moveable. Typically, a coefficient of kinetic friction between the first tether and the loop is less than 0.5, such as less than 0.2, e.g., less than 0.1. For some applications, as shown in FIG. 7, loop 252 comprises a closed loop; in other words, the ends of the loop are joined together. For other applications (not shown), loop 252 comprises an open loop; both ends of the cord that defines the loop are connected (e.g., permanently fixed) to first venous tissue anchor 30, but not to one another. In other words, pulley 250 comprises a flexible longitudinal member that is connected (e.g., permanently fixed) to the first venous tissue anchor 30 at two points along the flexible longitudinal member, so as to define loop 252 longitudinally between the two points.

For some applications, such as shown in FIG. 2C, described hereinabove, pulley 250 comprises ring 60, through which first tether 254 is slidably moveable. Typically, a coefficient of kinetic friction between first tether 254 and ring 60 is less than 0.5, such as less than 0.2, e.g., less than 0.1. For other applications, such as shown in FIG. 2D, described hereinabove, pulley 250 comprises wheel 62 on an axle that supports movement of first tether 254 along the wheel's circumference. Wheel 62 typically is shaped so as to define a groove between two flanges around its circumference, as is well-known in the pulley art. Pulley 250 may alternatively comprise an eyelet or a roller, such as described hereinabove with reference to FIGS. 4 and 5A-B.

Reference is now made to FIGS. 8A-H, which are schematic illustrations of implantations of valve-tensioning implant system 220, in accordance with respective applications of the present invention. The implantations are typically performed transvascularly, such as described hereinabove with reference to FIGS. 3A-Q. First venous tissue anchor 30 is implanted at first site 89 in a vein selected from the group of veins consisting of: superior vena cava 110 (as shown, for example, in FIGS. 8C-D), inferior vena cava 80 (as shown, for example, in FIGS. 8A-B and 8H), and coronary sinus 115, as shown, for example, in FIGS. 8E-G). For applications in which first venous tissue anchor 30 comprises intraluminal stent 46, the stent is expanded in the selected vein in order to anchor the stent to the wall of the vein by the outward radial force applied by the stent.

Second and third atrial tissue anchors 40 and 42, e.g., exactly second and third atrial tissue anchors 40 and 42, are implanted at respective different second atrial sites 290 and 292, each of which sites is selected from the group of sites consisting of: annulus 83 of tricuspid valve 78, and a wall of right atrium 81 above annulus 83. For applications in which second and third atrial tissue anchors 40 and 42 comprise respective helical tissue-coupling elements 48A and 48B, the helical tissue-coupling elements are rotated into tissue at the sites, respectively.

Figure 8A:
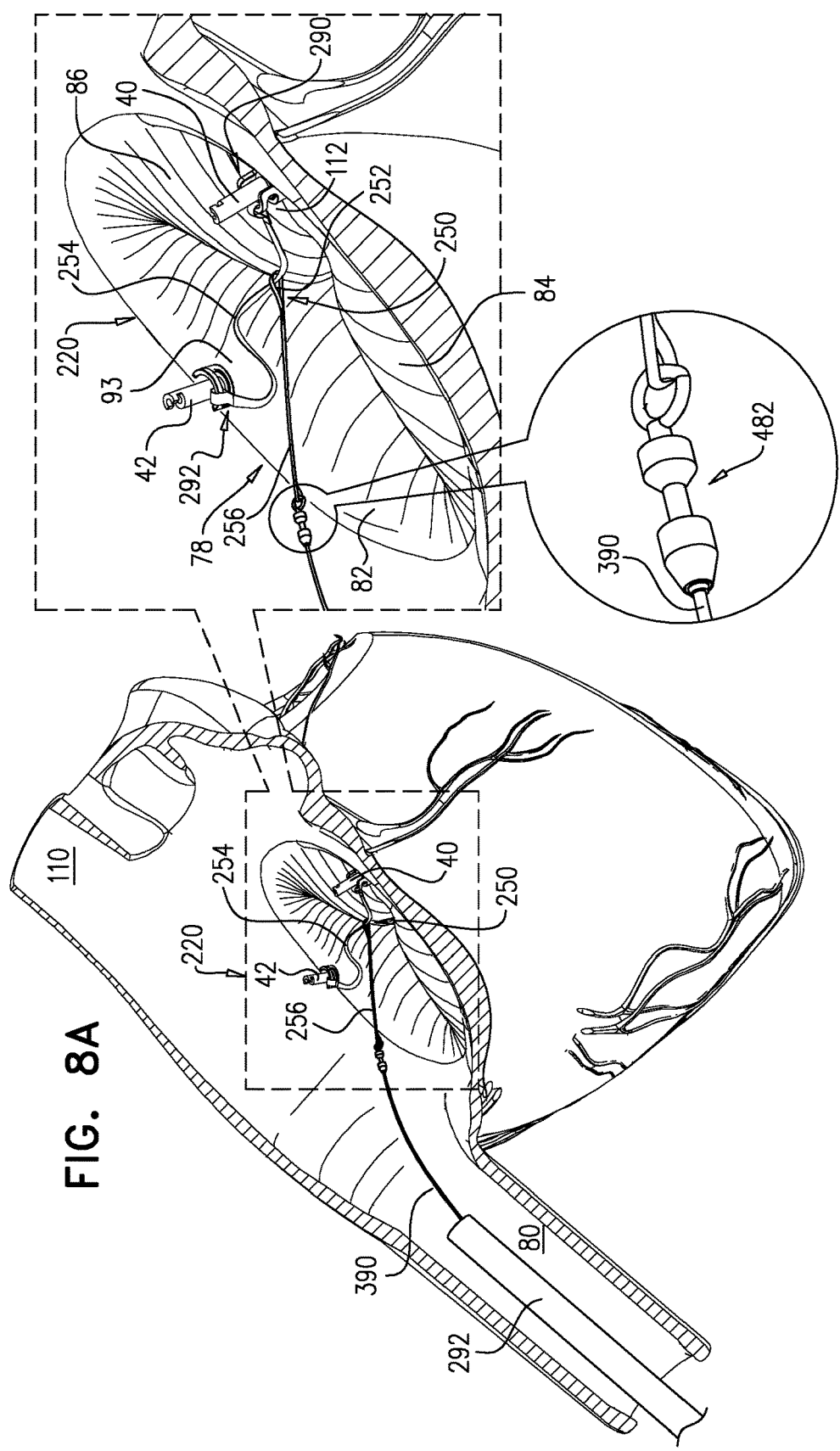
Figure 8B:
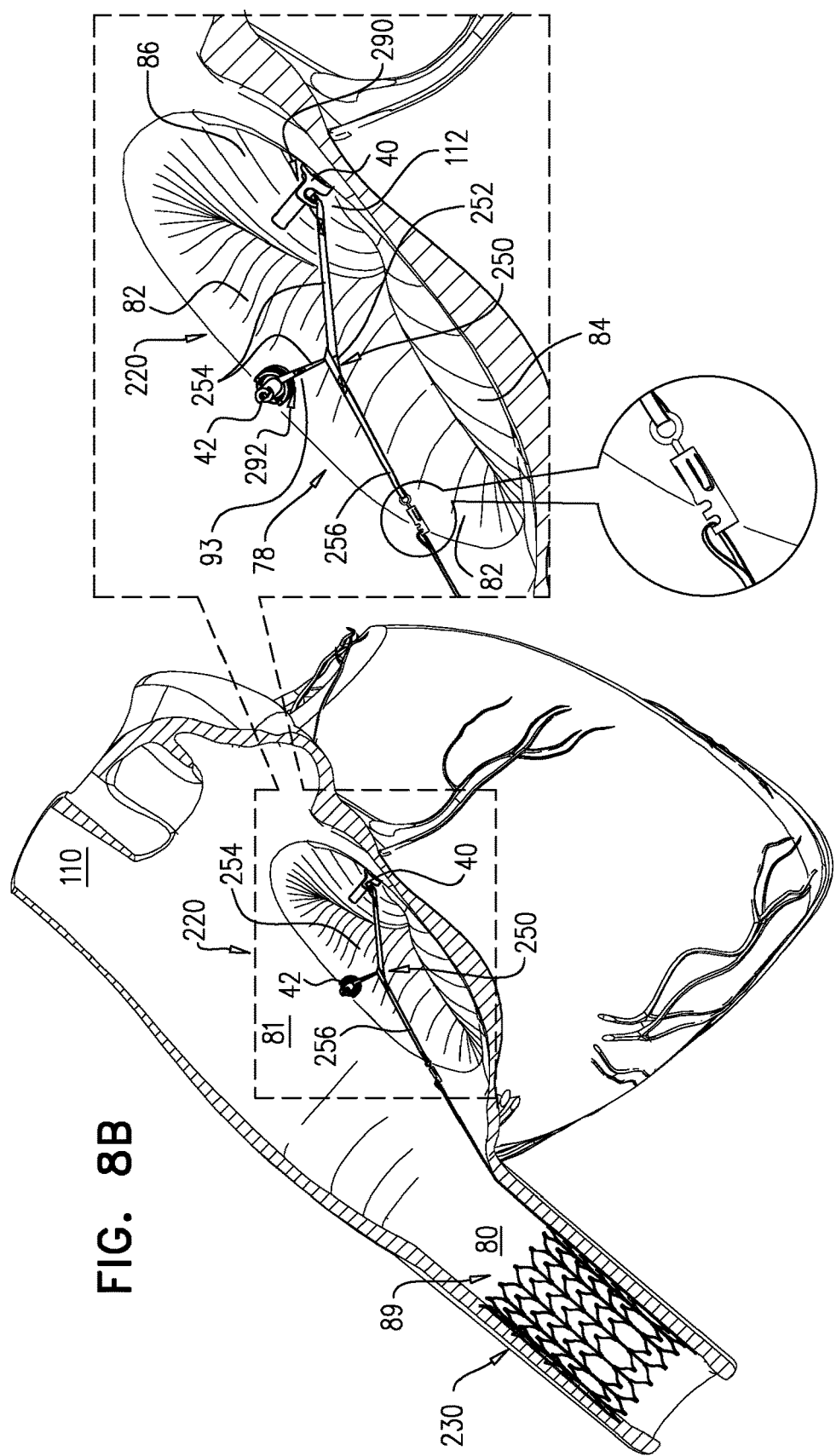

Pulley system 244 is implanted, locking mechanism 55, if provided, is attached, and a size of a tricuspid orifice is reduced by tensioning second tether 256, which also tensions first tether 254, so as to reduce regurgitation. FIG. 8A shows the pulley system before the locking mechanism has been attached and the tethers have been tensioned, and FIG. 8B shows the pulley system after the locking mechanism is attached and the tethers have been tensioned.

(As used herein, including in the claims, the labels "first," "second." and "third" of first, second, and third sites 89, 290, and 292, and of first, second, and third tissue anchors 30, 40, and 42, are to be understood only as convenient references to distinguish the sites and anchors from one another, and are not to be understood as implying or requiring any order of implantation or of other properties of the sites or anchors.)

Pulley system 244 enables the controlled, uneven distribution of forces on tissue at first, second, and third implantation sites 89, 290, and 292. As labeled in FIG. 7, a force vector V7 on the tissue at first implantation site 89, which is connected (e.g., permanently fixed) to pulley 250 by first venous tissue anchor 30, equals the vector sum of force vectors V8 and V9 acting on tissue at second and third implantation sites 290 and 292, respectively, which are connected (e.g., permanently fixed) to first tether 254 by second and third atrial tissue anchors 40 and 42, respectively. As a result, the forces acting on first implantation site 89 (to which the pulley is fixed) is less than the forces acting on second and third implantation site 290 and 292.

This controlled distribution of forces may be particularly beneficial if, for example:
  second implantation site 290 or third implantation site 292 is located in a region of tissue which is thicker or stronger than first implantation site 89. For example, tissue of the septum between the ventricles is thicker and stronger than the vena cava wall;

the anchoring mechanism of second and third atrial tissue anchors 40 and 42 anchors using mechanical purchase, e.g., using a helical anchor, while the anchoring mechanism of first venous tissue anchor 30 at first implantation site 89 is friction based, e.g., using an intraluminal stent; and/or the force vectors acting on second and third implantation sites 290 and 292 are aligned along a preferable direction which causes constriction of the tricuspid valve in a more favorable manner than tensioning towards first implantation site 89. For example, the sites may be selected apply the maximum force on the implantation site that is desired to be moved.

The tissue anchors and pulley system 244 are arranged such that the vector sum of the forces on all of the implantation sites is zero, and the force vector on first implantation site 89 (to which the pulley is fixed) is the vector sum of the forces acting on second and third implantation sites 190 and 192. The scalar force acting on second and third implantation sites 190 and 192 depends on an angle γ (gamma) (labeled in FIG. 7) formed by first tether 254 at pulley 250, and may be expressed by Equation 1, described above with reference to FIG. 1, mutatis mutandis.

In accordance with this equation, the force acting on first implantation site 89 (to which the pulley is fixed) is less than each of the forces acting on second and third implantation sites 290 and 292; at an angle γ (gamma) of 120 degrees, all forces are approximately equal. As the angle increases and approximates 180 degrees, the force on first implantation site 89 is reduced to almost zero, although such an angle is not achievable in practice. For example, when angle γ (gamma) is 140 degrees, the force at first implantation site 89 is only approximately 68% of the force acting on each of second and third implantation sites 190 and 192. When the angle is 160 degrees, the force at first implantation site 89 is further reduced to approximately 35% of the force acting on each of second and third implantation sites 190 and 192.

For some applications, in order to achieve the desired force distribution among the implantation sites, when implanting the tissue anchors, the surgeon positions the tissue anchors and pulley system 144 such that two longitudinal portions 258A and 258B (labeled in FIG. 7) of first tether 254 adjacent to and on opposite sides of pulley 250 define an angle γ (gamma) therebetween, typically of between 120 and 180 degrees, such as between 135 and 175 degrees, typically as close as possible to 180 degrees.

The following table sets forth exemplary combinations of first implantation site 89 and anatomical markers for second and third implantation sites 290 and 292, and figures that show exemplary deployments at these sites. These sites are listed by way of example and not limitation; the surgeon typically selects the exact sites based on the subject's individual needs and anatomy. Each of second and third implantation sites 290 and 292 is located within 1 cm of the site on the annulus that circumferentially corresponds to the respective anatomical marker. The direction of the 1 cm from the site may be either circumferentially around the annulus, up the wall of right atrium 81 above annulus 83, or a combination of circumferentially around the annulus and up the wall of the atrium.

TABLE 3

| First implantation site 89 (pulley) | Second implantation site 290 anatomical marker | Third implantation site 292 anatomical marker | FIG.(s) |
|---|---|---|---|
| Inferior vena cava 80 | Anteroposterior commissure 112 | Circumferential middle 93 of septal leaflet 82 | FIGS. 8A and 8B |
| Superior vena cava 110 | Anteroposterior commissure 112 | Septoanterior commissure 114 | FIG. 8C |
| Inferior vena cava 80 | Circumferential middle 93 of septal leaflet | Septoanterior commissure 114 | FIG. 8H |
| Superior vena cava 110 | Circumferential middle 93 of septal leaflet 82 | Anteroposterior commissure 112 | FIG. 8D |
| Coronary sinus 115 | Anteroposterior commissure 112 | Septoposterior commissure 117 | FIG. 8E |
| Coronary sinus 115 | Circumferential middle 93 of septal leaflet 82 | Anteroposterior commissure 112 | FIG. 8F |
| Coronary sinus 115 | Circumferential middle 121 of anterior leaflet 86 | Circumferential middle 119 of posterior leaflet 84 | FIG. 8G |

Thus, for some applications, an implantation method comprises implanting first venous tissue anchor 30 at first implantation site 89 in inferior vena cava 80. For some applications, second atrial tissue anchor 40 is implanted at second implantation site 290 which is located within 1 cm of a site on the annulus that circumferentially corresponds to anteroposterior commissure 112. For some applications, third atrial tissue anchor 42 is implanted at third implantation site 292 which is located within 1 cm of a site on the annulus that circumferentially corresponds to septoanterior commissure 114. Alternatively, for some applications, third atrial tissue anchor is implanted at third implantation site 292 which is located within 1 cm of a site on the annulus that circumferentially corresponds to circumferential middle 93 of septal leaflet 82.

For other applications, the implantation method comprises implanting first venous tissue anchor 30 at first implantation site 89 in superior vena cava 110. For some applications, third atrial tissue anchor 42 is implanted at third implantation site 292 which is located within 1 cm of a site on the annulus that circumferentially corresponds to anteroposterior commissure 112. For some applications, second atrial tissue anchor 40 is implanted at second implantation site 290 which is located within 1 cm of a site on the annulus that circumferentially corresponds to septoanterior commissure 114. Alternatively, for some applications, second atrial tissue anchor 40 is implanted at second implantation site 290 which is located within 1 cm of a site on the annulus that circumferentially corresponds to circumferential middle 93 of septal leaflet 82.

For still other applications, the implantation method comprises implanting first venous tissue anchor 30 at first implantation site 89 in the coronary sinus. For some applications, third atrial tissue anchor 42 is implanted at third implantation site 292 which is located within 1 cm of a site on the annulus that circumferentially corresponds to anteroposterior commissure 112. For some applications, second atrial tissue anchor 40 is implanted at second implantation site 290 which is located within 1 cm of a site on the annulus that circumferentially corresponds to septoanterior commissure 114. Alternatively, for some applications, second atrial tissue anchor 40 is implanted at second implantation site 290 which is located within 1 cm of a site on the annulus that circumferentially corresponds to of circumferential middle 93 of septal leaflet 82.

Reference is again made to FIGS. 1-4H and 7-8H. For some applications, a valve-tensioning implant system 20, 220 is provided, which comprises first, second, and third tissue anchors 30, 40, and 42. For some applications, the valve-tensioning implant comprises exactly three tissue anchors, which consist of first, second, and third tissue anchors 30, 40, and 42. First tissue anchor 30 is not necessarily a venous tissue anchor.

Valve-tensioning implant system 20, 220 further comprises pulley system 44, 244, which comprises:
  pulley 50, 250;
  first tether 54, 254, which (a) is connected (e.g., permanently fixed) to second and third tissue anchors 40 and 42, (b) is moveable through pulley 50, 250, and (c) has a first length, measured between second and third tissue anchors 40 and 42, of at least 15 mm, and
  second tether 56, 256, which (a) is connected (e.g., permanently fixed) to first tissue anchor 30 and to pulley 50, 250, and (b) has a second length, measured between first tissue anchor 30 and pulley 50, 250, of at least 15 mm.

Figure 9A:
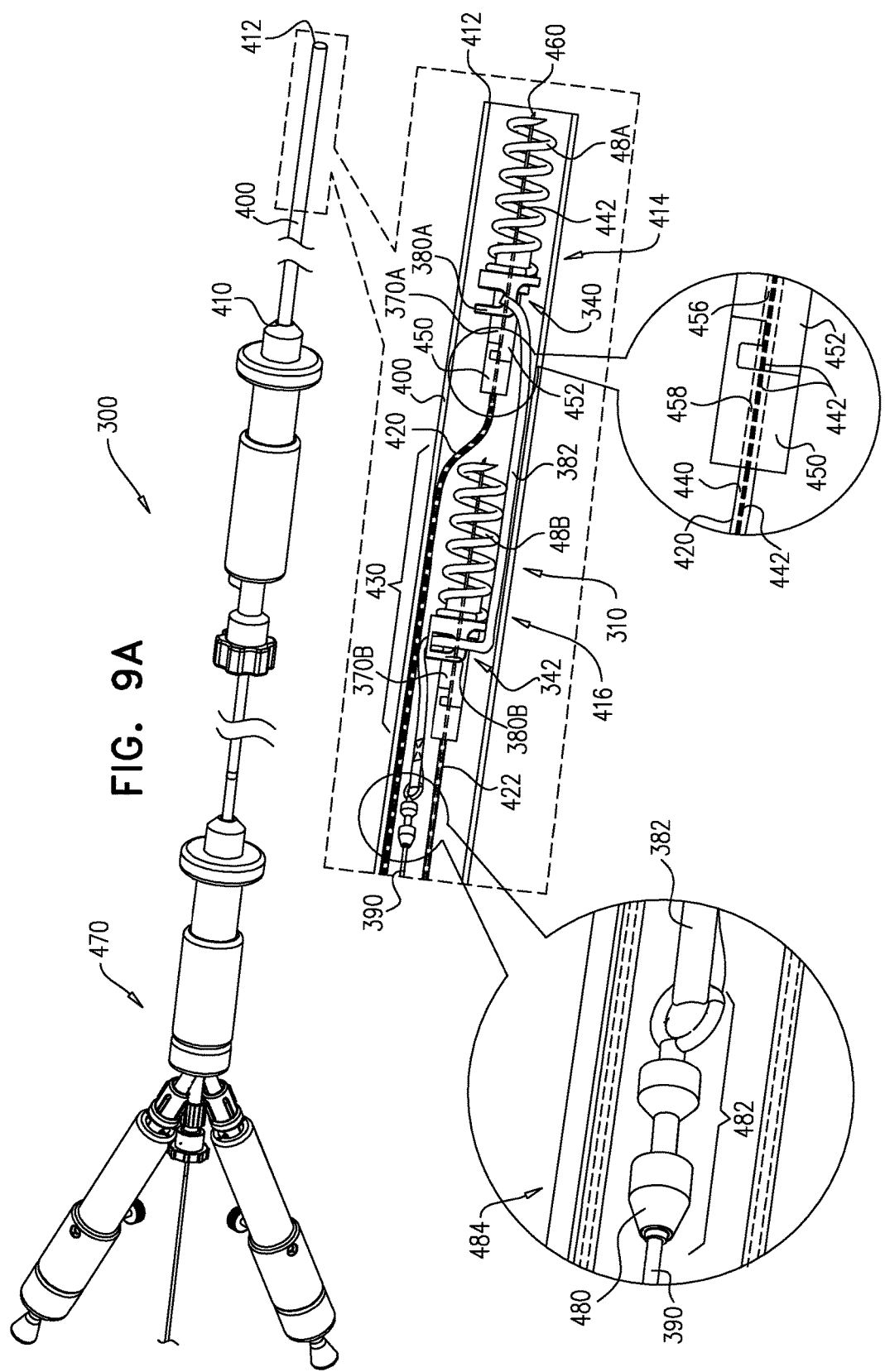
Figure 11D:
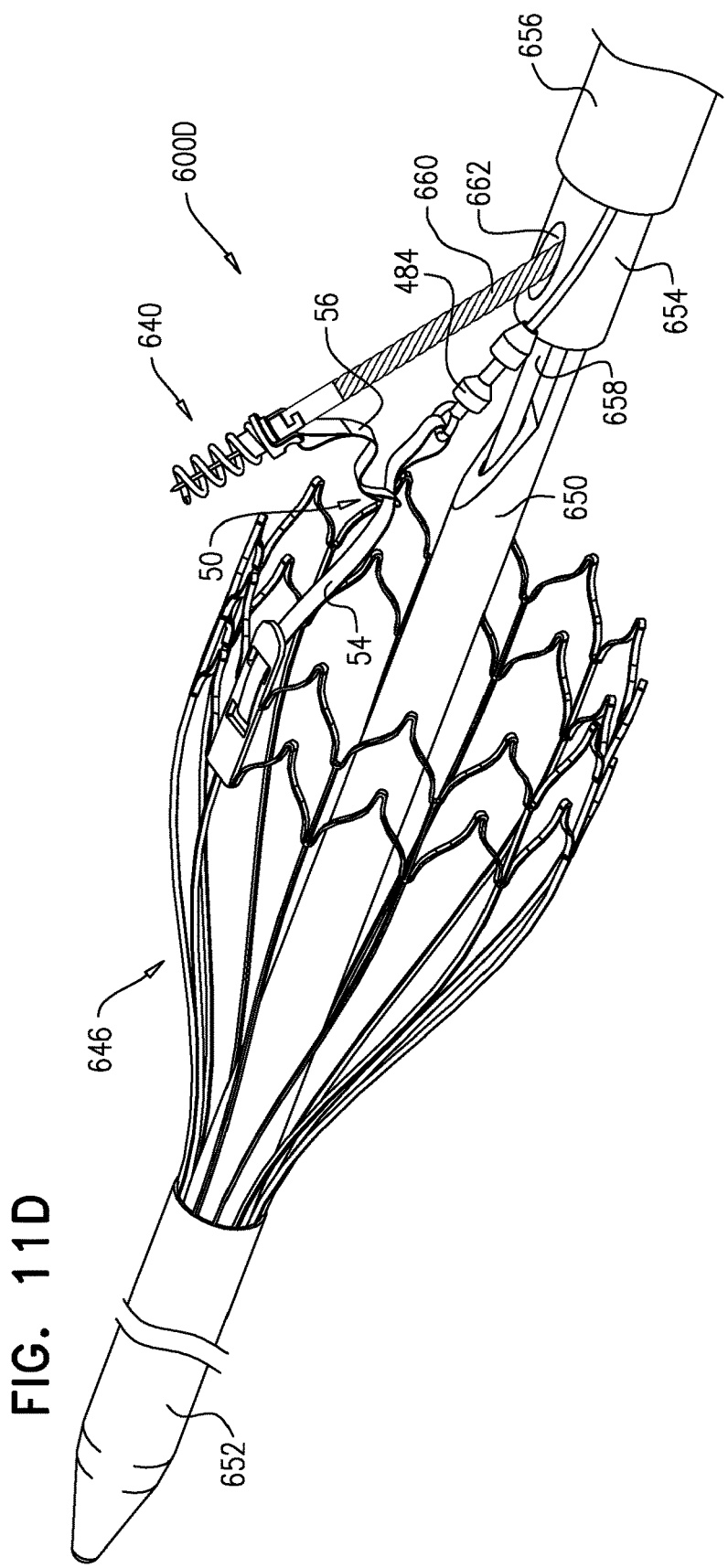

Reference is now made to FIGS. 9A and 9B, which are schematic illustrations of a delivery system comprising a multiple-anchor delivery tool 300, in accordance with respective applications of the present invention. Multiple-anchor delivery tool 300 is used to sequentially deliver and implant two or more tissue anchors of an implant 310.

Implant 310 comprises:
  at least first and second tissue anchors 340 and 342, which comprise (a) first and second helical tissue-coupling elements 48A and 48B, respectively, and (b) first and second heads 370A and 370B, respectively, which comprise first and second tether interfaces 380A and 380B; and
  a tether 382, which is connected (e.g., permanently fixed) to first tether interface 380A, and coupled to second tether interface 380B (optionally slidably coupled to second tether interface 380B, such that the tether slidably passes through the second tether interface).

For some applications, first tissue anchor 340 comprises second tissue anchor 40, second tissue anchor 140, or third tissue anchor 42, described hereinabove. Alternatively or additionally, for some applications, second tissue anchor 342 comprises second tissue anchor 40, second tissue anchor 140, or third tissue anchor 42, described hereinabove. For some applications, first tether interface 380A is rotatable with respect to first tissue-coupling element 48A, and/or second tether interface 380B is rotatable with respect to first tissue-coupling element 48B.

For some applications, implant 310 comprises a male coupling 480 of a first flexible-longitudinal-member-coupling element 482 of an intraluminal locking mechanism 484 which is connected to a female coupling during the implantation procedure, such as in order to allow implantation of the third tissue anchor with a separate catheter delivery system, such as described in above-mentioned US Patent Application Publication 2013/0018459, for example with reference to FIGS. 25-26 thereof.

For some applications, as shown in FIG. 9B, implant 310 comprises pulley 250, described hereinabove with reference to FIGS. 7-8H. The pulley may be connected to first flexible-longitudinal-member-coupling element 482. Although pulley 250 is shown comprising ring 60, described hereinabove with reference to FIG. 2C, the pulley may alternatively comprise another of the pulleys described herein, including those described with reference to FIG. 2A or 2D.

Multiple-anchor delivery tool 300 comprises a catheter shaft 400 having proximal and distal ends 410 and 412. First and second tissue anchors 340 and 342 are initially removably positioned in catheter shaft 400 at first and second longitudinal locations 414 and 416, respectively. First longitudinal location 414 is more distal than second longitudinal location 416. In other words, the tissue anchors are initially positioned in the desired sequence of deployment in the catheter shaft, with the first anchor to be deployed positioned more distally than the subsequent anchor(s) to be deployed. The tissue anchors are interconnected by tether 382.

Multiple-anchor delivery tool 300 further comprises first and second torque cables 420 and 422, which (a) are removably coupled to first and second heads 370A and 370B, respectively, (b) extend within catheter shaft 400 proximally from first and second heads 370A and 370B, respectively, and (c) transmit torque when rotated, for rotating tissue-coupling elements 48A and 48B, respectively, into tissue. Typically, the torque cables additionally transmit axial force, to enable pushing of the tissue-coupling elements 48A and 48B into the tissue as they are rotated. A portion 430 of first torque cable 420 is initially removably positioned alongside second tissue anchor 342 in catheter shaft 400. Thus each anchor is separately connected to a control handle 470 by its own torque cable, which allows full and separate control of deployment of each anchor by an operator of the multiple-anchor delivery tool.

For some applications, implant 310 comprises one or more additional tissue anchors, and tool 300) correspondingly comprises one or more additional torque cables, removably coupled to the tissue-coupling elements, as described herein. These additional tissue anchors are initially removably positioned in catheter shaft 400 proximal to second longitudinal location 416. For example, implant 310 may further comprise a third tissue anchor, which comprises (a) a third helical tissue-coupling elements, and (b) a third head, which comprises a third tether interface; the tether is coupled to (e.g., slidably coupled to) the third tether interface; the third tissue anchor is removably positioned in catheter shaft 400 at a third longitudinal location that is more proximal than second longitudinal location 416; and multiple-anchor delivery tool 300 further comprises a third torque cable, which (a) is removably coupled to the third head, (b) extends within the catheter shaft proximally from the third head, and (c) transmits torque when rotated, wherein a portion of the second torque cable is removably positioned alongside the third tissue anchor in the catheter shaft.

For some applications, first torque cable 420 is shaped so as to define a lumen 440 therethrough, and multiple-anchor delivery tool 300 further comprises a sharpened wire 442, which removably passes through lumen 440. A distal end of first torque cable 420 comprises a distal coupling element 450, which is configured to be removably coupled to a corresponding proximal coupling element 452 defined by a proximal portion of first head 370A. Distal and proximal coupling elements 450 and 452 are shaped so as to define corresponding interlocking surfaces, such that the coupling elements interlock, thereby mating the coupling elements to one another. Head 370A, including proximal coupling element 452, is shaped so as to define a first longitudinal channel 456 at least partially therethrough (typically entirely therethrough), which channel is coaxial with head 370A. Distal coupling element 450 is shaped so as to define a second longitudinal channel 458 therethrough, which is coaxial with lumen 440 of first torque cable 420. First and second channels 456 and 458 are radially aligned with one another. When a portion of sharpened wire 442 is positioned in these channels, the sharpened wire prevents decoupling of distal coupling element 450 from proximal coupling element 452. Upon removal of sharpened wire 442 from channels 456 and 458 and the coupling elements 450 and 452, the coupling elements are free to be decoupled from one another.

For some applications, sharpened wire 442 is shaped so as to define a sharp distal tip 460. For these applications, first tissue-coupling element 48A typically is helical, and sharpened wire 442 is initially removably positioned within a channel defined by the helix. As tissue-coupling element 48A is screwed into tissue, sharpened wire 442 penetrates and advances into the tissue along with the anchor to a certain depth in the tissue. For some applications, when the shaft penetrates to the certain depth, the sharpened wire is withdrawn slightly. Typically, after tissue-coupling element 48A has been fully implanted, sharpened wire 442 is withdrawn entirely from the tissue, and removed from the patient's body. Optionally, the sharp distal tip of sharpened wire 442 is inserted into the tissue slightly, even before insertion of tissue-coupling element 48A, in order to prevent sliding of the tissue-coupling element on the surface of the tissue before commencement of insertion of the tissue-coupling element into the tissue.

After implantation of tissue-coupling element 48A, sharpened wire 442 is withdrawn proximally from the channel of tissue-coupling element 48A and from channels 456 and 458 of distal and proximal coupling elements 450 and 452, thereby decoupling the coupling elements from one another, and decoupling first torque cable 420 from head 370A. After such proximal withdrawal, sharpened wire 442 typically remains within lumen 440 of first torque cable 420.

Figure 12B:
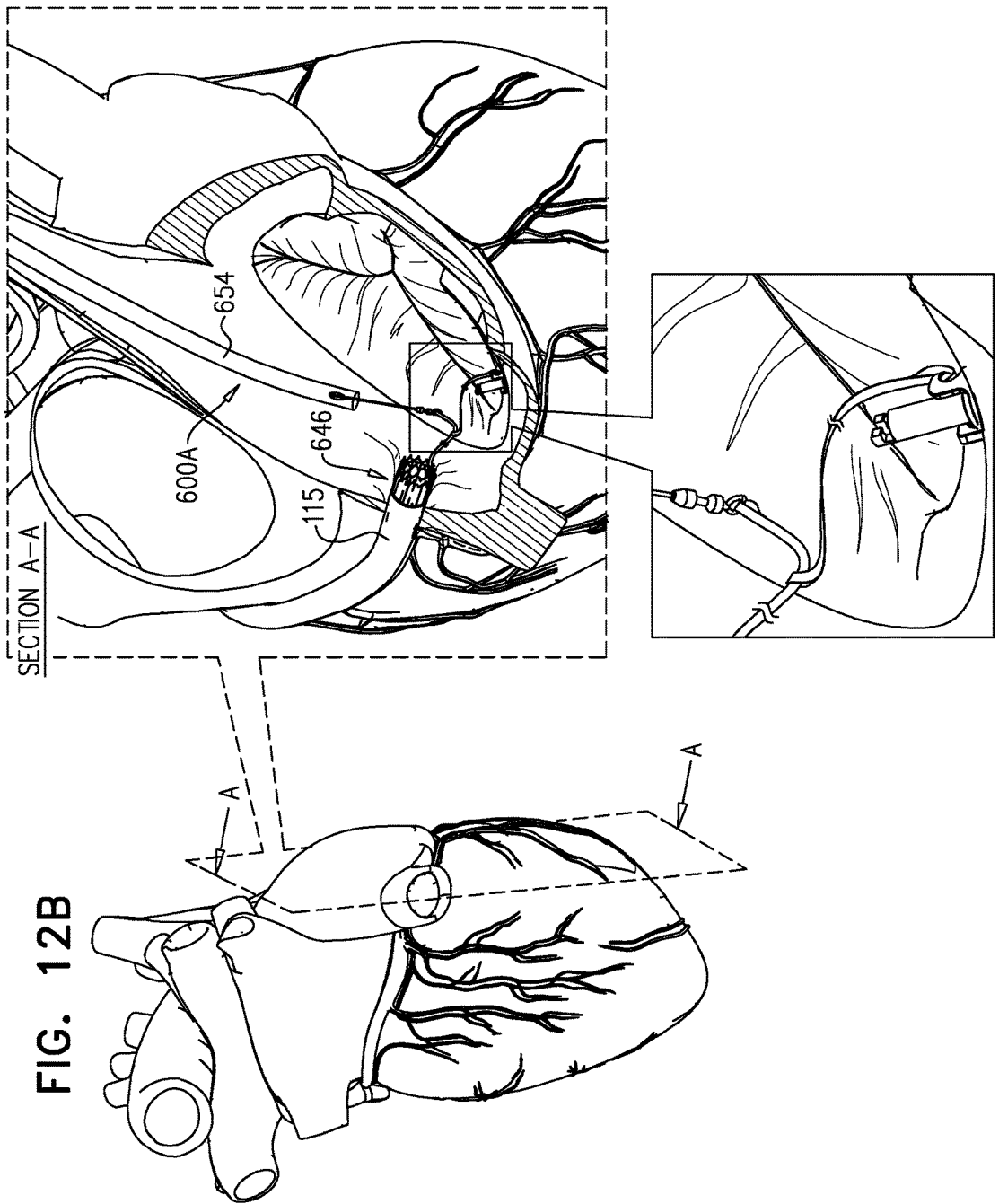

For some applications, the decoupling of first torque cable 420 and head 370A is performed alternatively or additionally using techniques described in US Patent Application Publication 2012/0035712, which is assigned to the assignee of the present application and is incorporated herein by reference, such as with reference to FIGS. 12A-C thereof.

Second torque cable 422 and second tissue anchor 342 similarly comprise the above-mentioned elements (e.g., the sharpened wire and coupling elements), and are similarly configured, as do any additional torque cables and tissue anchors that may be provided, as described above.

Multiple-anchor delivery tool 300 further comprises control handle 470, which is configured to control the deployment of the tissue anchors, by rotating the torque cables, distally advancing the anchors through catheter shaft 400, and proximally withdrawing the sharpened wire and torque cables. Control handle 470 may implement features of handle portion 1004, described with reference to FIG. 11C of above-mentioned US Patent Application Publication 2012/0035712, mutatis mutandis.

Reference is now made to FIGS. 10A-C, which are schematic illustrations of a deployment method using multiple-anchor delivery tool 300, in accordance with an application of the present invention. This method may be used to deploy second tissue anchor 40, second tissue anchor 140, and/or third tissue anchor 42, described hereinabove, or other tissue anchors. Although FIGS. 10A-C illustrate the implantation of the configuration of implant 310 shown in FIG. 9B, the same techniques can be used for the implantation of the configuration shown in FIG. 9A. Catheter shaft 400 is typically advanced transvascularly, using a delivery system comprising one or more catheters introduced with the aid of a guidewire, through vasculature of the subject, such as (a) via the femoral vein, through inferior vena cava 80, and into a right atrium 81, (b) via the basilic vein, through the subclavian vein through superior vena cava 110, and into right atrium 81, or (c) via the external jugular vein, through the subclavian vein through superior vena cava 110, and into right atrium 81. The procedure is typically performed with the aid of imaging, such as fluoroscopy, transesophageal echo, and/or echocardiography. The procedure may be performed using techniques described in US Patent Application Publication 2012/0035712, which is assigned to the assignee of the present application and is incorporated herein by reference, with reference to FIGS. 1A-D thereof, mutatis mutandis.

Distal end 412 of catheter shaft 400 of multiple-anchor delivery tool 300 is advanced into the body of a subject, while (a) first and second tissue anchors 340 and 342 are removably positioned in catheter shaft 400 at first and second longitudinal locations 414 and 416, respectively, first longitudinal location 414 more distal than second longitudinal location 416. Portion 430 of first torque cable 420 is removably positioned alongside second tissue anchor 342 in catheter shaft 400. Thus, catheter shaft 400 does not need to be withdrawn and reintroduced from the body during the implantation procedure.

As shown in FIG. 10A, first tissue anchor 340 is implanted into tissue 500 of the subject (e.g., cardiac muscle tissue, such as atrial tissue) by rotating first torque cable 420, using control handle 470, and, typically pushing distally on the torque cable.

As shown in FIG. 10B, after first tissue anchor 340 has been fully implanted in tissue 500, first torque cable 420 is decoupled from first tissue anchor 340, such as by proximally withdrawing sharpened wire 442, as described hereinabove with reference to FIGS. 9A-B. First torque cable 420 is typically further proximally withdrawn in catheter shaft 400 (not shown), and optionally withdrawn out of the proximal end of the catheter shaft.

As shown in FIG. 10C, after first tissue anchor 340 is implanted, second tissue anchor 342 is distally advanced in catheter shaft 400, and implanted into tissue 500 by rotating second torque cable 422. The second torque cable is decoupled from second tissue anchor 342 (not shown). First and second tissue anchors 340 and 342 remain implanted in tissue 500, connected by tether 382, with the pulley freely movable on it.

Pulley 250, which extends distally from second tether interface 380B, may be tensioned so as to apply tension between the first and the second tissue anchors, as described hereinabove with reference to FIGS. 8A-H. For example, pulley 250 may be removably connected to a flexible longitudinal guide member 390 by first flexible-longitudinal-member-coupling element 482, which may be coupled to the female part of the locking mechanism using a separate catheter delivery system containing first venous tissue anchor 30, such as described in above-mentioned US Patent Application Publication 2013/0018459, for example with reference to FIGS. 23-26 thereof, mutatis mutandis (in which flexible longitudinal guide member 2616 corresponds to flexible longitudinal guide member 390 of the present application).

Reference is now made to FIGS. 11A-D, which are schematic illustrations of a delivery system comprising multiple-anchor delivery tools 600A, 600B, 600C, and 600D, respectively, in accordance with respective applications of the present invention. Multiple-anchor delivery tools 600 are used to sequentially deliver and implant one or more helical tissue anchors 640 and an intraluminal stent anchor 646 of an implant, such as one of the implants described hereinabove. As described below, multiple-anchor delivery tools 600 may be used alone or in combination with multiple-anchor delivery tool 300, described hereinabove with reference to FIGS. 9A-B.

Each of multiple-anchor delivery tools 600 typically comprises an inner stent-deployment shaft 650, a distal tubular tip element 652, an outer shaft 654, and an outer delivery catheter 656. Stent anchor 646 is initially removably disposed surrounding a longitudinal portion of inner stent-deployment shaft 650 and within distal tubular tip element 652. With the stent anchor thus positioned, distal tubular tip element 652 is pushed into coronary sinus 115. Distal advancement of distal tubular tip element 652 with respect to inner stent-deployment shaft 650 releases stent anchor 646, which typically self-expands upon release. For example, the distal tubular tip element may be advanced distally by distally advancing a pusher rod 658 that passes through a channel of inner stent-deployment shaft 650 and is coupled to the distal tubular tip element (typically to a distal end thereof, within the tip element). Inner stent-deployment shaft 650 is slidably disposed within a channel of outer shaft 654, which itself is advanceable within a channel of outer delivery catheter 656. As shown in FIG. 11C, pusher rod 658 and a distal portion of tip element 652 typically are shaped so as to define a channel therethrough, through which a guidewire 670 passes.

Reference is made to FIG. 11A. Multiple-anchor delivery tool 600A is configured to deploy a helical tissue anchor 640 and stent anchor 646. Multiple-anchor delivery tool 600A is capable of deploying either the helical tissue anchor or the stent anchor first. Helical tissue anchor 640 is deployed using an anchor-deployment shaft 660, which passes through outer shaft 654, and typically exits the outer shaft through a lateral opening 662. Stent anchor 646 and helical tissue anchor 640 are tensioned to a stent venous tissue anchor (such as first venous tissue anchor 30) in SVC 110 or IVC 80, such as described hereinabove with reference to FIGS. 3L, 3M, 3P, and 3Q (the configuration described with reference to FIG. 6F is also similar). (For use in the deployments described hereinabove with reference to FIGS. 3P and 3Q, the pulley is connected to stent anchor 646 rather than to helical tissue anchor 640, and the tether to the stent venous tissue anchor is connected to helical tissue anchor 640, rather than to stent anchor 646.) For some applications, multiple-anchor delivery tool 600A is used as described hereinbelow with reference to FIGS. 12A-C.

Reference is made to FIG. 11B. Multiple-anchor delivery tool 600B is configured to deploy a female coupling element 680 and stent anchor 646. Stent anchor delivery tool 600B is capable of deploying stent anchor and connecting it to the male locking mechanism of multiple anchor deploying system such as described in FIG. 9A. Female coupling element 680 is deployed using shaft 660, which passes through outer shaft 654, and typically exits the outer shaft through a lateral opening 662. The stent anchor and the female coupling element are tethered together by a textile band. Female coupling element 680 may be connected to a male coupling element during the implantation procedure. The female and male coupling elements may be components of intraluminal locking mechanism 55, described hereinabove with reference to FIGS. 1, 3A-Q, 4, 6A-I, 7, and 8A-H. The male and female coupling elements may be connected using techniques described in US Patent Application Publication 2013/0018459, such as with reference to FIGS. 20-32 thereof. Female coupling element 680 is then used to tether the first two helical tissue anchors, such as described hereinabove with reference to FIG. 9A, to a coronary sinus stent. The coronary sinus stent is then pushed forward into the coronary sinus, thereby tensioning the tether system.

Reference is made to FIG. 11C. Multiple-anchor delivery tool 600C is configured to deploy two helical tissue anchors 640A and 640B, and stent anchor 646. Typically, multiple-anchor delivery tool 600C first deploys the two helical tissue anchors, using respective anchor-deployment shafts 660A and 660B, both of which pass through outer shaft 654, and typically exit the outer shaft through respective lateral openings 662A and 662B. Thereafter, multiple-anchor delivery tool 600C is used to push distal tubular tip element 652 into coronary sinus 115, with stent anchor 646 removably disposed surrounding the longitudinal portion of inner stent-deployment shaft 650 and within distal tubular tip element 652. Distal tubular tip element 652 is advanced in the coronary sinus until sufficient tension has been applied to the tethers and thus to the valve. For example, multiple-anchor delivery tool 600C may be used to achieve the deployment configurations described hereinabove with reference to FIGS. 3J, 3K, and 3N (FIGS. 6H, 6I, 8E, 8F, and 8G also show similar configurations). In order to accommodate additional deployment configurations, the pulley may be connected to the appropriate tissue anchor of the system. Although the pulley is shown connected to tissue anchor 640B, it may alternatively be connected to tissue anchor 640A.

Reference is made to FIG. 1D. Multiple-anchor delivery tool 600D is configured to deploy a helical tissue anchor 640 and stent anchor 646. Multiple-anchor delivery tool 600D is capable of deploying either the helical tissue anchor or the stent anchor first. Stent anchor 646 is connected to first venous tissue anchor 30 in SVC 110 or IVC 80, via a tether, such as using mating techniques described in US Patent Application Publication 2013/0018459, as described hereinabove. For some applications, multiple-anchor delivery tool 600D is used to achieve the deployment configurations described hereinabove with reference to FIGS. 3L, 3M, and 6F.

Reference is now made to FIGS. 12A-C, which are schematic illustrations of the deployment of a valve-tensioning implant system using multiple-anchor delivery tool 600A, in accordance with an application of the present invention. Similar techniques can be used for deployment of a valve-tensioning implant using multiple-anchor delivery tools 600B, 600C, and 600D, mutatis mutandis.

As shown in FIG. 12A, multiple-anchor delivery tool 600A is used to first deploy stent anchor 646 in coronary sinus 115, as described hereinabove with reference to FIGS. 11A-D.

As shown in FIG. 12B, multiple-anchor delivery tool 600A is then used to deploy helical tissue anchor 640 on the annulus. Alternatively, helical tissue anchor 640 is deployed before stent anchor 646.

As shown in FIG. 12C, a venous tissue anchor 30 is deployed in SVC 110 and tension is applied on a first tether 740 connecting venous tissue anchor 30 and stent anchor 646 to a pulley 750, which is connected by a second tether 742 to helical tissue anchor 640.

The following table sets forth exemplary uses of multiple-anchor delivery tool 300, described hereinabove with reference to FIGS. 9A-B, and/or multiple-anchor delivery tools 600A, 600B, 600C, or 600D, to achieve some of the deployment configurations described hereinabove. One or more of these delivery tools may optionally be used to achieve others of the deployment configurations described hereinabove, mutatis mutandis.

TABLE 4

| First implantation site 89 | Second implantation site 190 (pulley) anatomical marker | Third implantation site 192 anatomical marker | FIG. | Delivery method | Sequence of Delivery |
|---|---|---|---|---|---|
| Inferior vena cava 80 | Circumferential middle 93 of septal leaflet 82 | Anteroposterior commissure 112 | FIG. 6A | Using sequence of FIGS. 10A-C and multiple-anchor delivery tool 300 | Helical tissue anchors in any order and then stent anchor |
| Inferior vena cava 80 | Anteroposterior commissure 112 | Circumferential middle 93 of septal leaflet 82 | FIG. 6B | Using sequence of FIGS. 10A-C and multiple-anchor delivery tool 300 | Helical tissue anchors in any order and then stent anchor |
| Inferior vena cava 80 | Circumferential middle 119 of posterior leaflet 84 | Septoanterior commissure 114 | FIG. 6C | Using sequence of FIGS. 10A-C and multiple-anchor delivery tool 300 | Helical tissue anchors in any order and then stent anchor |
| Inferior vena cava 80 | Septoanterior commissure 114 | Circumferential middle 119 of posterior leaflet 84 | FIG. 6D | Using sequence of FIGS. 10A-C and multiple-anchor delivery tool 300 | Helical tissue anchors in any order and then stent anchor |
| Superior vena cava 110 | Circumferential middle 121 of anterior leaflet 86 | Circumferential middle 119 of posterior leaflet 84 | FIG. 6E | Using sequence of FIGS. 10A-C and multiple-anchor delivery tool 300 | Helical tissue anchors in any order and then stent anchor |
| Superior vena cava 110 | Anteroposterior commissure 112 | Coronary Sinus 115 | FIG. 6F | Using sequence of FIGS. 12A-B and multiple-anchor delivery tool 600A | Helical tissue anchor or stent anchor first in CS and then the stent anchor in SVC 110 |
| Superior vena cava 110 | Circumferential middle 119 of posterior leaflet 84 | Circumferential middle 121 of anterior leaflet 86 | FIG. 6G | Using sequence of FIGS. 10A-C and multiple-anchor delivery tool 300 | Helical tissue anchors in any order and then stent anchor |
| Coronary Sinus 115 | Anteroposterior commissure 112 | Septoanterior commissure 114 | FIG. 6H | Multiple-anchor delivery tool 600C | Helical tissue anchors in any order and then stent anchor |
| Coronary Sinus 115 | Circumferential middle 121 of anterior leaflet 86 | Circumferential middle 119 of posterior leaflet 84 | FIG. 6I | Multiple-anchor delivery tool 600C | Helical tissue anchors in any order and then stent anchor |

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. Pat. No. 8,475,525 to Maisano et al.;

International Application PCT/IL2011/000064, filed Jan. 20, 2011, which published as PCT Publication WO 2011/089601, and U.S. application Ser. No. 13/574,088 in the national stage thereof, which published as US Patent Application Publication 2013/0046380;

U.S. application Ser. No. 13/188,175, filed Jul. 21, 2011, which published as US Patent Application Publication 2012/0035712;

U.S. application Ser. No. 13/485,145, filed May 31, 2012, which published as US Patent Application Publication 2013/0325115;

U.S. application Ser. No. 13/553,081, filed Jul. 19, 2012, which published as US Patent Application Publication 2013/0018459;

International Application PCT/IL2012/000282, filed Jul. 19, 2012, which published as PCT Publication WO 2013/011502;

U.S. Provisional Application 61/750,427, filed Jan. 9, 2013;

U.S. Provisional Application 61/783,224, filed Mar. 14, 2013;

International Application PCT/IL2013/050470, filed May 30, 2013, which published as PCT Publication WO 2013/179295;

U.S. Provisional Application 61/897,491, filed Oct. 30, 2013;

U.S. application Ser. No. 14/143,355, filed Dec. 30, 2013, which published as US Patent Application Publication 2014/0114390;

International Application PCT/IL2014/050027, filed Jan. 9, 2014, which published as PCT Publication WO 2014/108903;

International Application PCT/IL2014/050233, filed Mar. 9, 2014, which published as PCT Publication WO 2014/141239; and U.S. Provisional Application 62/014,397, filed Jun. 19, 2014.

In particular, the stents described herein may be used as one or more of the stents described in the above-listed applications, in combination with the other techniques described therein.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:
   implanting:
      a venous first tissue anchor in a vein selected from the group of veins consisting of: a superior vena cava and an inferior vena cava,
      an atrial second tissue anchor at an atrial site selected from the group of sites consisting of: an annulus of a tricuspid valve, and a wall of a right atrium of a heart above the annulus of the tricuspid valve,
      a venous third tissue anchor in a coronary sinus, and
      one or more tethers, which connect the venous first tissue anchor, the atrial second tissue anchor, and the venous third tissue anchor; and
   reducing a size of a tricuspid orifice by tensioning the one or more tethers.

2. The method according to claim 1,
   wherein the venous first tissue anchor and the venous third tissue anchor include first and second intraluminal stents, respectively,
   wherein implanting the venous first tissue anchor comprises expanding the first intraluminal stent in the selected vein, and
   wherein implanting the venous third tissue anchor comprises expanding the second intraluminal stent in the coronary sinus.

3. The method according to claim 2, wherein a greatest outer diameter of the second intraluminal stent is no more than 80% of a greatest outer diameter of the first intraluminal stent, when the first and the second intraluminal stents are unconstrained and fully radially expanded.

4. The method according to claim 2, wherein the atrial second tissue anchor includes a helical tissue-coupling element, and wherein implanting the atrial second tissue anchor comprises rotating the helical tissue-coupling element into tissue at the site.

5. The method according to claim 1, wherein implanting the venous first tissue anchor comprises implanting the venous first tissue anchor in the inferior vena cava.

6. The method according to claim 5, wherein implanting the atrial second tissue anchor comprises implanting the atrial second tissue anchor within 1 cm of a site on the annulus that circumferentially corresponds to an anteroposterior commissure of the tricuspid valve.

7. The method according to claim 1, wherein implanting the venous first tissue anchor comprises implanting the venous first tissue anchor in the superior vena cava.

8. The method according to claim 7, wherein implanting the atrial second tissue anchor comprises implanting the atrial second tissue anchor within 1 cm of a site on the annulus that circumferentially corresponds to an anteroposterior commissure of the tricuspid valve.

9. The method according to claim 1, wherein the atrial second tissue anchor includes a helical tissue-coupling element and a head.

10. The method according to claim 1,
    wherein implanting comprises implanting a pulley system, which (a) is connected to the venous first tissue anchor, the atrial second tissue anchor, and the venous third tissue anchor, and (b) includes a pulley, and
    wherein reducing the size of the tricuspid orifice by tensioning the one or more tethers comprises using the pulley system to distribute and transfer forces between the venous first tissue anchor, the atrial second tissue anchor, and the venous third tissue anchor.

11. The method according to claim 1, wherein implanting comprises implanting a pulley system, which includes (a) a pulley, which is connected to the atrial second tissue anchor, and (b) a first tether of the one or more tethers, which first tether (i) is connected to the venous first tissue anchor and the venous third tissue anchor, (ii) is moveable through the pulley, and (iii) has a first length, measured between the venous first tissue anchor and the venous third tissue anchor, of at least 15 mm.

12. The method according to claim 11, wherein the pulley includes a loop, and wherein tensioning the first tether comprises sliding the first tether through the loop.

13. The method according to claim 12, wherein the loop is a closed loop.

14. The method according to claim 11, wherein the pulley includes a ring, and wherein tensioning the first tether comprises sliding the first tether through the ring.

15. The method according to claim 11, wherein the pulley includes a wheel, and wherein tensioning the first tether comprises rotating the wheel by moving the first tether through the pulley.

16. The method according to claim 11, wherein implanting the venous first tissue anchor, the atrial second tissue anchor, the venous third tissue anchor, and the pulley system comprises positioning the venous first tissue anchor, the atrial second tissue anchor, the venous third tissue anchor, and the pulley system such that two longitudinal portions of the first tether adjacent to and on opposite sides of the pulley define an angle therebetween of between 5 and 150 degrees.

17. The method according to claim 11,
wherein the pulley system further includes a second tether of the one or more tethers, which second tether (a) is connected to the pulley and the atrial second tissue anchor, so as to connect the pulley to the atrial second tissue anchor, and (b) has a second length, measured between the atrial second tissue anchor and the pulley, of at least 3 mm, and
wherein implanting the pulley system further comprises implanting the second tether.

18. The method according to claim 11,
wherein the atrial second tissue anchor includes (a) a tissue-coupling element, and (b) a head,
wherein the pulley is connected to the head, and
wherein tensioning the one or more tethers comprises tensioning the first tether by fully extending the pulley away from the head, such that a distance between (a) a site on the pulley farthest from the head and (b) a site on the head closest to the pulley, is at least 3 mm.

19. The method according to claim 18, wherein the head includes an interface that is rotatable with respect to the tissue-coupling element.

20. The method according to claim 11, wherein the atrial second tissue anchor includes (a) a tissue-coupling element, and (b) a head, which includes the pulley, and wherein implanting the atrial second tissue anchor comprises implanting the head.

21. The method according to claim 20, wherein the head includes an interface, which (a) includes the pulley and (b) is rotatable with respect to the tissue-coupling element.

22. The method according to claim 1, wherein implanting comprises implanting a pulley system, which includes (a) a pulley, which is connected to the venous third tissue anchor, and (b) a first tether of the one or more tethers, which first tether (i) is connected to the venous first tissue anchor and the atrial second tissue anchor, (ii) is moveable through the pulley, and (iii) has a first length, measured between the venous first tissue anchor and the atrial second tissue anchor, of at least 15 mm.

23. The method according to claim 22, wherein the pulley includes a loop, and wherein tensioning the one or more tethers comprises tensioning the first tether by sliding the first tether through the loop.

24. The method according to claim 23, wherein the loop is a closed loop.

25. The method according to claim 22, wherein the pulley includes a ring, and wherein tensioning the one or more tethers comprises tensioning the first tether by sliding the first tether through the ring.

26. The method according to claim 22, wherein the pulley includes a wheel, and wherein tensioning the one or more tethers comprises tensioning the first tether by rotating the wheel by moving the first tether through the pulley.

27. The method according to claim 22, wherein implanting the venous first tissue anchor, the atrial second tissue anchor, the venous third tissue anchor, and the pulley system comprises positioning the venous first tissue anchor, the atrial second tissue anchor, the venous third tissue anchor, and the pulley system such that two longitudinal portions of the first tether adjacent to and on opposite sides of the pulley define an angle therebetween of between 5 and 150 degrees.

28. The method according to claim 22,
wherein the pulley system further includes a second tether of the one or more tethers, which second tether (a) is connected to the pulley and the venous third tissue anchor, so as to connect the pulley to the venous third tissue anchor, and (b) has a second length, measured between the venous third tissue anchor and the pulley, of at least 3 mm, and
wherein implanting the pulley system further comprises implanting the second tether.

* * * * *